US011647963B2

(12) United States Patent
Ong et al.

(10) Patent No.: US 11,647,963 B2
(45) Date of Patent: *May 16, 2023

(54) SYSTEM AND METHOD FOR PREDICTING ACUTE CARDIOPULMONARY EVENTS AND SURVIVABILITY OF A PATIENT

(71) Applicants: SINGAPORE HEALTH SERVICES PTE LTD., Singapore (SG); NANYANG TECHNOLOGICAL UNIVERSITY, Singapore (SG)

(72) Inventors: Marcus Eng Hock Ong, Singapore (SG); Zhiping Lin, Singapore (SG); Wee Ser, Singapore (SG); Guangbin Huang, Singapore (SG)

(73) Assignees: SINGAPORE HEALTH SERVICES PTE LTD., Singapore (SG); NANYANG TECHNOLOGICAL UNIVERSITY, Singapore (SG)

( * ) Notice: Subject to any disclaimer, the term of this patent is extended or adjusted under 35 U.S.C. 154(b) by 182 days.

This patent is subject to a terminal disclaimer.

(21) Appl. No.: 17/115,142

(22) Filed: Dec. 8, 2020

(65) Prior Publication Data

US 2021/0251575 A1 Aug. 19, 2021

Related U.S. Application Data

(60) Continuation of application No. 16/161,876, filed on Oct. 16, 2018, now Pat. No. 10,888,282, which is a (Continued)

(51) Int. Cl.
*A61B 5/00* (2006.01)
*A61B 5/01* (2006.01)
(Continued)

(52) U.S. Cl.
CPC .............. *A61B 5/7275* (2013.01); *A61B 5/01* (2013.01); *A61B 5/0205* (2013.01);
(Continued)

(58) Field of Classification Search
CPC ..... A61B 5/01; A61B 5/0205; A61B 5/02055; A61B 5/021; A61B 5/02405;
(Continued)

(56) References Cited

U.S. PATENT DOCUMENTS 4,957,115 A 9/1990 Selker
5,501,229 A 3/1996 Selker et al.
(Continued)

FOREIGN PATENT DOCUMENTS

CN 2437291 Y 7/2001
JP 2002143097 A 5/2002
(Continued)

OTHER PUBLICATIONS

"Heart Rate Variability: Standards of Measurement, Physiological Interpretation, and Clinical Use", Circulation, Lippincott Williams & Wilkins, U.S., vol. 93, No. 5, Jan. 1, 1996, pp. 1043-1065.
(Continued)

*Primary Examiner* — Brian T Gedeon
(74) *Attorney, Agent, or Firm* — Lando & Anastasi, LLP

(57) ABSTRACT

A method of producing an artificial neural network capable of predicting the survivability of a patient, including: storing in an electronic database patient health data comprising a plurality of sets of data, each set having at least one of a first parameter relating to heart rate variability data and a second parameter relating to vital sign data, each set further having a third parameter relating to patient survivability; providing a network of nodes interconnected to form an artificial neural network, the nodes comprising a plurality of artificial neurons, each artificial neuron having at least one input with
(Continued)

an associated weight; and training the artificial neural network using the patient health data such that the associated weight of the at least one input of each artificial neuron is adjusted in response to respective first, second and third parameters of different sets of data from the patient health data.

21 Claims, 27 Drawing Sheets

Related U.S. Application Data continuation of application No. 15/709,608, filed on Sep. 20, 2017, now Pat. No. 10,136,861, which is a continuation of application No. 15/227,212, filed on Aug. 3, 2016, now Pat. No. 9,795,342, which is a continuation of application No. 14/616,057, filed on Feb. 6, 2015, now Pat. No. 9,420,957, which is a continuation of application No. 14/199,495, filed on Mar. 6, 2014, now Pat. No. 8,951,193, which is a division of application No. 13/868,605, filed on Apr. 23, 2013, now Pat. No. 8,668,644, which is a continuation of application No. 13/047,348, filed on Mar. 14, 2011, now abandoned.

(60) Provisional application No. 61/313,822, filed on Mar. 15, 2010.

(51) Int. Cl.
| | | |
|---|---|---|
| *A61B 5/0205* | (2006.01) | |
| *A61B 5/1455* | (2006.01) | |
| *A61B 5/024* | (2006.01) | |
| *A61B 5/316* | (2021.01) | |
| *A61B 5/318* | (2021.01) | |
| *G16H 50/20* | (2018.01) | |
| *A61B 5/021* | (2006.01) | |
| *A61B 5/352* | (2021.01) | |
| *A61B 5/361* | (2021.01) | |
| *G16Z 99/00* | (2019.01) | |
| *A61B 5/145* | (2006.01) | |
| *G06N 3/04* | (2023.01) | |
| *G06N 3/08* | (2023.01) | |
| *A61B 34/10* | (2016.01) | |
| *A61B 5/364* | (2021.01) | |
| *A61B 5/08* | (2006.01) | |

(52) U.S. Cl.
CPC ...... *A61B 5/02055* (2013.01); *A61B 5/02405* (2013.01); *A61B 5/14542* (2013.01); *A61B 5/14551* (2013.01); *A61B 5/316* (2021.01); *A61B 5/318* (2021.01); *A61B 5/352* (2021.01); *A61B 5/361* (2021.01); *A61B 5/4824* (2013.01); *A61B 5/4836* (2013.01); *A61B 5/6801* (2013.01); *A61B 5/7264* (2013.01); *A61B 5/7267* (2013.01); *A61B 5/742* (2013.01); *A61B 34/10* (2016.02); *G06N 3/04* (2013.01); *G06N 3/08* (2013.01); *G16H 50/20* (2018.01); *G16Z 99/00* (2019.02); *A61B 5/021* (2013.01); *A61B 5/0816* (2013.01); *A61B 5/364* (2021.01)

(58) Field of Classification Search
CPC . A61B 5/04014; A61B 5/0402; A61B 5/0456; A61B 5/046; A61B 5/0468; A61B 5/0816; A61B 5/14542; A61B 5/14551; A61B 5/4824; A61B 5/4836; A61B 5/6801; A61B 5/7264; A61B 5/7267; A61B 5/742

See application file for complete search history.

(56) References Cited

U.S. PATENT DOCUMENTS

| | | |
|---|---|---|
| 5,755,671 A | 5/1998 | Mbrecht et al. |
| 6,454,707 B1 | 9/2002 | Casscells, III et al. |
| 6,656,125 B2 | 12/2003 | Misczynski et al. |
| 6,665,559 B2 | 12/2003 | Rowlandson |
| 7,142,907 B2 | 11/2006 | Xue et al. |
| 7,272,435 B2 | 9/2007 | Rowlandson |
| 8,668,644 B2 | 3/2014 | Ong et al. |
| 8,932,220 B2 | 1/2015 | Ong et al. |
| 8,951,193 B2 | 2/2015 | Ong et al. |
| 9,420,957 B2 | 8/2016 | Ong et al. |
| 9,795,342 B2 | 10/2017 | Ong et al. |
| 10,136,861 B2 | 11/2018 | Ong et al. |
| 2005/0004481 A1 | 1/2005 | Xue et al. |
| 2007/0060785 A1 | 3/2007 | Freeman et al. |
| 2007/0093720 A1 | 4/2007 | Fischell et al. |
| 2007/0112275 A1 | 5/2007 | Cooke et al. |
| 2007/0276275 A1 | 11/2007 | Proctor et al. |
| 2009/0177102 A1 | 7/2009 | Schneider et al. |
| 2009/0234410 A1 | 9/2009 | Libbus et al. |
| 2010/0057490 A1 | 3/2010 | Kocis et al. |
| 2011/0224565 A1 | 9/2011 | Ong et al. |
| 2015/0150468 A1 | 6/2015 | Ong et al. |
| 2019/0150850 A1 | 5/2019 | Ong et al. |

FOREIGN PATENT DOCUMENTS

| | | |
|---|---|---|
| JP | 2006511881 A | 4/2006 |
| JP | 2010502308 A | 1/2010 |
| WO | 200053084 A1 | 9/2000 |
| WO | 2007149856 A2 | 12/2007 |
| WO | 2009138976 A2 | 11/2009 |

OTHER PUBLICATIONS

Alistair Hann, "Multi-parameter Monitoring for Early Warning of Patient Deterioration," Department of Engineering Science, University of Oxford, Mar. 2008, pp. 1-190.
Baxt, W. et al., "A Neural Network Aid for the Early Diagnosis of Cardiac Ischemia in Patients Presenting to the Emergency Department Wtih Chest Pain", Annals of Emergency Medicine, vol. 40, No. 6, Dec. 1, 2002, pp. 575-583.
Carpeggiani et al.: "Early assessment of heart rate variability is predictive of in-hospital death and major complications after acute myocardial infarction", International Journal of Cardiology, US, Elsevier, Sep. 2004, 96(3), 361-8.
Extended European Search Report from corresponding European Application No. 18193483.7 dated Jan. 7, 2019.
Fei et al.: "Short- and long-term assessment of heart rate variability for risk stratification after acute myocardial infarction", American Journal of Cardiology, US, Elsevier, Apr. 1996, 77(9), 681-4.
Final Office Action from corresponding Japanese Application No. 2016-191388 dated Jan. 23, 2018.
Harrison et al., "Artificial Neural Network Models for Prediction of Acute Coronary Syndromes Using Clinical Data From the Time of Presentation", Annals of Emergency Medicine, Lansing, MI, vol. 46, No. 5, November , 1005, pp. 431-439.
International Preliminary Report on Patentability for International Application No. PCT/SG2011/000102 dated Sep. 27, 2012.
International Search Report and Written Opinion for International Application No. PCT/IB2013/001890 dated Jun. 14, 2013.
International Search Report and Written Opinion for International Application No. PCT/SG2011/000102 dated Feb. 13, 2012.
Japanese Office Action from corresponding Japanese Application No. 2018-098787 dated Mar. 19, 2019.
Keith, K.D.: "Emergency department revisits", Annals of Emergency Medicine, US, Elsevier, Sep. 1989, 18(9), 964-8.

(56) References Cited

OTHER PUBLICATIONS

Lerman et al.: "Return visits to the emergency department", The Journal of Emergency Medicine, US, Elsevier, Sep. 1987, 5(5), 359-362.

Liu et al. "Patient Outcome Prediction with Heart Rate Variability and Vital Signs". J Sign Process Syst (2011) 64:265-278.

Matsubara, Jin. "Gaming of Disaster Rescue, RoboCup Rescue Project." Information Processing Society of Japan, May 2002, vol. 43, No. 5, 531-536.

Matsuno, Fumitoshi. "The front line of development of rescue robots and systems." Sangyo Kaihatsukiko Inc., Jan. 2006, vol. 38, No. 1, p. 53-58.

Ning et al., "Research on the Application of Neural Network to Diagnosis of Cardiopathy," Journal of Biomedical Engineering, (2004) Issue 2, pp. 284-287.

Office Action from corresponding Japanese Application No. 2016-191388 dated Oct. 3, 2017.

Ong, M.E.H. et al., "An Observational, Prospective Study Exploring the Use of Heart Rate Variability as a Predictor of Clinical Outcomes in Pre-Hospital Ambulance Patients", Resuscitation, Elseview, I.E., vol. 78, No. 3, Sep. 1, 2008, pp. 289-297.

Summons to Oral Proceedings communication from corresponding European Application No. 11713384.3 dated Nov. 10, 2017.

Young-Ho Lee et al., "A CAOPI System based on APACHE II for Predicting the Degree of Severity of Emergency Patients", In: Korea Society of Computer and Information, Jan. 2011, vol. 16, pp. 176-180.

Office Action from European Application No. 18193483.7 dated Oct. 21, 2021.

| Characteristics | (N=100) |
|---|---|
| Mean age (SD) | 65.21 (15.95) |
| Female (%) | 37 (37.00) |
| Ethnicity (%) | |
| Chinese | 73 (73.00) |
| Malay | 15 (15.00) |
| Indian | 7 (7.00) |
| Other | 5 (5.00) |
| Priority class (%) | |
| P1 | 87 (87.00) |
| p2 | 13 (13.00) |
| Vital Signs (SD) | |
| Temperature (°C) | 36.81 (0.75) |
| Resp rate (/min) | 19.47 (4.34) |
| Pulse (/min) | 91.82 (27.35) |
| SBP (mmHG) | 135.99 (37.80) |
| DBP (mmHG) | 75.94 (20.89) |
| $SpO_2$ | 95.19 (7.12) |
| GCS | 14.01 (2.77) |
| Pain Score | 1.84 (3.15) |
| Patient outcome (%) | |
| Died | 40 (40.00) |
| Survived | 60 (60.00) |
| ECG characteristics (SD) | |
| Mean length (min) | 207.52 (102.07) |
| % sinus rhythm | 89.64 (13.99) |

FIG. 11

| Heart Rate Variability Measures: | |
|---|---|
| — aRR: | 0.926 |
| — STD: | 0.048 |
| — Mean HR: | 64.963 |
| — SDHR: | 4.081 |
| — RMSSD: | 0.036 |
| — NN50: | 91 |
| — pNN50: | 1.662 |
| — HRV index: | 1.606 |
| — TINN: | 0.291 |
| — VLF: | 0.227 |
| — LF: | 0.048 |
| — HF: | 0.069 |
| — TP: | 0.344 |
| — LF norm: | 41.332 |
| — HF norm: | 58.668 |
| — LF/HF: | 0.705 |
| Prediction Results: | |
| — Cardiac Arrest Within 72h? | No |

2102

| Heart Rate Variability Measures: | |
|---|---|
| — aRR: | 0.514 |
| — STD: | 0.033 |
| — Mean HR: | 117.064 |
| — SDHR: | 6.415 |
| — RMSSD: | 0.036 |
| — NN50: | 307 |
| — pNN50: | 9.808 |
| — HRV index: | 1.405 |
| — TINN: | 0.044 |
| — VLF: | 0.124 |
| — LF: | 0.034 |
| — HF: | 0.224 |
| — TP: | 0.382 |
| — LF norm: | 13.146 |
| — HF norm: | 86.854 |
| — LF/HF: | 0.151 |
| Prediction Results: | |
| — Cardiac Arrest Within 72h? | Yes |

| Classifier | Activation/kernel function | Accuracy (%) | Sensitivity (%) | Specificity (%) |
|---|---|---|---|---|
| ELM | Hardlim | 61.44 | 41.20 | 74.93 |
| | Sigmoid | 62.72 | 42.20 | 75.33 |
| | Sine | 60.72 | 41.80 | 74.84 |
| SVM | RBF | 71.60 | 41.20 | 91.87 |
| | Linear | 69.76 | 46.60 | 85.20 |
| | Sigmoid | 71.68 | 39.40 | 93.20 |

FIG. 23

| Classifier | Activation/kernel function | Accuracy (%) | Sensitivity (%) | Specificity (%) |
|---|---|---|---|---|
| ELM | Hardlim | 65.76 | 51.27 | 72.13 |
| | Sigmoid | 67.60 | 53.23 | 72.53 |
| | Sine | 68.48 | 54.04 | 72.83 |
| SVM | RBF | 71.20 | 59.60 | 78.93 |
| | Linear | 71.04 | 58.00 | 79.73 |
| | Sigmoid | 66.08 | 48.80 | 77.60 |

FIG. 24

| Classifier | Activation/kernel function | Accuracy (%) | Sensitivity (%) | Specificity (%) |
|---|---|---|---|---|
| ELM | Hardlim | 68.48 | 51.07 | 76.71 |
| | Sigmoid | 72.40 | 53.47 | 78.42 |
| | Sine | 68.80 | 52.84 | 78.13 |
| SVM | RBF | 73.68 | 56.00 | 85.47 |
| | Linear | 78.32 | 65.00 | 87.20 |
| | Sigmoid | 71.04 | 47.00 | 88.40 |

FIG. 25

| Classifier | Activation/ kernel function | Number of Selected Segments | | | | |
|---|---|---|---|---|---|---|
| | | M' = 1 | M' = 3 | M' = 5 | M' = 7 | M' = 9 |
| ELM | Hardlim | 65.60 | 68.48 | 69.44 | 67.28 | 67.52 |
| | Sigmoid | 68.48 | 72.40 | 73.44 | 71.12 | 69.36 |
| | Sine | 64.96 | 68.80 | 68.24 | 67.36 | 65.84 |
| SVM | RBF | 73.04 | 73.68 | 72.40 | 73.28 | 70.96 |
| | Linear | 70.00 | 78.32 | 73.84 | 75.04 | 74.24 |
| | Sigmoid | 62.54 | 71.04 | 72.00 | 71.28 | 70.24 |

FIG. 26

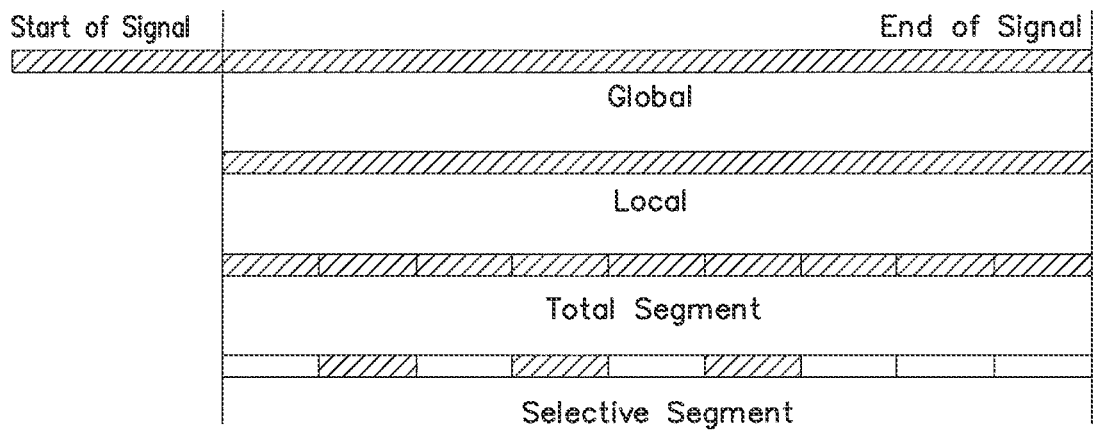

FIG. 27

Table 7 Classification accuracy with different predictive strategies using combined features.

| Classifier | Activation/ kernel function | Global (%) | Local (%) | Total segment (%) | Selective segment (%) |
|---|---|---|---|---|---|
| ELM | Hardlim | 60.48 | 60.96 | 67.52 | 68.48 |
| | Sigmoid | 64.24 | 65.28 | 69.36 | 72.40 |
| | Sine | 59.92 | 61.12 | 65.84 | 68.80 |
| SVM | RBF | 62.32 | 66.72 | 70.96 | 73.68 |
| | Linear | 70.00 | 68.64 | 74.24 | 78.32 |
| | Sigmoid | 60.64 | 60.72 | 70.24 | 71.04 |

FIG. 28

| Feature type | Activation function | Accuracy (%) | Sensitivity (%) | Specificity (%) | Training time (ms) | Testing time (ms) |
|---|---|---|---|---|---|---|
| Vital signs | Hardlim | 61.44 | 41.20 | 74.93 | 1.56 | 1.25 |
| | Sigmoid | 62.72 | 42.20 | 75.33 | 3.13 | 0.63 |
| | Sine | 60.72 | 41.80 | 74.84 | 2.50 | 0.94 |
| HRV | Hardlim | 61.60 | 44.44 | 72.40 | 8.13 | 0.63 |
| | Sigmoid | 61.36 | 46.27 | 71.40 | 8.13 | 1.25 |
| | Sine | 62.64 | 46.89 | 71.48 | 7.50 | 0.63 |
| Combined | Hardlim | 64.24 | 44.98 | 76.44 | 8.44 | 1.25 |
| | Sigmoid | 70.88 | 47.93 | 78.92 | 7.81 | 2.50 |
| | Sine | 65.92 | 47.82 | 78.09 | 7.50 | 1.25 |

FIG. 29

| Feature type | Activation function | Global (%) | Local (%) | Segment (%) |
|---|---|---|---|---|
| Combined | Hardlim | 60.48 | 60.96 | 64.24 |
|  | Sigmoid | 64.24 | 65.28 | 70.88 |
|  | Sine | 59.92 | 61.12 | 65.92 |

SYSTEM AND METHOD FOR PREDICTING ACUTE CARDIOPULMONARY EVENTS AND SURVIVABILITY OF A PATIENT

CROSS-REFERENCE TO RELATED APPLICATIONS

This application claims the benefit under 35 U.S.C. § 120 as a continuation of U.S. application Ser. No. 16/161,876 filed on Oct. 16, 2018 and titled SYSTEM AND METHOD FOR PREDICTING ACUTE CARDIOPULMONARY EVENTS AND SURVIVABILITY OF A PATIENT, which is incorporated herein by reference in its entirety. U.S. application Ser. No. 16/161,876 claims the benefit under 35 U.S.C. § 120 as a continuation of U.S. application Ser. No. 15/709,608 filed on Sep. 20, 2017 and titled SYSTEM AND METHOD FOR PREDICTING ACUTE CARDIOPULMONARY EVENTS AND SURVIVABILITY OF A PATIENT, now U.S. Pat. No. 10,136,861, which is incorporated herein by reference in its entirety. U.S. application Ser. No. 15/709,608 claims the benefit under 35 U.S.C. § 120 as a continuation of U.S. application Ser. No. 15/227,212 filed on Aug. 3, 2016 and titled SYSTEM AND METHOD FOR PREDICTING ACUTE CARDIOPULMONARY EVENTS AND SURVIVABILITY OF A PATIENT, now U.S. Pat. No. 9,795,342, which is incorporated herein by reference in its entirety. U.S. application Ser. No. 15/227,212 claims the benefit under 35 U.S.C. § 120 as a continuation of U.S. application Ser. No. 14/616,057 filed on Feb. 6, 2015 and titled SYSTEM AND METHOD FOR PREDICTING ACUTE CARDIOPULMONARY EVENTS AND SURVIVABILITY OF A PATIENT, now U.S. Pat. No. 9,420,957, which is incorporated herein by reference in its entirety. U.S. application Ser. No. 14/616,057 claims the benefit under 35 U.S.C. § 120 as a continuation of U.S. application Ser. No. 14/199,495 filed on Mar. 6, 2014 and titled METHOD OF PREDICTING ACUTE CARDIOPULMONARY EVENTS AND SURVIVABILITY OF A PATIENT, now U.S. Pat. No. 8,951,193, which is incorporated herein by reference in its entirety. U.S. application Ser. No. 14/199,495 claims the benefit under 35 U.S.C. § 121 as a division of U.S. application Ser. No. 13/868,605 filed on Apr. 23, 2013 and titled METHOD OF PREDICTING ACUTE CARDIOPULMONARY EVENTS AND SURVIVABILITY OF A PATIENT, now U.S. Pat. No. 8,668,644, which is incorporated herein by reference in its entirety. U.S. application Ser. No. 13/868,605 claims the benefit under 35 U.S.C. § 120 as a continuation of U.S. application Ser. No. 13/047,348 filed on Mar. 14, 2011 and titled METHOD OF PREDICTING ACUTE CARDIOPULMONARY EVENTS AND SURVIVABILITY OF A PATIENT, now abandoned, which is incorporated herein by reference in its entirety. U.S. application Ser. No. 13/047,348 claims priority under 35 U.S.C. § 119(e) to U.S. Provisional Application Ser. No. 61/313,822 filed on Mar. 15, 2010.

FIELD OF THE INVENTION

The invention relates to a method of predicting acute cardiopulmonary (ACP) events and survivability of a patient. The invention also relates to a system for predicting acute cardiopulmonary events and survivability of a patient.

BACKGROUND OF THE INVENTION

Triage is an important part of any Emergency Medical Response. This is the clinical process of rapidly screening large numbers of patients to assess severity and assign appropriate priority of treatment. Triage is a reality as medical resources are never enough for all patients to be attended instantaneously. It is thus important to be able to quickly identify patients of higher severity, who would need such resources more urgently. Therefore, a device for automatic patient outcome (cardiac arrest and mortality) analysis could be helpful to conduct triage, especially in disaster or mass casualty situations, where demand overwhelms resources.

Current triage systems are based on clinical judgment, traditional vital signs and other physiological parameters. They tend to be subjective, and are not so convenient and efficient for clinicians. Moreover, the clinical 'vital signs' including heart rate, respiratory rate, blood pressure, temperature and pulse oximetry have not been shown to correlate well with short or long-term clinical outcomes.

SUMMARY OF THE INVENTION

According to embodiments of the invention, there is provided a method of producing an artificial neural network capable of predicting ACP events and the survivability of a patient, the method including: storing in an electronic database patient health data, the patient health data comprising a plurality of sets of data, each set having at least one of a first parameter relating to heart rate variability data and a second parameter relating to vital sign data, each set further having a third parameter relating to patient survivability; providing a network of nodes interconnected to form an artificial neural network, the nodes comprising a plurality of artificial neurons, each artificial neuron having at least one input with an associated weight; and training the artificial neural network using the patient health data such that the associated weight of the at least one input of each artificial neuron of the plurality of artificial neurons is adjusted in response to respective first, second and third parameters of different sets of data from the patient health data, such that the artificial neural network is trained to produce a prediction on the ACP events and survivability of a patient.

According to embodiments of the invention, there is provided a method of predicting the ACP events and survivability of a patient, the method including: measuring a first set of parameters relating to heart rate variability data of a patient; measuring a second set of parameters relating to vital sign data of the patient; providing an artificial neural network comprising a network of interconnected nodes, the nodes comprising a plurality of artificial neurons, each artificial neuron having at least one input with an associated weight adjusted by training the artificial neural network using an electronic database having a plurality of sets of data, each set having at least a parameter relating to heart rate variability data and a parameter relating to vital sign data, each set further having a parameter relating to patient survivability; processing the first set of parameters and the second set of parameters to produce processed data suitable for input into the artificial neural network; providing the processed data as input into the artificial neural network; and obtaining an output from the artificial neural network, the output providing a prediction on the ACP events and survivability of the patient.

According to embodiments of the invention, there is provided a patient ACP events and survivability prediction system including: a first input to receive a first set of parameters relating to heart rate variability data of a patient; a second input to receive a second set of parameters relating to vital sign data of the patient; a memory module storing instructions to implement an artificial neural network comprising a network of interconnected nodes, the nodes comprising a plurality of artificial neurons, each artificial neuron having at least one input with an associated weight adjusted by training the artificial neural network using an electronic database having a plurality of sets of data, each set having at least a parameter relating to heart rate variability data and a parameter relating to vital sign data, each set further having a parameter relating to patient survivability; a processor to execute the instructions stored in the memory module to perform the functions of the artificial neural network and output a prediction on the ACP events and survivability of the patient based on the first set of parameters and the second set of parameters; and a display for displaying the prediction on the ACP events and survivability of the patient.

According to embodiments of the invention, there is provided a method of predicting the ACP events and survivability of a patient, the method including: measuring a first set of parameters relating to heart rate variability data of a patient; measuring a second set of parameters relating to vital sign data of the patient; obtaining a third set of parameters relating to patient characteristics; providing the first set of parameters, the second set of parameters and the third set of parameters as sets of normalized data values, where required, to a scoring model implemented in an electronic database, the scoring model having a respective category associated to each parameter of the first set of parameters, the second set of parameters and the third set of parameters, each category having a plurality of pre-defined value ranges, each of the plurality of value ranges having a pre-defined score; determining a score for each parameter of the first set of parameters, the second set of parameters and the third set of parameters by assigning the sets of normalized data to respective pre-defined value ranges, encompassing the sets of normalized data values, of the plurality of value ranges of the category associated to the respective parameter of the first set of parameters, the second set of parameters and the third set of parameters; obtaining a total score, being a summation of the score for each parameter of the first set of parameters, the second set of parameters and the third set of parameters, the total score providing an indication on the ACP events and survivability of the patient.

According to aspects of embodiments, a system for the detection of impending acute cardiopulmonary medical events that, left untreated, would with a reasonable likelihood result in either severe injury or death includes: an electro-cardiogram (ECG) module including a plurality of electrodes for sensing a patient's ECG and having an ECG output; a sensor for sensing a patient's physiologic parameter other than ECG; a first input for receiving the ECG output; a second input for receiving signals from the sensor for sensing a patient's physiologic parameter other than ECG; a third input constructed and arranged to receive: parametric information describing at least one element of a patient's demographic information; and parametric information describing a patient's medical history; a digitizing unit for digitizing the ECG and the physiologic signal other than ECG; a housing containing a memory unit and processing unit, for storing and processing, respectively, the ECG, the physiologic signal other than ECG, patient demographic information and medical history; and a user communication unit; wherein the processing unit calculates at least one measure of heart rate variability (HRV), combines that at least one measure of HRV with at least one parameter each of patient demographic information and medical history, and calculates a statistical probability of an ACP event within 72 hours of the calculation. The system may further be constructed and arranged to be carried by the patient in a wearable configuration. The sensor may measure the perfusion status of the microvasculature. The sensor may be a pulse oximeter. The system may further include: an electromagnetic stimulator of physiologic tissue, which may stimulate cardiac tissue. The user communication unit may have key entry. The third input may be a key entry. The user communication unit may be in the main housing. The user communication unit may be separate from the main housing. The user communication unit may be a display. The stimulation may be pacing or the stimulation may be defibrillation. The stimulation may be magnetic stimulation.

According to aspects of embodiments, a system for predicting mortality of a patient being treated for trauma or as part of a mass casualty occurrence, includes: an electro-cardiogram (ECG) module including a plurality of electrodes for sensing a patient's ECG and having an ECG output; a sensor for sensing a patient's physiologic parameter other than ECG; a first input for receiving the ECG output; a second input for receiving signals from the sensor for sensing a patient's physiologic parameter other than ECG; a third input constructed and arranged to receive: parametric information describing at least one element of a patient's demographic information; and parametric information describing a patient's medical history; a digitizing unit for digitizing the ECG and the physiologic signal other than ECG; a housing containing a memory unit and processing unit, for storing and processing, respectively, the ECG, the physiologic signal other than ECG, patient demographic information and medical history; and a user communication unit; wherein the processing unit calculates at least one measure of heart rate variability (HRV), combines that at least one measure of HRV with at least one parameter each of patient demographic information and medical history, and calculates a statistical probability of mortality for the patient. The system may be constructed and arranged to be carried by the patient in a wearable configuration. The sensor may measure the perfusion status of the microvasculature. The sensor may be a pulse oximeter.

According to aspects of embodiments of the invention, a method of treating a cardiac condition of a patient, includes: measuring heart rate variability (HRV) of the patient; measuring vital sign data of the patient; predicting, using a computing apparatus constructed and arranged for the purpose, a likelihood of survival of the patient to one or more selected time limits based on HRV in combination with the measured vital sign data; and treating the cardiac condition as indicated by the vital sign data when the likelihood of survival of the patient to one or more selected time limits is below a desired threshold. The method may further include: collecting at least one of patient demographic information and patient history information; wherein predicting further comprises: computing the likelihood of survival additionally in view of the collected patient demographic information and patient history information. The method may yet further include: selecting a time limit of between 4 and 24 hours or a time limit of between 4 and 72 hours.

According to aspects of embodiments of the invention, an apparatus for predicting a likelihood of survival of a patient to one or more selected time limits due to cardiac causes, includes: a heart rate sensor having a heart rate output; a vital sign sensor having a vital sign output; a computational module receiving the heart rate output and the vital sign output, and performing: computing heart rate variability (HRV) from the heart rate output received; and computing the likelihood of survival of the patient to the one or more selected time limits due to cardiac causes, from a combination of the HRV computed and the vital sign output; and, an output device displaying to a user the likelihood of survival of the patient to the one or more selected time limits due to cardiac causes. The apparatus may further include: a data input device constructed and arranged to collect at least one of patient demographic information and patient history information; and computing the likelihood of survival additionally in view of the collected patient demographic information and patient history information. The apparatus may yet further include: a time limit of between 4 and 24 hours or a time limit of between 4 and 72 hours.

The invention will be further illustrated in the following description, with reference to the drawings.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 11 summarizes raw ECG data characteristics of patients.

FIGS. 18 to 20 show snap shots of the output of a patient ACP events and survivability prediction system in accordance with embodiments of the invention.

FIGS. 23, 24 and 25 respectively show classification results using vital signs, HRV measures, and combined features.

FIG. 26 shows results from using a different number of selected segments using combined features.

FIG. 27 shows four different predictive strategies.

FIG. 28 shows results from different predictive strategies using combined features.

FIG. 29 shows classification results from using vital signs, HRV measures, and combined features.

DETAILED DESCRIPTION

Figure 1:
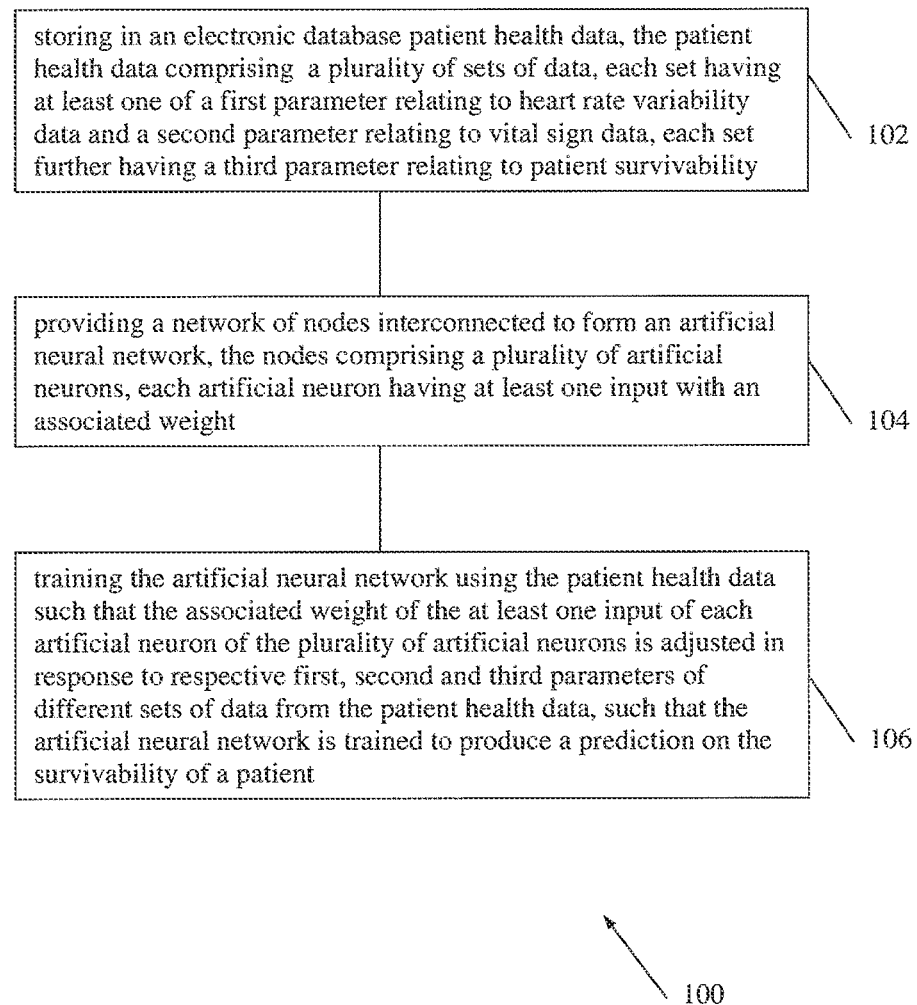
FIG. 1 is a flow chart illustrating a method, according to one embodiment of the present invention, used to produce an artificial neural network capable of predicting the ACP events and survivability of a patient.

According to aspects of embodiments, a system is able to reliably predict acute cardiopulmonary medical events that, left untreated, would with a high likelihood result in either severe injury or death. Examples of such acute cardiopulmonary (ACP) events would include cardiac or respiratory arrest, hypovolemic shock particularly due to blunt trauma injury or acute decompensated heart failure.

Previous systems seeking to determine and predict patient morbidity and patient mortality under various trauma, stress, and shock conditions have included in the battery of signs monitored, heart rate variability (HRV). HRV measurement quantifies the variability over time of the R-R interval in the electrocardiographic signal of the patient. The R-wave of a particular heartbeat corresponds to the point in the cardiac cycle of the early systolic phase, and from a signal processing point of view, provides a reliable time-fiducial for making cardiac cycle interval measurements. HRV is affected by the autonomic nervous system, which consists of the sympathetic nervous system (SNS) and the parasympathetic nervous system (PNS). Observed HRV is believed to be an indicator of the dynamic interaction and balance between the SNS and PNS, providing a measure of nervous system competence. HRV serves as an indicator for the diagnosis and assessment of a variety of conditions that are affected by the autonomic system ranging from congestive heart failure to sleep apnea. For example, decreased HRV has been found to be a predictor of increased mortality in the elderly for coronary heart disease. Decreased HRV is also seen after sudden cardiac arrest and in patients with diseases such as diabetes, uremia and hypertension. Unfortunately, heart rate variability alone, while being able to predict increased mortality, is only a poor predictor of ACP events with any time specificity.

A variability measure related to HRV is T-wave alternans which is a measure of the variation in the recovery of the myocardium during the diastolic (relaxation) phase, and measures the fluctuations in the amplitude of the T-wave of the ECG. Because of the need to measure minute fluctuations in ECG amplitude, it is relatively susceptible to patient motion-induced artifacts and so not useful for continuous monitoring of a patient's ECG.

In accordance with aspects of embodiments, for example in triage systems, it would be of value to be able to reliably predict acute cardiopulmonary medical events that, left untreated, would with a high likelihood result in either severe injury or death. Examples of such acute cardiopulmonary (ACP) events would include cardiac or respiratory arrest, hypovolemic shock particularly due to blunt trauma injury or acute decompensated heart failure. Conventional clinical signs, symptoms and physiologic measurements provide little warning for these types of events. For instance, implantable cardioverter defibrillators (ICDs) or wearable external defibrillators such as the Lifevest (ZOLL Medical) will continuously analyze the patient's electrocardiographic (ECG) signal during their daily activities and deliver a life-saving electrical shock to the heart.

In U.S. Application 2009/0234410A1, a system is described for the prediction of heart failure decompensation. This, and similar, systems require the detection of a cardiac arrhythmia via the ECG, which unfortunately limits the duration of predictive forecast accuracy. For instance, arrhythmia detectors on ICDs and wearable defibrillators only detect a shockable event after the patient is in a lethal arrhythmia requiring a shock. Despite extensive research, utilizing arrhythmia analysis for the reliable prediction of impending ACP events has been problematic, lacking in both predictive accuracy as well as event time specificity (prediction of when the event might occur). U.S. 2009/0234410 may utilize heart rate variability in conjunction with the arrhythmia analysis, but again, the use of the arrhythmia detector will limit the predictive accuracy.

More sophisticated analytic methods of cardiac arrhythmias such as T-wave alternans also require very accurate measurement of ECG voltages to better than 1 microvolt typically and thus tend to be very susceptible to signal artifact generated in systems where the ECG is monitored on a relatively continuous basis such as a wearable monitoring and therapeutic device. U.S. Pat. No. 4,957,115 describes a system using ECG arrhythmia analysis along with other physiological measurements to generate a probability score of impending death due to a cardiovascular event. Other systems, such as that described in U.S. Pat. No. 7,272,435, might be used in a stress test laboratory where patients are viewed under controlled conditions unlike those conditions that would likely be encountered on a wearable device. Under such strictly controlled conditions, noise-susceptible measurement techniques such as T-wave alternans might be applicable.

U.S. Pat. Nos. 6,665,559 and 5,501,229 describe systems that determine a probability of cardiovascular risk based on serial comparisons of ECG arrhythmia analysis. It would thus be advantageous, according to aspects of embodiments of the invention, to have a system that is both more robust in the presence of ECG signal artifacts often encountered during continuous monitoring from an external wearable device, and further advantageous to have a system that is able to predict with some reliability when an ACP event is most likely to occur.

Aspects of embodiments of the invention combine HRV with other vital sign data, as distinct from US Published Patent Application 2007/112,275 A1, which describes a system which alerts a user on any vital sign going out of a desired range. Further, aspects of embodiments of the invention predict the likelihood of occurrence of acute cardiopulmonary (ACP) events by combining HRV with other vital sign data, as compared with US Published Patent Application 2007/276,275 A1, which describes predicting morbidity and mortality due to an entirely different and unrelated type of injury, traumatic brain injury, using HRV combined with one or more other vital signs.

Measurements of HRV data according to aspects of embodiments provide a measure of the interaction between the autonomic nervous system and the cardiovascular system. While HRV has become a well-known technique used by researchers in attempts to predict ACP events (See for instance, Insights from the Study of Heart Rate Variability, P. K. Stein, R. E. Kleiger, Annu. Rev. Med. 1999. 50:249-61), as Stein et al. point out, HRV alone is insufficient to predict, with any reasonable degree of accuracy, future clinical events.

Aspects of embodiments of the invention differ from commercial devices for HRV analysis currently available in the market in yet other ways. Some commercial HRV analysis devices are bulky. Aspects of embodiments are more portable and therefore field ready, so as to be convenient for routine use in hospitals and for outfield environments such as ambulances. Moreover, aspects of embodiments do more than simply correlate some HRV measures with particular abnormalities of cardiovascular system, as commercial devices currently do. Aspects of embodiments, in a portable package, predict risk scores for patient outcomes. Some commercial devices are portable but have limited functions. Experienced clinicians interpret the outputs and some current commercial devices only provide simple information such as the health condition of a normal person. Aspects of some embodiments thus also improve upon existing commercial devices, which lack the combination of portability and ability of automatically predicting patient outcomes that is crucial to triage.

Figures 33, 34:
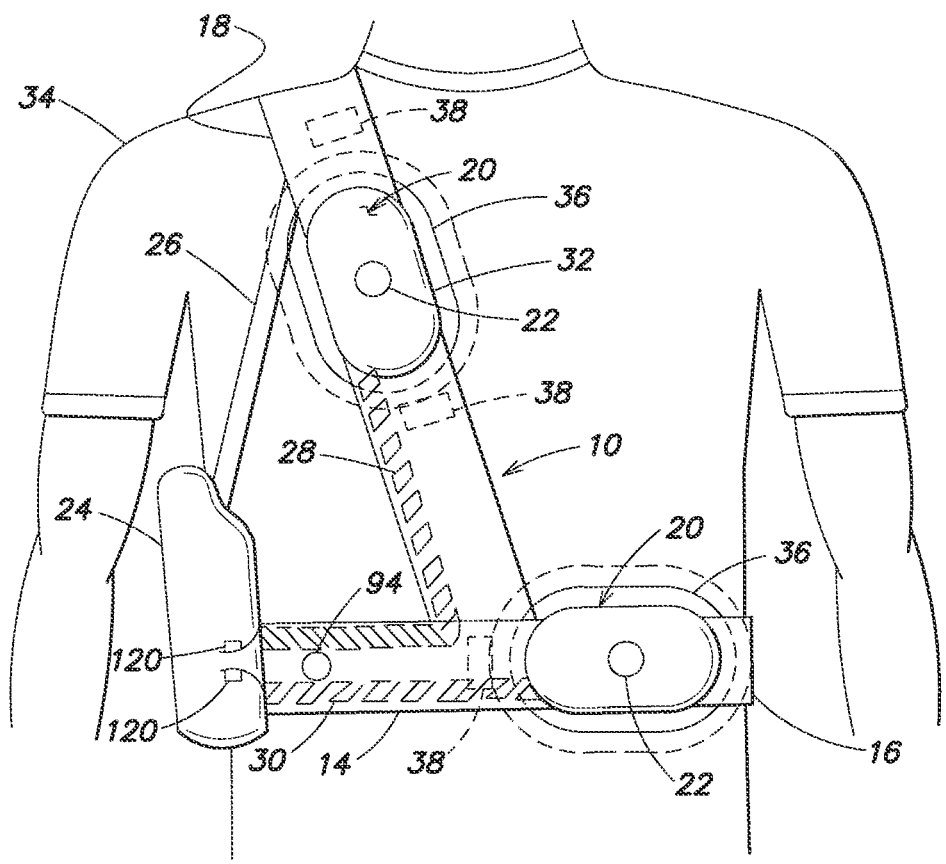
FIG. 33 shows results from different predictive strategies using combined features.
FIG. 34 shows an embodiment of the invention in a wearable medical device.

In one embodiment of the invention, there is provided a patient-wearable device such as device 10, shown in overall view in FIG. 34. The patient-worn device may include a waist-encompassing belt 14 of suitable fabric, webbing or the like, and may incorporate sprung elements the belt having a low-profile connector or buckle 16 and a shoulder strap 18 of like material connected between front and rear portions of the belt. First and second sensing and pulse electrode assemblies 20 are carried respectively on belt 14 and shoulder strap 18. Belt 14 also carries an electronics housing 24 which may have a supporting strap connection 26 with strap 18 and electrical conductors, diagrammatically indicated at 28 and 30, for receiving electrical signals from and delivering electrical pulses to the respective electrode assemblies 20. Assemblies 20 have respective sensing electrodes 22 and pulse electrodes 32.

In use of the device as thus far described, assemblies 20 are held in comfortable contact with a patient's chest wall and continuously monitor and detect the heart rhythm by means of the respective sensing electrodes 22. Alternatively, sensing electrodes may be traditional disposable ECG electrodes placed on the patient's skin in a location separate from the pulse electrodes 32. Device 10 may be worn over a comfortable undergarment 34, such as a T-shirt, which may have apertures 36 that receive the respective electrode assemblies 20. Attachments 38, such as patches of loop and pile Velcro-type fabric, may be provided between belt 14, strap 18 and the undergarment.

The housing for the electrode assemblies 20 may contain signal conditioning and amplification electronics for the EGG electrode. The EGG electrode 22 may be capacitive, conductive carbon, or any other design that permits long-term use without skin irritation. It is understood that the printed circuits of the respective electrodes are connected to the pulse generator 24 through conductors 28 and 30.

A sensor for measuring a second physiologic parameter such as a pulse oximeter 38 is used to measure additional physiologic status of the patient. In the case of the pulse oximeter the physiologic parameter is that of tissue perfusion.

The sensor might also be impedance plethysmography (IP), known to those skilled in the art. IP is accomplished by measuring small variations in the electrical impedance of the tissue underlying the sense electrodes, typically by applying a small current to the electrodes and measuring the induced voltage. As the volume of the tissue changes, as a result of physiological activity such as blood perfusion or as increased air in the lungs with respiration, its electrical impedance also changes. Thus the physiologic parameter sensed can be both blood flow and respiration simultaneously via the same set of impedance electrodes. It is also possible, and known to those skilled in the art that the ECG electrodes 22 can also be used for both impedance measurements as well as ECG simultaneously as the impressed current for IP is typically at 30 kHz or higher and thus can be filtered from the input signal to the ECG amplifiers prior to processing, since ECG signals contain relevant frequencies no higher than 100 Hz. More than one sensor may be provided to obtain multiple measures for two or more physiological parameters.

The ECG signal may be detected using passive devices such as an electrode making an electrical contact, using sticky pads, pastes or gel with the at least one patient's skin surface. Other means such as an active device, which need not necessarily contact the at least one patient's skin surface to detect the patient's ECG signal, may be used. Such an active device may be an insulated bioelectrode (IBE). The IBE may measure the electric potential on the skin without resistive electrical contact and with very low capacitive coupling. The IBE may be connected, wirelessly or via cable, to a processing unit. To achieve a wireless IBE, a wireless node platform may be integrated into the IBE. An example of a system that may function with a wireless IBE is the "Tmote Sky" platform, using three wireless IBEs to form a 3-lead system. The "Tmote Sky" platform has an 802.15.4 radio interface at 250 Kbps and is controlled by the MSP430F1611 microcontroller.

Figure 4:
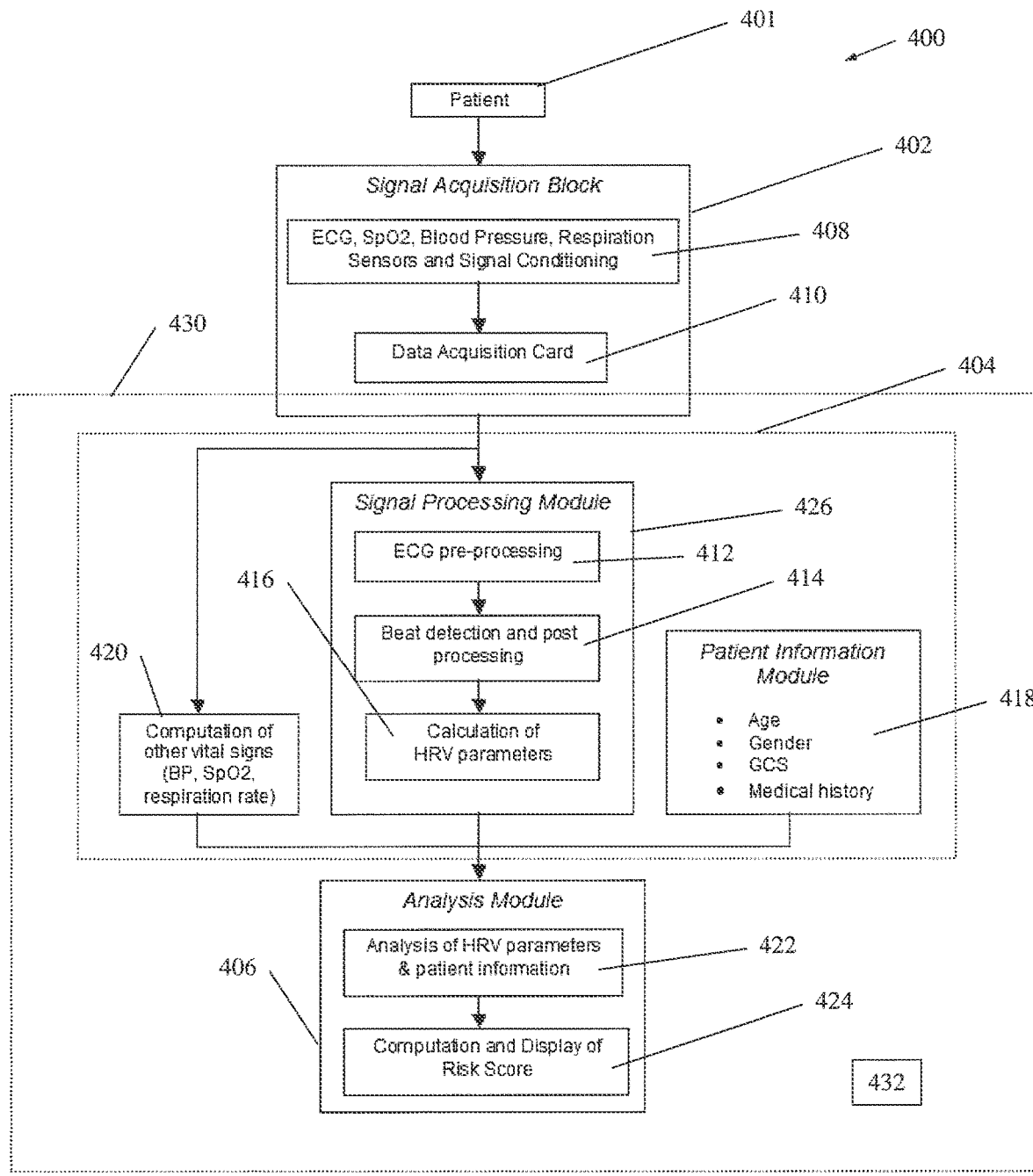
FIG. 4 shows a block diagram of a system used to predict the ACP events and survivability of a patient.

Referring to FIG. 4, the system 400 has three main functional blocks: a signal acquisition block 402, a signal processing block 404 and an analysis block 406. The signal acquisition block 402 has sensor and signal conditioning hardware 408 for acquiring an ECG signal and other vital signs from a patient 401. The sensor and signal conditioning hardware 408 may include sensors that detect ECG signals, and other physiological parameters such as blood pressure, tissue perfusion such as SpO2 and respiration rate.

The signal acquisition block 402 has a data acquisition (DAQ) electronics 410, which in one embodiment contains the signal conditioning circuits used for processing output from the sensor and signal conditioning hardware 408. The signal conditioning circuits are designed to process signals from these sensors. The signal conditioning circuits comprise electronic components that perform functions such as isolation and amplification of the various signals measured by the sensors as well as conversion of the analog signals to digital signals. The DAQ electronics 410 communicate the digitized ECG and other physiological parameters to the processing unit 430. The processing unit contains circuit elements known to those skilled in the art: a processing unit such as a microprocessor; a program storage circuit such as a disk drive or solid state storage element such as a ROM or Flash memory; a dynamic data storage element such as DRAM; a communication circuit such as a serial data channel, Bluetooth, USB, etc. for communicating with both the DAQ 410 and external devices such as a WiFi network or cellular network; a user interface circuit containing a display, audio channel and speaker, a touchscreen interface and switches; a battery and power supply circuit. An input panel also accepts additional information such as age and gender of the patient 401.

The signal processing block 404 includes a signal processing module 426, a vital sign module 420 and a patient information module 418. The circuitry may be configured in such a way as to optimize functions, with the Signal Processing Module 426 and Analysis Module 406 functions being provided by a digital signal processor (DSP) chip such as the Texas Instruments Blackfin processor family, and the user interface and other functions being provided by a general purpose microprocessor such as Dual-Core Intel Xeon Processor running a Linux operating system. By the word "module", we refer only to the particular functions performed by the processing unit 430; the module boundary in the figure may or may not correspond to actual circuitry. The signal processing module 426 includes an ECG pre-processing module 412, a beat detection and post processing module 414, and a HRV parameter calculation module 416. The ECG pre-processing module 412 processes raw ECG data from the signal acquisition block 402 to suppress unwanted signals such as noise, motion artifacts and power line interference which may affect the accuracy of HRV parameters eventually extracted from the ECG data. The beat detection and post processing module 414 acts on de-noised signal from the ECG pre-processing module 412 to detect a heartbeat and to exclude non-sinus beats during post-processing. The duration between consecutive sinus beats are compiled into an RRI (beat to beat interval) sequence from which HRV parameters are computed. Extraction is preferably from an ECG signal derived from the patient's sinus rhythm.

In one embodiment of the present invention, extracting the heart rate variability data comprises filtering the ECG signal to remove noise and artifacts; locating a QRS complex within the filtered ECG signal; finding a RR interval between successive R waves of the QRS complex; and processing the sequence of information within the RR interval to obtain the heart rate variability data.

In one embodiment of the present invention, a band pass filter is used to filter the ECG signal and locate the QRS complex. A band pass filter with an operating frequency range wider than the frequency components of the QRS complex has to be used. The frequency components of the QRS complex lie between 10 to 25 Hz. Thus, in one embodiment of the present invention, the operation frequency range of the band pass filter is between about 5 Hz to about 28 Hz.

In one embodiment of the present invention, the R wave may be located as follows. A maximum peak data value first occurring in the filtered ECG signal is located. An upper amplitude threshold and a lower amplitude threshold from the located maximum peak value are determined. A peak value and minimum values on either side of the peak value are located. In this embodiment of the invention, either side refers to the left and right sides of the peak value. The conditions of whether the peak value is above the upper amplitude threshold, while the minimum values are below the lower amplitude threshold are met is checked. If the conditions are met, the location of the peak value is denoted as an R position. The location of the minimum value occurring closest on the left side of the R position is denoted as a Q position, and the location of the minimum value occurring closest on the right hand side of the R position is denoted as an S position. With reference to a time scale that the filtered ECG signal is plotted against, the Q position occurs at where the minimum value first occurs before the R position, while the S position occurs at where the minimum value first occurs after the R position. The location of a QRS peak within the filtered ECG signal is thus determined.

In one embodiment of the present invention, where a 1D array of ECG sample points x(n) are provided, the upper and lower amplitude thresholds ($T_{upper}$ and $T_{lower}$) are set after finding the maximum value (ref_peak) within the first few seconds of data. The thresholds are defined as:

$$T_{upper} = \text{ref\_peak} + 0.4 * \text{ref\_peak}$$

$$T_{lower} = \text{ref\_peak} - 0.35 * \text{ref\_peak}$$

Then an R wave is said to occur at the point i if the following conditions are met, $x(i)$ lies between $T_{upper}$ and $T_{lower}$;

$x(i+1) - x(i) < 0$; and $x(i) - x(i-1) > 0$;

where the R-peak is the point with maximum value.

The positions of other R waves within the filtered ECG signal may be located by iterating the process of: locating another peak value and locating other minimum values on either side of the another peak value. When the another peak value is above the upper amplitude threshold while the other minimum values are both below the lower threshold, the location of the peak value is denoted as an R position. The location of the minimum value occurring closest on the left side of the R position is denoted as a Q position and the location of the minimum value occurring closest on the right side of the R position is denoted as an S position. In this manner, the location of another QRS peak is determined.

Processing the sequence of information within the RR interval may further comprise removing outliers from the sequence of information within the RR interval. A median value and a standard deviation value for the RR interval may be found. A tolerance factor based on the standard deviation value may be calculated. A portion of information that lies within the RR interval spanning either side of the median value by the tolerance factor may be retained. Heart rate variability data may be obtained from the retained portion of information and the remaining portion of the information from the sequence of information may be discarded.

In embodiments of the invention, the heart rate variability data may include time domain data, frequency domain data and geometric domain data.

The time domain data may include information on any one or more of the following parameters: mean of RR intervals (mean RR), standard deviation of RR intervals (STD), mean of the instantaneous heart rate (mean HR), standard deviation of the instantaneous heart rate (STD_HR), root mean square of differences between adjacent RR intervals (RMSSD), number of consecutive RR intervals differing by more than 50 ms (NN50), and percentage of consecutive RR intervals differing by more than 50 ms (pNN50).

The frequency domain data may include information on any one or more of the following parameters: power in very low frequency range (<=0.04 Hz) (VLF), power in low frequency range (0.04 to 0.15 Hz) (LF), power in high frequency range (0.15 to 0.4 Hz) (HF), total power which is estimated from the variance of NN intervals in the segment and is measured in $ms^2$ (TP), ratio of LF power to HF power (LF/HF), LF power in normalized units: LF/(TP−VLF)×100 (LFnorm), and HF power in normalized units: HF/(TP−VLF)×100 (HFnorm).

The geometric domain data may include information on any one of the following data: total number of all RR intervals divided by height of histogram of intervals (HRV Index) and base width of triangle fit into RR histogram using least squares method (TINN).

In embodiments of the invention, the vital sign data may include any one or more of the following: systolic blood pressure, diastolic blood pressure, pulse rate, pulse oximetry, respiratory rate, glasgow coma scale (GCS), pain score, temperature. The vital sign measurement may be either a continuous variable in the form of a waveform. The vital sign measurement may also be a measurement taken at a single point in time, or the vital sign measurement may be a series of measurements, typically sampled at regular intervals that may sometimes be stored in the form of so-called trend data.

In embodiments of the invention, the patient health data used to train the artificial neural network may be standard deviation of the instantaneous heart rate (STD_HR), power in low frequency range (0.04 to 0.15 Hz) in normalized units (LFnorm), age, pulse rate, pulse oximetry, systolic blood pressure and diastolic blood pressure.

In embodiments of the invention, the measured first set of parameters are standard deviation of the instantaneous heart rate (STD_HR) and power in low frequency range (0.04 to 0.15 Hz) in normalized units (LFnorm); and the measured second set of parameters are age, pulse rate, pulse oximetry, systolic blood pressure and diastolic blood pressure.

The patient health data includes parameters relating to heart rate variability data, vital sign data, patient survivability and patient characteristics. The patient health data may include a plurality of sets of data, where each set of data may be formed from a single category of these parameters, i.e. either the first parameter relating to heart rate variability, the second parameter relating to vital sign data, the third parameter relating to patient characteristics or a fourth parameter relating to patient survivability. On the other hand, each set of data may have a combination of categories of these parameters, such as at least one of the first parameter relating to heart rate variability, the second parameter relating to vital sign data and the third parameter relating to patient characteristics such as age, gender, or other demographic characteristic, as well as specific conditions in the patient's health history such as diabetes, myocardial infarction, high blood pressure. Severity of the specific condition is also recorded and provided to the system, such as the date of occurrence of the myocardial infarction, the post-infarction ejection fraction or the percentage extent of the ventricular tissue damage. Other descriptors may be the specific medications that a patient uses to treat various medical conditions. A fourth parameter may be provided relating to patient survivability such as an outcome like survival to hospital discharge. The fourth parameter is used as a means of training the algorithm during the training phase of algorithm development and during use as a means of improving the accuracy by recording the predictive algorithm's actual accuracy and making suitable modifications to improve that accuracy. The set of data may not even necessarily include the parameter relating to patient survivability. Alternatively, each set of patient health data may include all four parameters. It will thus be appreciated that within the patient health data, one set of data may not contain the same number of parameters compared to another set of data. Further, the patient health data is stored as digital data converted from the form in which each of the four parameters is originally obtained (such as an analog signal), whereby the original form of the obtained measurements.

Data for patient characteristics such as demographics, health history and survivability may be communicated to the device 10 or system 400 via a wireless network distributed through a hospital, such as 802.11.

According to embodiments of the present invention, a method of producing an artificial neural network capable of predicting the survivability of a patient is provided. The method includes storing patient health data in an electronic database. The patient health data includes a plurality of sets of data, each set having at least one of a first parameter relating to heart rate variability data and a second parameter relating to vital sign data. Each of the plurality of sets of data further has a third parameter relating to patient survivability. A network of nodes interconnected to form an artificial neural network is provided. The nodes include a plurality of artificial neurons, each artificial neuron having at least one input with an associated weight. The artificial neural network is trained using the patient health data such that the associated weight of the at least one input of each artificial neuron of the plurality of artificial neurons is adjusted in response to respective first, second and third parameters of different sets of data from the patient health data. This results in the artificial neural network being trained to produce a prediction on the survivability of a patient.

The electronic database used to store patient health data may be a memory module such as a hard disk drive, an optical disc, or solid state devices (for example thumb drives). During the training phase of the algorithm, the patient health data may be obtained from hospital records or from conducting field studies of a pool of patient(s), where the pool includes a group of patients acting as a control group. Thus, the patient health data may include data of patients suffering from various ailments, patients who are healthy (i.e. having no symptoms of illnesses), patients of various race and age and/or patients who are terminally ill.

It was earlier mentioned that vital sign data may be one of the parameters (referred to as the second parameter in the plurality of sets of data related to patient health) used to train the artificial neural network that can be used to implement a clinical decision support program or device.

Vital sign data is defined as clinical measurements that indicate the state of a patient's essential body functions. These measurements relate to systolic blood pressure, diastolic blood pressure, pulse rate, pulse oximetry, respiratory rate, glasgow coma scale (GCS), pain score and temperature.

Training phase vital sign data may be obtained from hospital records or from conducting field studies of a pool of patient(s). When conducting field studies, each vital sign may be measured as follows. For example, systolic blood pressure and diastolic blood pressure may be measured using a blood pressure measurement device such as the "statMAP™ Model 7200" from "CardioCommand". Alternatively, devices such as a sphygmomanometer or a mercury manometer may be used. Pulse rate, pulse oximetry and respiratory rate may be measured using a pneumogram. Glasgow coma scale (GCS) refers to the degree of spontaneity of the patient's physical (such as limbs, eyes) motor and/or verbal response to instructions from a medical professional. Pain score refers to the degree of response (such as adduction, pronation or extension of a limb or body part; flexion or withdrawal) to pain applied to the patient. Temperature may be recorded using a thermometer.

Turning to another parameter that may be used to train the artificial neural network, patient survivability (referred to as the third parameter in the plurality of sets of data related to patient health) refers to the outcome, i.e. either death or survival, of a patient. Thus, data on the patient survivability is typically associated with a respective set of both heart rate variability data and vital sign data for the same patient.

Another parameter that may be used to train the artificial neural network is patient characteristics. Patient characteristics include information such as patient age, gender and medical history. At the conclusion of the training phase, the parameters found to be most relevant to achieving a high level of accuracy will then be used as inputs to the real time detection system.

An electronic device may incorporate a processor or memory module storing instructions to implement the trained artificial neural network, so that the device can analyse health data of a patient being examined. The output of the electronic device can then be used to assist an operator or a medical professional to predict the outcome of the patient and thereby make appropriate clinical decisions on how to treat the patient.

In embodiments of the invention, the artificial neural network (ANN) may be a mathematical model or computational model simulating the structure and/or functional aspects of a biological neural network. In embodiments of the invention, the nodes of the ANN include at least one input (being the at least one actual input of the ANN), at least one artificial neuron and at least one output (being the at least one actual output of the ANN). The at least one artificial neuron may be present in a single hidden layer of the ANN. In other embodiments of the invention where the ANN has a plurality of artificial neurons, the plurality of artificial neurons may be distributed across one or more hidden layers. Where there is more than one layer, each layer may be interconnected with a previous and a subsequent layer.

The artificial neurons may processes information using a connectionist approach to computation. The ANN may be an adaptive system, where it changes based on external or internal information that flows through the ANN during the training or learning phase. Specifically, the weight (or strength) of the connections (such as between adjacent artificial neurons, or between an input and an artificial neuron) within the ANN is adapted to change.

In embodiments of the invention, the first parameter (heart rate variability data), the second parameter (vital sign data) or a combination of the first parameter and the second parameter may be classified as feature vectors of the patient health data. The artificial neural network may be trained with the feature vectors.

The artificial neural network may be implemented as instructions stored in a memory that when executed by a processor cause the processor to perform the functions of the artificial neural network.

In embodiments of the invention, the artificial neural network may be based on support vector machine architecture, wherein the associated weight of the at least one input of each artificial neuron of the plurality of artificial neurons is initialized from a library used by the support vector machine. The support vector machine may have an aggregated output comprising a decision function, the decision function given by $$f(x) = \text{sgn}\left(\sum_{i=1}^{N} \alpha_i y_i k(x, x_i) + b\right)$$

wherein sgn( ) is a sign function, $(x,x_i)$ is set of feature vector, $k(x,x_i)$ is a kernel matrix constructed by x and $x_i$, $y_i$ is 1 or −1, which is the label of feature vector $x_i$, $\alpha_i$ and b are parameters used to define an optimal decision hyperplane so that the margin between two classes of patterns can be maximized in the feature space.

In embodiments of the invention, the artificial neural network may be based on an extreme learning machine architecture, wherein the associated weight of the at least one input of each artificial neuron of the plurality of artificial neurons is initialized through random selection by the extreme learning machine. The artificial neural network may be realized as a single-layer feed-forward network, whereby the prediction on the survivability of the patient is derived from the function, $$f_{\tilde{N}}(x_j) = \sum_{i=1}^{\tilde{N}} \beta_i g(w_i \cdot x_j + b_i) = t_j \quad j = 1, \ldots, N$$

wherein $x_j$ is an input vector to an input of one of the plurality of artificial neurons for j=1, 2, . . . , N input vectors; $w_i$ is the associated weight of the input of the artificial neuron receiving the $x_j$ input vector; $g(w_i \cdot x_j + b_i)$ is an output of the artificial neuron receiving the $x_j$ input vector . . . for i=1, 2, . . . , $\underline{N}$ artificial neurons; $\beta_i$ is the output weight vector that associates an $i^{th}$ hidden neuron with a respective output neuron; and $b_i$ is the bias for the $i^{th}$ hidden neuron.

In embodiments of the invention, training of the artificial neural network may be based on back-propagation learning.

In embodiments of the invention, the back-propagation learning may use the Levenberg-Marquardt algorithm.

In embodiments of the invention, each of the plurality of artificial neurons of the artificial neural network may have an activation function, the activation function being selected from a group of functions comprising hardlim, sigmoid, sine, radial basis and linear.

In embodiments of the invention, the sequence of information within the RR interval may be partitioned into non-overlapping segments; and the non-overlapping segments may be used to train the artificial neural network. A length of signal within the RR interval of each of the filtered ECG signal may be extracted. The length of signal may be partitioned into non-overlapping segments; and at least one of the non-overlapping segments may be selected to train the artificial neural network.

In embodiments of the invention, each of the non-overlapping segments may be of substantially equal length. In embodiments of the invention, the non-overlapping segments may have a fixed length.

According to embodiments of the present invention, a method of predicting the survivability of a patient is provided. The method includes measuring a first set of parameters relating to heart rate variability data of a patient. A second set of parameters relating to vital sign data of the patient is also measured. An artificial neural network including a network of interconnected nodes is provided, the nodes including a plurality of artificial neurons. Each artificial neuron has at least one input with an associated weight adjusted by training the artificial neural network using an electronic database having a plurality of sets of data. Each set of data has at least a parameter relating to heart rate variability data and a parameter relating to vital sign data, each set of data further having a parameter relating to patient survivability. The method includes processing the first set of parameters and the second set of parameters to produce processed data suitable for input into the artificial neural network. The processed data is provided as input into the artificial neural network. An output is then obtained from the artificial neural network, the output providing a prediction on the survivability of the patient.

In embodiments of the invention, the processed data of the first set of parameters and the processed data of the second set of parameters may be represented as a feature vector.

In embodiments of the invention, the processed data may be the first set of parameters and the second set of parameters being represented as normalized data.

In embodiments of the invention, the processed data may be partitioned into non-overlapping segments, so that the input into the artificial neural network may include sets of one or more of the non-overlapping segments of processed data. A result may be obtained for each of the sets of one or more of the non-overlapping segments of processed data, so that each of the results may be considered to predict the survivability of the patient.

In embodiments of the invention, majority voting may be used to determine the prediction on the survivability of the patient, the majority voting represented by the function $$\hat{y} = \max_{j=1}^{2} \sum_{m=1}^{M} D_{m,j}$$

wherein $D_{m,j}$ is an intermediate variable for final decision making, $D_{m,j}$ assigned a value of 1 if a $m^{th}$ classifier chooses class j in the decision ensemble, and 0 otherwise.

In embodiments of the invention, the result of the artificial neural network may be coded as a two class label. The method of predicting the survivability of a patient may then further include applying a label-based algorithm to each of the two class label results to decide the output from the artificial neural network, thereby providing a prediction on the survivability of the patient.

In embodiments of the invention, the prediction on the survivability of the patient is either death or survival of the patient.

In embodiments of the invention, a patient survivability prediction system includes: a first input to receive a first set of parameters relating to heart rate variability data of a patient; a second input to receive a second set of parameters relating to vital sign data of the patient; and a memory module storing instructions to implement an artificial neural network. The artificial neural network includes a network of interconnected nodes, the nodes including a plurality of artificial neurons. Each artificial neuron has at least one input with an associated weight adjusted by training the artificial neural network using an electronic database having a plurality of sets of data. Each set of data has at least one a parameter relating to heart rate variability data and a parameter relating to vital sign data. Each set of data further has a parameter relating to patient survivability. The patient survivability prediction system further includes a processor to execute the instructions stored in the memory module to perform the functions of the artificial neural network and output a prediction on the survivability of the patient based on the first set of parameters and the second set of parameters; and a display for displaying the prediction on the survivability of the patient.

In embodiments of the invention, the patient survivability prediction system may further include a port to receive the first set of parameters from the first input and the second set of parameters from the second input.

In embodiments of the invention, the patient survivability prediction system may further include a first port to receive the first set of parameters from the first input; and a second port to receive the second set of parameters from the second input.

According to embodiments of the invention, a method of predicting the survivability of a patient is provided. The method includes: measuring a first set of parameters relating to heart rate variability data of a patient; measuring a second set of parameters relating to vital sign data of the patient and obtaining a third set of parameters relating to patient characteristics. The first set of parameters, the second set of parameters and the third set of parameters are provided as sets of normalized data values, where required, to a scoring model implemented in an electronic database. The scoring model has a respective category associated to each parameter of the first set of parameters, the second set of parameters and the third set of parameters. Each category has a plurality of pre-defined value ranges, each of the plurality of value ranges having a pre-defined score. A score for each parameter of the first set of parameters, the second set of parameters and the third set of parameters is determined by assigning the sets of normalized data to respective pre-defined value ranges, encompassing the sets of normalized data values, of the plurality of value ranges of the category associated to the respective parameter of the first set of parameters, the second set of parameters and the third set of parameters. A total score, being a summation of the score for each parameter of the first set of parameters, the second set of parameters and the third set of parameters is obtained. The total score provides an indication on the survivability of the patient.

It will be appreciated that in embodiments of the invention, only selected parameters of the first set of parameters, the second set of parameters and the third set of parameters may be provided to the scoring model implemented in the electronic database. For instance, the third set of parameters may entirely not be obtained from the patient or provided to the scoring model. In embodiments of the invention, further parameters of patient health data may be measured and provided to the scoring model.

The scoring model may be any suitable process or algorithm, implementable in an electronic database, which can assign a score to each range of values within each category associated to each parameter of the first set of parameters, the second set of parameters and the third set of parameters. For instance, the scoring model may be based on a mathematical model using logistic regression, such as univariate analysis.

In embodiments of the invention, the score may be a numerical value, which may be determined according to statistical information or standard medical information. The numerical value of the pre-defined score may also depend on the pre-defined value range, which the pre-defined score is assigned to, in the respective category. In embodiments of the invention, adjacent pre-defined value ranges within the same category may each have an assigned pre-defined score of the same numerical value. It will also be appreciated that pre-defined value ranges within different categories may each have an assigned pre-defined score of the same numerical value.

The scope of the pre-defined value ranges may depend on the category to which they belong to and may be determined according to statistical information or standard medical information. The scope of a pre-defined value range for a category associated to a parameter of the first set of parameters may be different to the scope of a pre-defined value range for a category associated to a parameter of the second set of parameters. In embodiments of the invention, there may be no overlap between pre-defined value ranges of the same category.

In embodiments of the invention, assigning sets of normalized data to respective pre-defined value ranges may involve first determining which category of the scoring model the normalized data belongs to. Subsequently, it may be determined which one of the pre-defined value ranges the normalized data value belongs to, by ascertaining that the numerical value of the normalized data value falls within or is encompassed by the scope of the respective pre-defined value range.

In embodiments of the invention, the scoring model may further include a plurality of risk categories, each category having a pre-defined range of values. The method of predicting the survivability of a patient may further include assigning the total score to the category having the pre-defined range of values encompassing the total score, to determine which of the plurality of risk categories the total score belongs to.

While embodiments of the invention will be shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

It will be appreciated that common numerals, used in the relevant drawings, refer to components that serve a similar or the same purpose.

FIG. 1 is a flow chart 100 illustrating a method, according to one embodiment of the present invention, used to produce an artificial neural network capable of predicting the survivability of a patient.

The method includes three steps 102, 104 and 106.

In step 102, patient health data is stored in an electronic database. The patient health data includes a plurality of sets of data, each set having at least one of a first parameter relating to heart rate variability data and a second parameter relating to vital sign data. Each of the plurality of sets of data further has a third parameter relating to patient survivability.

In step 104, a network of nodes interconnected to form an artificial neural network (ANN) is provided. The nodes include a plurality of artificial neurons, each artificial neuron having at least one input with an associated weight. The artificial neural network (ANN) provided in step 104 may be a mathematical model or computational model simulating the structure and/or functional aspects of a biological neural network.

In step 106, the artificial neural network is trained using the patient health data such that the associated weight of the at least one input of each artificial neuron of the plurality of artificial neurons is adjusted in response to respective first, second and third parameters of different sets of data from the patient health data. This results in the artificial neural network being trained to produce a prediction on the survivability of a patient.

As mentioned above, artificial neural networks (such as the ANN provided in step 104) are based on the way the human brain approaches pattern recognition tasks, providing an artificial intelligence based approach to solve classification problems. A model is 'learned' during a training process using previously known input-output pairs. The trained model is then tested with new data.

Various artificial neural network topologies are available, including single-layer and multi-layer feedforward networks. Such ANNs are typically BP (backpropagation) based, whereby weights of hidden layers are adjusted during training to minimize an error function.

In embodiments of the invention, the nodes of the ANN include at least one input (being the at least one actual input of the ANN), at least one artificial neuron and at least one output (being the at least one actual output of the ANN).

Figure 2:
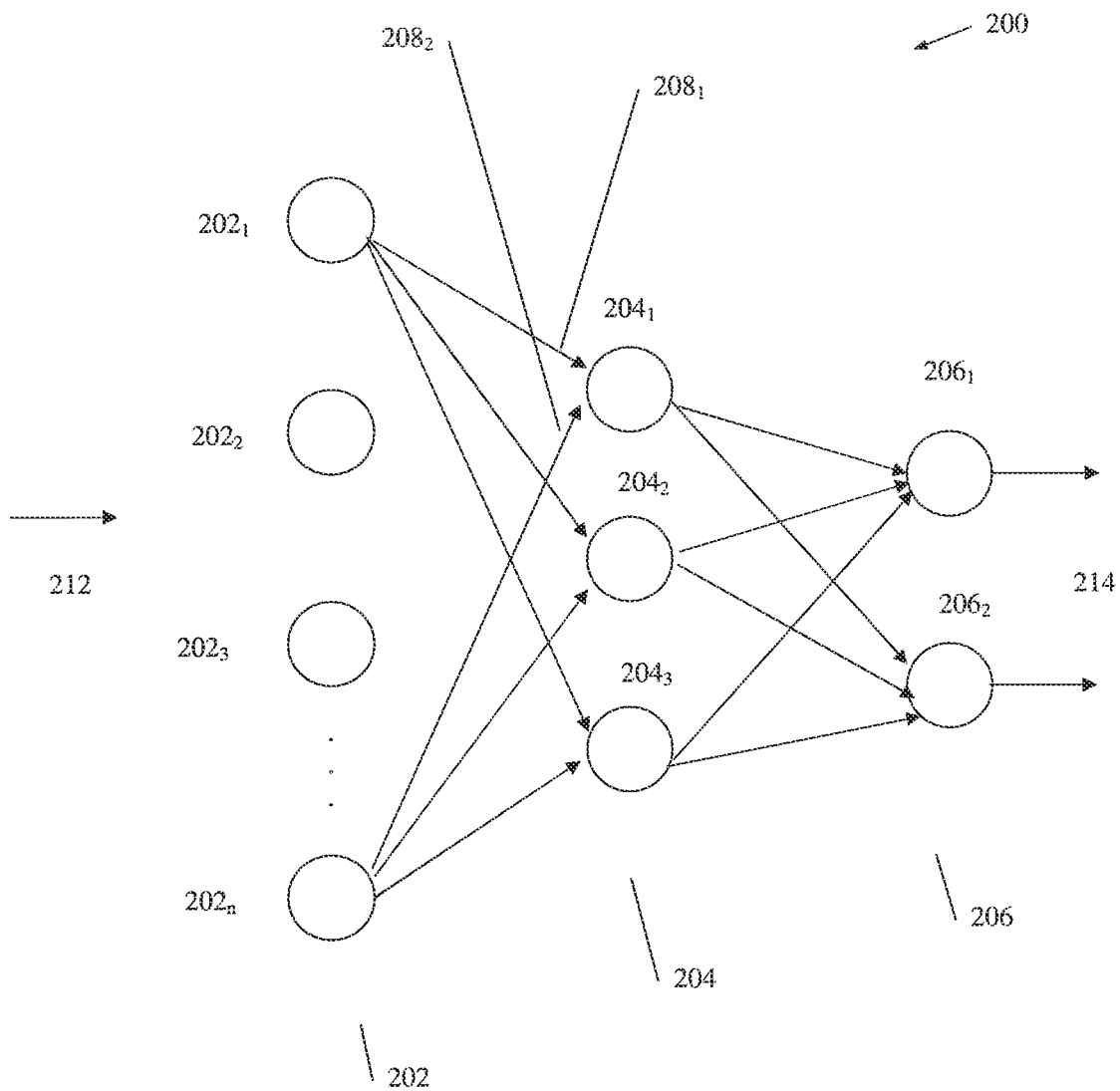
FIG. 2 is a schematic representation of an artificial neural network according to one embodiment of the present invention.

FIG. 2 is a schematic representation of an artificial neural network 200 according to one embodiment of the present invention. With reference to the flow chart 100 shown in FIG. 1, the artificial neural network 200 may be provided in the step 104.

In the embodiment shown in FIG. 2, the ANN 200 is a single hidden-layer feedforward network (SLFN). The ANN 200 has an input layer 202, a hidden layer 204 and an output layer 206.

The input layer 202 includes one or more input nodes $202_1, 202_2, 202_3, \ldots$ and $202_n$. While FIG. 2 shows that the hidden layer 204 has only three artificial neurons $204_1, 204_2$ and $204_3$, it will be appreciated that any number of artificial neurons may be used. The output layer has two output nodes $206_1$ and $206_2$.

The output of each of the input nodes $202_1, 202_2, 202_3, \ldots$ and $202_n$ may be connected to an input of every one of the artificial neurons $204_1, 204_2$ and $204_3$ in the hidden layer 204. However, for the sake of simplicity, only a few such connections between the input layer 202 and the hidden layer 204 is illustrated in FIG. 2. Similarly, the output of each of the artificial neurons $204_1, 204_2$ and $204_3$ may be connected to an input of every one of the output nodes $206_1$ and $206_2$ in the output layer 206. In this manner, a network of interconnected nodes is formed.

Each of the artificial neurons $204_1, 204_2$ and $204_3$ has at least one input. For simplicity, only inputs for one of the artificial neurons are labeled in FIG. 2, being inputs $208_1$ and $208_2$ for the artificial neuron $204_1$. Each input of the respective artificial neurons ($204_1, 204_2$ and $204_3$) has an associated weight.

In training the ANN 200 to predict the survivability of a patient, the associated weight of the at least one input of each artificial neuron (for example inputs $208_1$ and $208_2$ of the artificial neuron $204_1$) is adjusted in response to respective first, second and third parameters of different sets of data from the patient health data. With reference to step 102 of flow chart 100 of FIG. 1, the first parameter relates to heart rate variability data, the second parameter relates to vital sign data and the third parameter relates to patient survivability.

The trained ANN 200 can then be used to assist clinical decisions on whether a patient exhibiting certain symptoms will survive or will die, i.e. the trained ANN 200 can assist in the prediction on the survivability of the patient.

The trained ANN 200 may be used to predict the survivability of the patient as follows. A first set of parameters relating to heart rate variability data of the patient is measured. A second set of parameters relating to vital sign data of the patient is also measured. The first set of parameters and the second set of parameters are processed to produce processed data suitable for input into the trained artificial neural network 200. The processed data is provided as input 212 into the artificial neural network 200, for example at the input layer 202. An output 214 is then obtained from the artificial neural network 202, the output 214 providing a prediction on the survivability of the patient.

Figure 3:
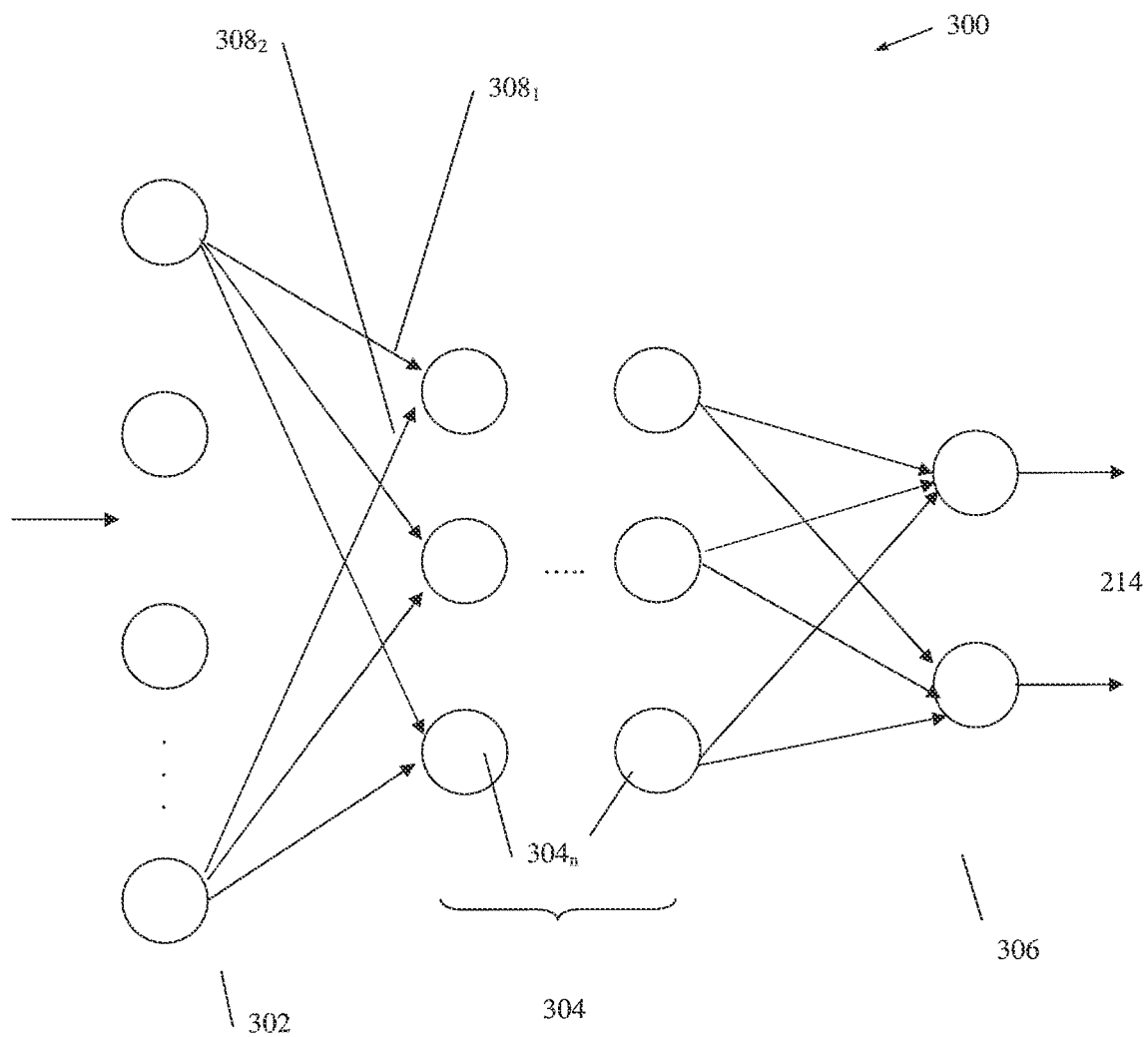
FIG. 3 is a schematic representation of an artificial neural network according to one embodiment of the present invention.

FIG. 3 is a schematic representation of an artificial neural network 300 according to one embodiment of the present invention. With reference to the flow chart 100 shown in FIG. 1, the artificial neural network 300 may be provided in the step 104.

In the embodiment shown in FIG. 3, the ANN 300 is a multi-layer feedforward network. The ANN 300 has an input layer 302, a hidden layer 304 and an output layer 306.

The main difference between the ANN 300 of FIG. 3 and the ANN 200 of FIG. 2 is that the ANN 300 of FIG. 3 has several layers of interconnected artificial neurons $304_n$ instead of having a single layer of artificial neurons. Each layer of artificial neurons $304_n$ may be interconnected with a previous and a subsequent layer of artificial neurons $304_n$.

Another difference is that it takes a longer time to train the ANN 300 (compared to training the ANN 200 of FIG. 2) to predict the survivability of a patient, as there are more artificial neurons $304_n$ having inputs (for instance $308_1$ and $308_2$) where their associated weights have to be adjusted in response to patient health data.

Functionally, the hidden layer 304 still works in the same manner as the hidden layer 204 of the ANN 200. Similarly, the input layer 302 and the output layer 306 function in the same manner as the input layer 202 and the output layer 206 respectively of the ANN 200. Thus, the functions of the input layer 302, the hidden layer 304 and the output layer 306 are not further elaborated.

In a further embodiment of the invention, the system may be used as a means of triaging patients such as in combat situations, other mass trauma situations such as multi-vehicular automobile accidents or terrorist incidents. The trained ANN 300 can be used to assist clinical decisions on whether a patient exhibiting certain symptoms will survive or will die, i.e. the trained ANN 300 can assist in the prediction on the survivability of the patient.

FIG. 4 shows a block diagram of a system 400 used to predict the survivability of a patient, the system 400 built in accordance to an embodiment of the invention.

The system 400 acquires ECG signals real-time, filter noise and ectopic beats, generate HRV parameters and combine these with other vital parameters such as blood pressure, oxygen saturation, respiratory rate, pulse rate and age into a composite triage score. The aim of the system 400 is to have a portable, field usable, integrated device that will assist medical staff in rapid, real-time triage of patients based on risk prediction. Such a system 400 would be particularly applicable in mass disaster scenarios as well as high volume patient load situations like the Emergency Department.

There are known systems that use HRV as a predictor, but such systems focused mainly on specific patient conditions such as sepsis and head trauma. Further, available HRV analysis software packages either require the RR interval (ECG beat-to-beat intervals) to be generated externally or have limited functionality in terms of the available features. These packages work 'off-line' using the entire recording or on a selected segment and do not have automatic methods to identify and isolate non-sinus beats before computing HRV parameters.

The system 400 has the following advantages over known existing systems:
1. Dynamically acquire and process raw ECG signals from a patient to reduce the effects of noise and other artifacts such as movement and interference.
2 Generate the RR interval sequence after automatically isolating non-sinus beats and artifacts.
3. Compute and display time and frequency domain HRV parameters.
4. Acquire and display real time vital signs including blood pressure, respiration rate and SpO2 (Saturation of peripheral oxygen) using appropriate sensors and signal conditioning circuits.
5. Compute and display a risk score(s) related to the various possible patient outcomes.
The system 400 is able to perform the above functions in "real-time".

The system 400 has three main functional blocks: a signal acquisition block 402, a signal processing block 404 and an analysis block 406.

The signal acquisition block 402 has sensor and signal conditioning hardware 408 for acquiring an ECG signal and other vital signs from a patient 401. The sensor and signal conditioning hardware 408 may include sensors that detect ECG signals, blood pressure, SpO2 and respiration rate.

The signal acquisition block 402 has a data acquisition (DAQ) card 410, which in one embodiment contains the signal conditioning circuits used for processing output from the sensor and signal conditioning hardware 408. The signal conditioning circuits are designed to process signals from these sensors. The signal conditioning circuits comprise electronic components that perform functions such as isolation and amplification of the various signals measured by the sensors. The output of each signal conditioning circuit is a signal with a peak amplitude of about 1V.

The DAQ card 410 may also act as an interface to a computer. An input panel also accepts additional information such as age and gender of the patient 401. The DAQ card is used to perform analog-to-digital conversion of the acquired signals from the sensor and signal conditioning hardware 408 for interfacing with a computer for further processing. A National Instruments PCMCIA or USB card may be used for this purpose. The DAQ card should preferably have a sampling rate of around 10 kHz and use 16-bit quantization.

The signal processing block 404 includes a signal processing module 426, a vital sign module 420 and a patient information module 418.

The signal processing module 426 includes an ECG pre-processing module 412, a beat detection and post processing module 414, and a HRV parameter calculation module 416.

The ECG pre-processing module 412 processes raw ECG data from the signal acquisition block 402 to suppress unwanted signals such as noise, motion artifacts and power line interference which may affect the accuracy of HRV parameters eventually extracted from the ECG data. The beat detection and post processing module 414 acts on denoised signal from the ECG pre-processing module 412 to detect a heartbeat and to exclude non-sinus beats during postprocessing. The duration between consecutive sinus beats are compiled into an RRI (beat to beat interval) sequence from which HRV parameters are computed.

The HRV parameter calculation module 416 is used to extract HRV parameters from the output of the beat detection and post processing module 414.

The patient information module 418 receives input regarding additional information about the patient 401, such as age, gender, Glasgow Coma Score (GCS) and medical history. The normalization is carried out with analysis block 406.

Vital sign data such as blood pressure, SpO2 and respiration rate is processed by the vital sign module 420. The normalization is carried out with analysis block 406.

The analysis block 406 includes a HRV parameter and patient information analysis module 422 and a risk score module 424. It will be appreciated that the ANN in accordance with embodiments of the invention (see for instance FIGS. 1 to 3) is implemented in the analysis block 406.

The analysis block 406 computes HRV parameters obtained from the signal processing block 404 and compiles them into feature sets using results obtained from patient health data obtained from hospital records or from conducting field studies. Patient 401 demographics such as age, gender, Glasgow Coma Score, etc, which can be keyed into the system, are also used in the analysis along with the vital signs of the patient 401. A risk score providing a prediction on different outcomes such as death, ward admission and intensive care unit (ICU) admission of the patient 401 is computed and may be displayed on a computer screen.

The signal processing block 404 and the analysis block 406 may be implemented using software, such as "LabView" deployed on a hand held electronic device 430 (illustrated in FIG. 4 as a dotted block). The "LabView" program performs signal acquisition, noise removal, beat detection, post-processing, computation of HRV parameters and display of the risk scores as described above. In this manner, the hand held electronic device 430 acts as a standalone device, where a suitable deployment platform for the hand held electronic device 430 would be "CompactRIO" by "National Instruments".

In further detail, for an ECG signal from the signal acquisition block 402, noise removal is performed within the "LabView" program using a 1-50 Hz band-pass filter which suppresses high frequency interference as well as low frequency variations due to baseline wander and shift, and motion artifacts. The denoised signal is displayed on a screen 432.

In another embodiment (not shown), the signal acquisition block 402, the signal processing block 404 and the analysis module 406 are integrated into a single hand held electronic device.

Beat detection is performed from a 1D array of ECG sample points x(n), as follows. In one embodiment of the present invention, where a 1D array of ECG sample points x(n) are provided, the upper and lower amplitude thresholds ($T_{upper}$ and $T_{lower}$) are set after finding the maximum value (ref_peak) within the first few seconds of data. The thresholds are defined as:

$$T_{upper} = \text{ref\_peak} + 0.4 * \text{ref\_peak}$$

$$T_{lower} = \text{ref\_peak} - 0.35 * \text{ref\_peak}$$

Then a QRS peak is said to occur at the point i if the following conditions are met, $x(i)$ lies between $T_{upper}$ and $T_{lower}$;

$x(i+1) - x(i) < 0$; and $x(i) - x(i-1) > 0$;

where the R-peak is the point with maximum value.

The positions of other QRS peaks within the filtered ECG signal may be located by iterating the process of: locating another peak value and locating other minimum values on either side of the another peak value. When the another peak value is above the upper amplitude threshold while the other minimum values are both below the lower threshold, the location of the peak value is denoted as an R position. The location of the minimum value occurring closest on the left side of the R position is denoted as a Q position and the location of the minimum value occurring closest on the right side of the R position is denoted as an S position. In this manner, the location of another QRS peak is determined.

The above technique of beat detection automatically generates RR interval sequences from given ECG data, after correcting for ectopic beats and noise, with minimal user input. The beat detection technique was tested using data from known databases (for example the MIT-BIH arrhythmia database, website: http://www.physionet.org/physiobank/database/mitdb/) and results were found to match closely to manually annotated values. The technique was also tested on ambulance ECG data, which is subject to higher levels of noise and motion artifacts, with good results.

From detected QRS complexes, the processed RR interval (RRI) sequence can be obtained. The processed RRI is used to calculate the following HRV parameters, from which time domain and frequency domain measures may be measured: Examples of time domain measures are:
Time Domain Measures
1. Average length of the RR interval (aRR): Mean of all sinus RR intervals (N-N) in the sequence
2. Standard deviation of all N-N interval (SDNN)
3. Mean heart rate (mean HR)
4. Standard deviation of all instantaneous heart rate values (SDHR)
5. Square root of the mean squared differences of successive N-N intervals (RMSSD): The square root of the mean of the sum of the squares of differences between adjacent N-N intervals
6. HRV triangular index: Total number of all N-N intervals divided by the height of the histogram of all NN intervals.
7. Baseline width of a triangle fit into the N-N interval histogram using a least squares technique (TINN)
Examples of frequency domain measures are:
Frequency Domain Measures
Frequency domain measures are calculated based on the power spectrum of the RRI sequence which is generated using a Lomb-Scargle periodogram. The following parameters are then calculated:
1. Total power (TP): Variance of N-N intervals over the segment till 0.4 Hz
2. VLF: Power in very low frequency range <0.04 Hz
3. LF: Power in low frequency range. 0.04-0.15 Hz
4. HF: Power in high frequency range. 0.15-0.4 Hz
5. LF norm: LF power in normalized units: LF norm=LF/(TP−VLF)×100%
6. HF norm: HF power in normalized units: HF norm=HF/(TP−VLF)×100%
7. LF/HF: Ratio of LF/HF In addition to the above HRV parameters, a user can also input other patient 401 parameters such as age, gender, Glasgow Coma Score, respiration rate, blood pressure, SpO2 and heart rate. These parameters for the patient 401 are used to calculate a risk score to predict the survivability of the patient 401. In calculating the risk score, it will be appreciated that the artificial neural network within the analysis block 406 has been trained as outlined in FIGS. 1 to 3 above. The output of the analysis block 406 will be a risk score which will classify the patient as being 'high', 'medium' or 'low' risk for each of the hospital outcomes including death, hospital admission and ICU admission.

Each of the FIGS. 5 to 9 show a flow chart, in accordance with embodiments of the invention, implemented by a respective functional block of the system 400 of FIG. 4.

Figure 5:
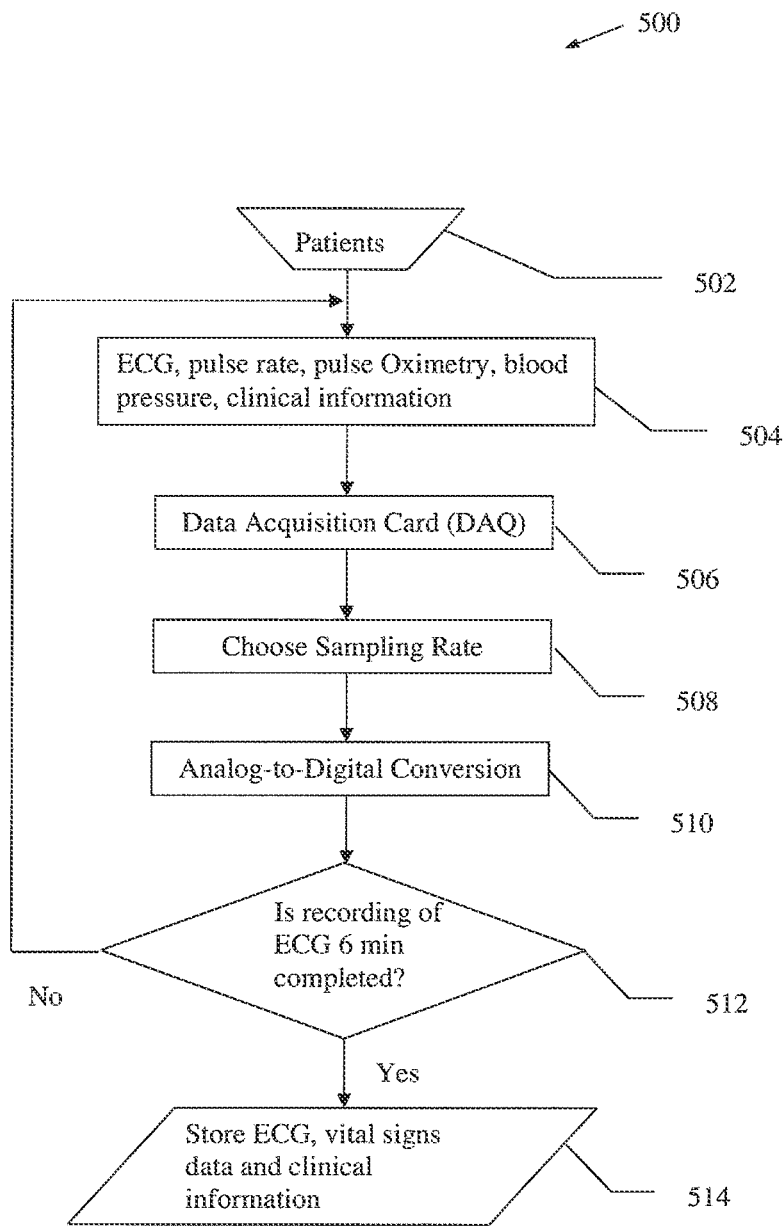
FIG. 5 shows a flow chart, in accordance with embodiments of the invention, implemented by a signal acquisition block.

FIG. 5 shows a flow chart 500, in accordance with embodiments of the invention, implemented by the signal acquisition block 402 of FIG. 4.

In step 502 a patient is chosen to perform prediction on survivability.

In step 504, the patient's ECG signal, pulse rate, pulse oximetry, blood pressure and clinical information are obtained. Examples of clinical information include age, gender and medical history (eg. cancer, diabetes, heart disease).

In step 506, the patient's ECG signal, pulse rate, pulse oximetry, blood pressure and clinical information is sent to a data acquisition (DAQ) card. All the information from step 506 will be acquired by the DAQ card sent as data to a computer or stand-alone device in real-time.

In step 508, the information from step 506 is sampled and converted from an analog signal into digital data in step 510.

In step 512, the signal acquisition block 402 (see FIG. 4) checks the recording length of digital ECG data that has been collected. For reliable calculation of HRV parameters from the digital data obtained in step 510, it has been noticed that a recording length of at least six minutes is required. If six minutes worth of digital ECG data has yet to be collected, the flow chart 500 returns to step 504. On the other hand, if six minutes of digital ECG data has been recorded, the flow chart stops at step 514. In step 514, the digital ECG data is stored, along with vital signs and clinical information of the patient, into the computer or stand-alone device.

Figure 6:
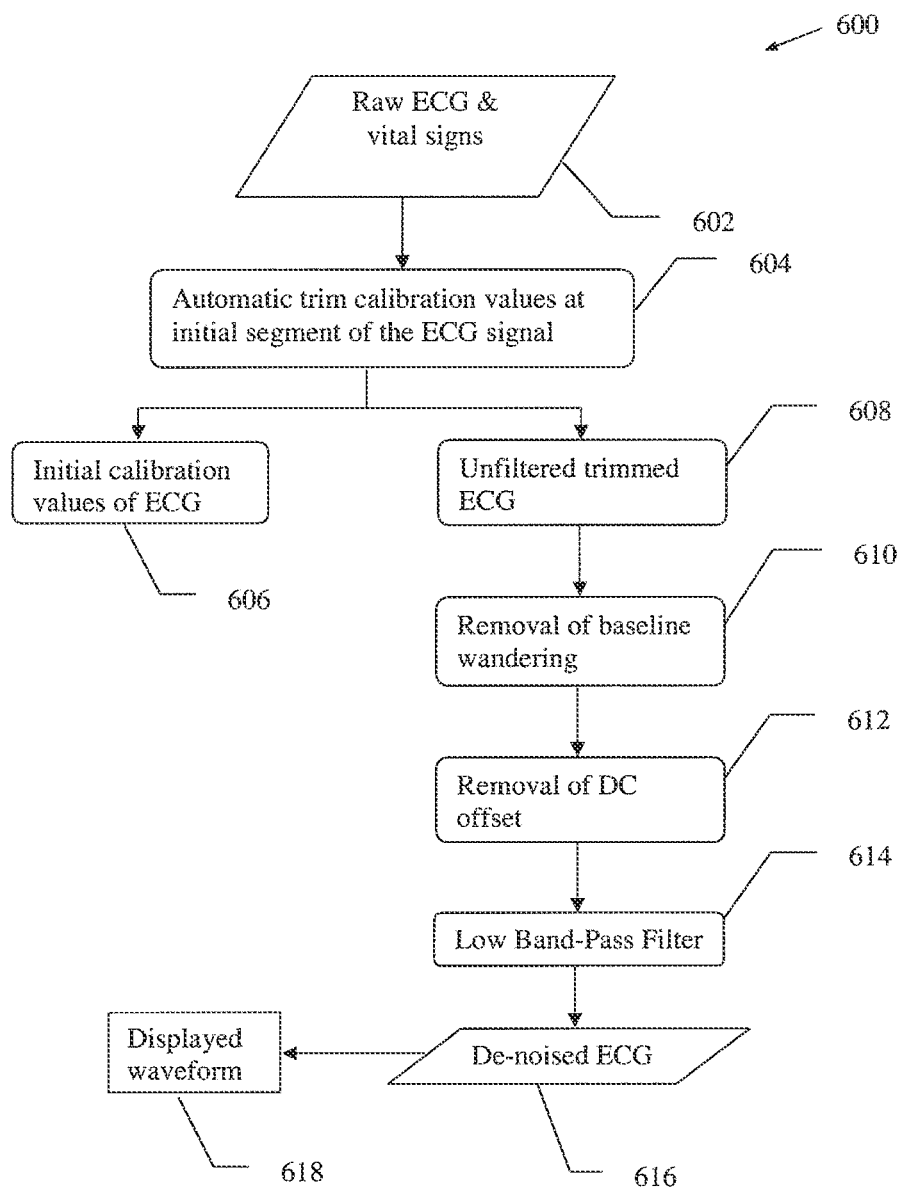
FIG. 6 shows a flow chart, in accordance with embodiments of the invention, implemented by a signal processing module.

FIG. 6 shows a flow chart 600, in accordance with embodiments of the invention, implemented by the signal processing module 426 of FIG. 4.

The flow chart 600 begins with step 602 with the ECG pre-processing module 412 having a raw ECG data and vital sign data as input.

Raw ECG data may not always contain a single continuous length of data points. Often, leads may be removed or settings may have been changed, resulting in gaps in the data. Hence in step 604, the calibration values are removed or trimmed, the data segments separated and concatenated to get one continuous stream of data.

In step 606, the signal processing module 426 has unfiltered ECG data with calibration values trimmed. The effects of noise and artifacts in unfiltered ECG data are well known. The low amplitude of the ECG signal makes it highly susceptible to noise and interference from a variety of sources. These include high-frequency noise, power line interference, baseline wander, motion artifact, and other low frequency distortions. The presence of noise can result in false positives at the QRS detection stage and thus injects errors into the generation of the HRV sequence and in the subsequent HRV analysis.

Noise removal techniques exist (such as using band pass filters) to remove low frequency noise such as baseline drift and also attenuate high frequency variations without significant distortion of the QRS complex. The presence of abrupt baseline shift and other artifacts can result in peaks being wrongly detected as QRS complexes. Since these artifacts may lie within the same frequency range as the QRS complex, they may be difficult to eliminate. Thus, in step

610 baseline wandering is removed from the unfiltered trimmed ECG data and in step 612, the DC offset is removed.

Frequency components of the QRS complex typically lie between a range of 10 and 25 Hz. In step 614, the data from step 612 is processed using a band pass filter with an operating frequency range of 5 to about 28 Hz. It will thus be appreciated that the band pass filter facilitates location of QRS complex by enhancing the QRS complex inside the unfiltered trimmed ECG data from step 612 and to suppress high frequency variations. A bandpass frequency range, that is successful in eliminating baseline drift and magnifying the QRS complex without significantly distorting the signal and increasing the chance of false detections, is applied.

In step 616, a de-noised ECG signal is obtained which is used for further processing to detect QRS and calculate HRV measures. In step 618, the de-noised ECG signal waveform is displayed for instance in the screen 432 (see FIG. 4).

Figure 7:
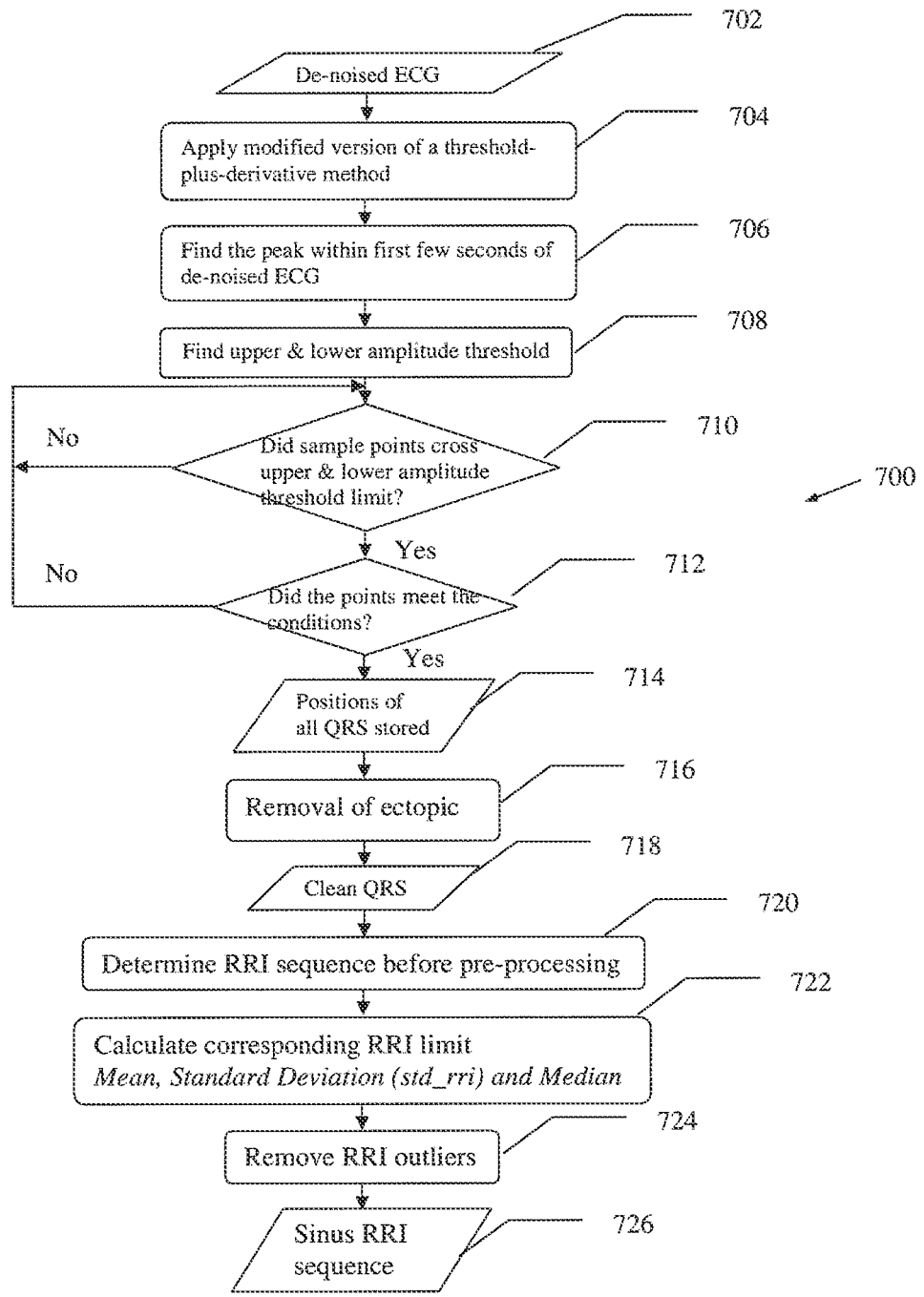
FIG. 7 shows a flow chart, in accordance with embodiments of the invention, implemented by a beat detection and post processing module.

FIG. 7 shows a flow chart 700, in accordance with embodiments of the invention, implemented by the beat detection and post processing module 414 of FIG. 4.

The flow chart 700 begins with step 702 with the beat detection and post processing module 414 having a de-noised ECG signal.

In summary, the objective of steps 704 to 726 is to detect the location of the QRS complexes, which allows us the calculation of RR intervals. The location, magnitude and shape of the QRS complex as well as the duration between adjacent complexes allows sifting out ectopic beats and other non-sinus rhythm which is to be excluded from the HRV analysis. In this manner, reliable heart rate variability data can be extracted from an ECG signal from a patient.

In steps 706 to 714, a maximum peak data value first occurring in the filtered ECG signal is located. An upper amplitude threshold and a lower amplitude threshold from the located maximum peak value are determined. A peak value and minimum values on either side of the peak value are located. In embodiments of the invention, either side refers to the left and right sides of the peak value. The conditions of whether the peak value is above the upper amplitude threshold, while the minimum values are below the lower amplitude threshold are met is checked. If the conditions are met, the location of the peak value is denoted as an R position. The location of the minimum value occurring closest on the left side of the R position is denoted as a Q position, and the location of the minimum value occurring closest on the right hand side of the R position is denoted as an S position. The location of a QRS peak within the filtered ECG signal is thus determined.

Further detail on steps 704 to 726 is provided as follows.

In step 704, a modified threshold-plus-derivative method is used as it has found to be effective and robust in the presence of noise. The modified algorithm works as follows.

In step 706, a maximum peak data (ref_peak) value is found, given a 1D array of ECG sample points x(n), within the first few seconds of de-noised ECG data. In step 708, upper and lower amplitude thresholds are found.

In embodiments of the invention, the upper and lower amplitude thresholds ($T_{upper}$ and $T_{lower}$) are set after finding the maximum value (ref_peak) within the first few seconds of data. The thresholds are defined as:

$$T_{upper} = \text{ref\_peak} + 0.4 * \text{ref\_peak}$$

$$T_{lower} = \text{ref\_peak} - 0.35 * \text{ref\_peak}$$

In step 710, it is determined whether the ECG sample points cross the upper and lower amplitude thresholds ($T_{upper}$ and $T_{lower}$). The flow chart 700 does not proceed to step 712 if the ECG sample points do not pass this criteria. The use of the upper and lower amplitude thresholds ($T_{upper}$ and $T_{lower}$) for QRS complex detection ensures that large peaks due to noise (e.g. as a result of electrode placement or motion artifacts) are not detected as QRS complexes.

Step 712 occurs if the ECG sample points cross the upper and lower amplitude thresholds ($T_{upper}$ and $T_{lower}$). In step 712, it is determined whether the sample points that pass the criteria check at step 710 can be considered as a QRS peak. A QRS peak is said to occur at the point i if the following further conditions are met, $x(i)$ lies between $T_{upper}$ and $T_{lower}$;

$x(i+1) - x(i) < 0$;

$x(i) - x(i-1) > 0$;

where the R-peak is the point with maximum value.

If the further conditions above are met, the points corresponding to the Q and S waves are then determined by locating the nearest local minimum within a window on either side of the R-peak. The exact locations of the Q, R and S positions are then saved in step 714. Otherwise (i.e. if the further conditions above are not met), the flow chart 700 returns to step 710. The positions of other QRS peaks within the filtered ECG signal may be located by iterating the process of steps 710 and 712, i.e. locating another peak value and locating other minimum values on either side of the another peak value. When another peak value is above the upper amplitude threshold while the other minimum values are both below the lower threshold, the location of the peak value is denoted as an R position. The location of the minimum value occurring closest on the left side of the R position is denoted as a Q position and the location of the minimum value occurring closest on the right side of the R position is denoted as an S position. In this manner, the location of another QRS peak is determined. All positions of QRS peaks are then stored in step 714.

Besides noise, ectopic beats and other outliers (due to exercise, muscle or other artifacts) have to be identified because they can perturb the RR interval sequence.

Ectopic beats are generated when autonomic modulation of the sinoatrial node is temporarily lost, initiating a premature contraction of the atria or ventricles, occurring both in normal subjects as well as patients with heart disease. Generally, most such ectopics are manifested with a wide QRS complex.

Steps 716 to 726 are used to removing outliers from the sequence of information within the RR interval. The process involves finding a median value and a standard deviation value for the RR interval. A tolerance factor based on the standard deviation value is calculated. A portion of information that lies within the RR interval spanning either side of the median value by the tolerance factor is retained. Heart rate variability data may be obtained from the retained portion of information and the remaining portion of the information from the sequence of information is discarded.

Further detail on steps 716 to 726 is provided as follows.

In step 716, non-sinus beats are isolated. Beats adjacent to the non-sinus beats are removed to produce a clean QRS peak in step 718.

The RR interval sequence is then generated in step 720 based on normal beats. Once this is done, the locations of beats corresponding to sinus rhythm are stored in an array for the next stage of processing. Using the detected peaks, the RR intervals correspond to the distance between successive QRS peaks. The calculated intervals are stored in an array for post-processing. Although noise, artifacts and isolated abnormal beats are already been filtered, the beats can result in very short or very long RR intervals either due to compensatory pauses or by virtue of removal of some beats. Hence, the sequence may contain outliers.

To automatically identify these outliers, the statistical properties of the sequence are applied onto the RR interval sequence in step 720.

In step 722, a RRI limit is calculated as follows.
1. Find the median and standard deviation for the RR interval sequence
2. Calculate a tolerance factor based on the standard deviation(s)
3. Search for any intervals lying more than Ms away from the median interval, where M is the tolerance factor. Outliers exist within the intervals lying more than Ms away from the median interval.
4. Separate these outliers, which occurs in step 724

In step 724, a tolerance factor is calculated based on the spread of the values. The tolerance factor this is used to separate the outliers, thus tackling both noisy as well as normal data. Therefore, sinus RRI sequences which are noise-free and ectopic-free are generated in step 726 before computing HRV parameters.

To summarize FIGS. 6 and 7, extracting the heart rate variability data, in embodiments of the invention, comprises filtering the ECG signal to remove noise and artifacts, locating a QRS complex within the filtered ECG signal; finding a RR interval between successive QRS peaks of the QRS complex; and processing the sequence of information within the RR interval to obtain the heart rate variability data.

Figure 8:
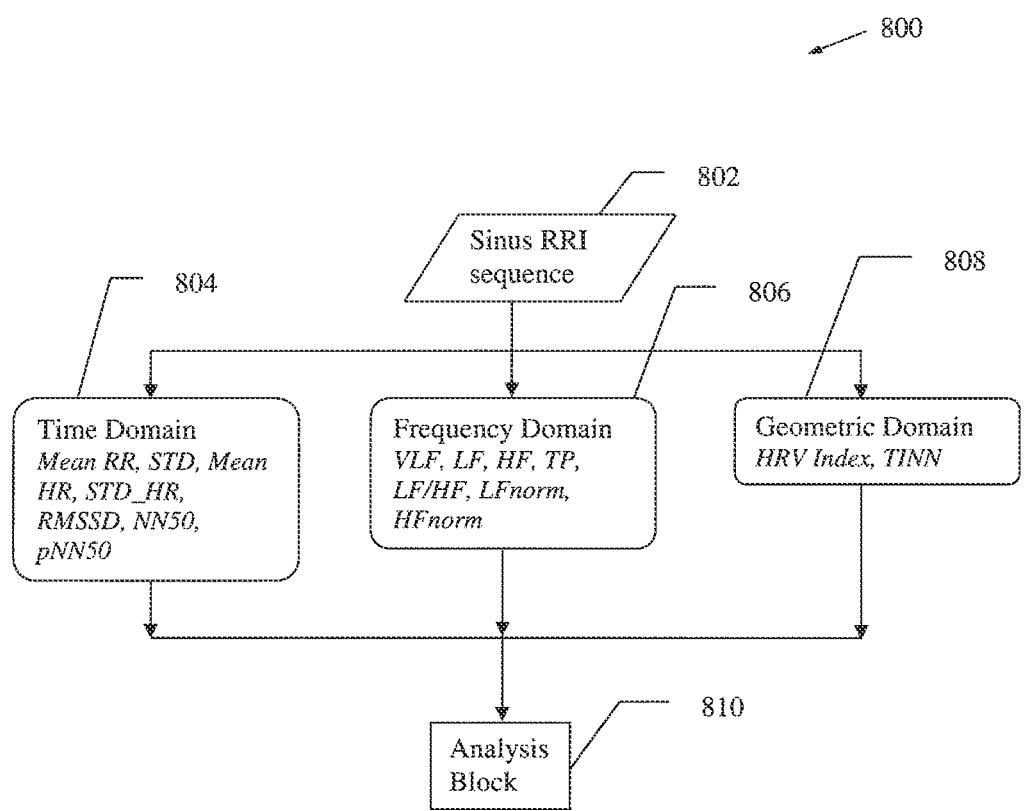
FIG. 8 shows a flow chart, in accordance with embodiments of the invention, implemented by a HRV parameter calculation module.

FIG. 8 shows a flow chart 800, in accordance with embodiments of the invention, implemented by the HRV parameter calculation module 416 of FIG. 4.

The flow chart 800 begins with step 802 with the HRV parameter calculation module 416 having sinus RR interval (sinus RRI) sequences.

Three categories of HRV measures, time domain data, frequency domain data and geometric domain data are calculated from the sinus RRI sequences.

In step 804, time domain data such as mean of RR intervals (mean RR), standard deviation of RR intervals (STD), mean of the instantaneous heart rate (mean HR), standard deviation of the instantaneous heart rate (STD_HR), root mean square of differences between adjacent RR intervals (RMSSD), number of consecutive RR intervals differing by more than 50 ms (NN50), and percentage of consecutive RR intervals differing by more than 50 ms (pNN50) is calculated. Time domain analysis is based on statistical parameters (primarily based on standard deviation) calculated from the RR intervals over time for both short-term (less than 5 mins) as well as long-term recordings (more than 24 h).

The meaning of each of the terms: mean RR, STD, mean HR, STD_HR, RMSSD, NN50 and pNN50 is provided below.

Mean RR (or aRR) is the average width of the RR interval measured in milliseconds or seconds. This gives a general idea of the heart rate and can be calculated for both long-term as well as short-term recordings.

STD (or SDNN) is the standard deviation of all RR intervals in the data set [21], giving a general idea of the spread of the values. STD is suitable for both short-term as well as long-term recordings.

Mean HR is the mean of the instantaneous heart rate.
STD_HR is the standard deviation of the instantaneous heart rate.

RMSSD (or r-MSSD or SDSD) is found by taking the square root of the mean of the sum of the squares of differences between successive heart periods in a 24-hour interval. It is an index of the variation in RR interval length. RMSSD is not a sensitive measure of variation over long periods of time but it is particularly sensitive to misclassified or beat-labeling errors like retaining premature ventricular contractions. Among the time domain variables, this is the most sensitive to vagal influences, although it is unable to determine the sympathetic and parasympathetic contributions.

NN50 (or RR-50) is the total number of times in 24 hours that the difference between 2 successive RR intervals exceeds 50 ms. It is the most sensitive of all measures to mislabeled beats and occurrences of premature ventricular or atrial contractions will rapidly increase the RR50 count. It is also highly sensitive to longer variations of the heart periods of normal sinus rhythm.

pNN50 (or % RR50) is the percentage of absolute differences between normal RR intervals that exceed 50 ms, normalized by the average heart rate.

In step 806, frequency domain data such as: power in very low frequency range ($<=0.04$ Hz) (VLF), power in low frequency range (0.04 to 0.15 Hz) (LF), power in high frequency range (0.15 to 0.4 Hz) (HF) being an index of vagal activity, total power which is estimated from the variance of NN intervals in the segment and is measured in $ms^2$ (TP), ratio of LF power to HF power (LF/HF), LF power in normalized units: LF/(TP−VLF)×100 (LFnorm), and HF power in normalized units: HF/(TP−VLF)×100 (HFnorm) is calculated. Spectral analysis is a sensitive, quantitative method for evaluating HRV in the frequency domain. The analysis is done by transforming the time series to the frequency domain and finding the power spectrum. The distribution of spectral energy in various bands is quantified and used as an index of variability. This distribution of energy reflects the contribution of the sympathetic and parasympathetic arms of the autonomic nervous system.

In step 808, geometric domain data such as: total number of all RR intervals divided by height of histogram of intervals (HRV Index) and base width of triangle fit into RR histogram using least squares method (TINN) is obtained.

The meaning of the terms: HRV Index and TINN is provided below.

HRV index (or HRV triangular index or RR triangular index) is obtained after the RR interval sequence is converted to a sample density distribution. The triangular index is the integral of the density distribution, i.e., the number of all RR intervals divided by the maximum of the density distribution.

TINN, the triangular interpolation of RR interval histogram, is the baseline width of the sample density distribution measured as a base of a triangle approximating the RR interval distribution.

In step 810, the above 16 HRV parameters (Mean RR, STD, Mean HR, STD_HR, RMSSD, NN50, pNN50, VLF, LF, HF, TP, LF/HF, LFnorm, HFnorm, HRV Index and TINN) are combined and sent to the analysis block 406 (see FIG. 4) for classifier training (i.e. training of the artificial neural network within the analysis block 406) and patient outcome prediction.

Figure 9:
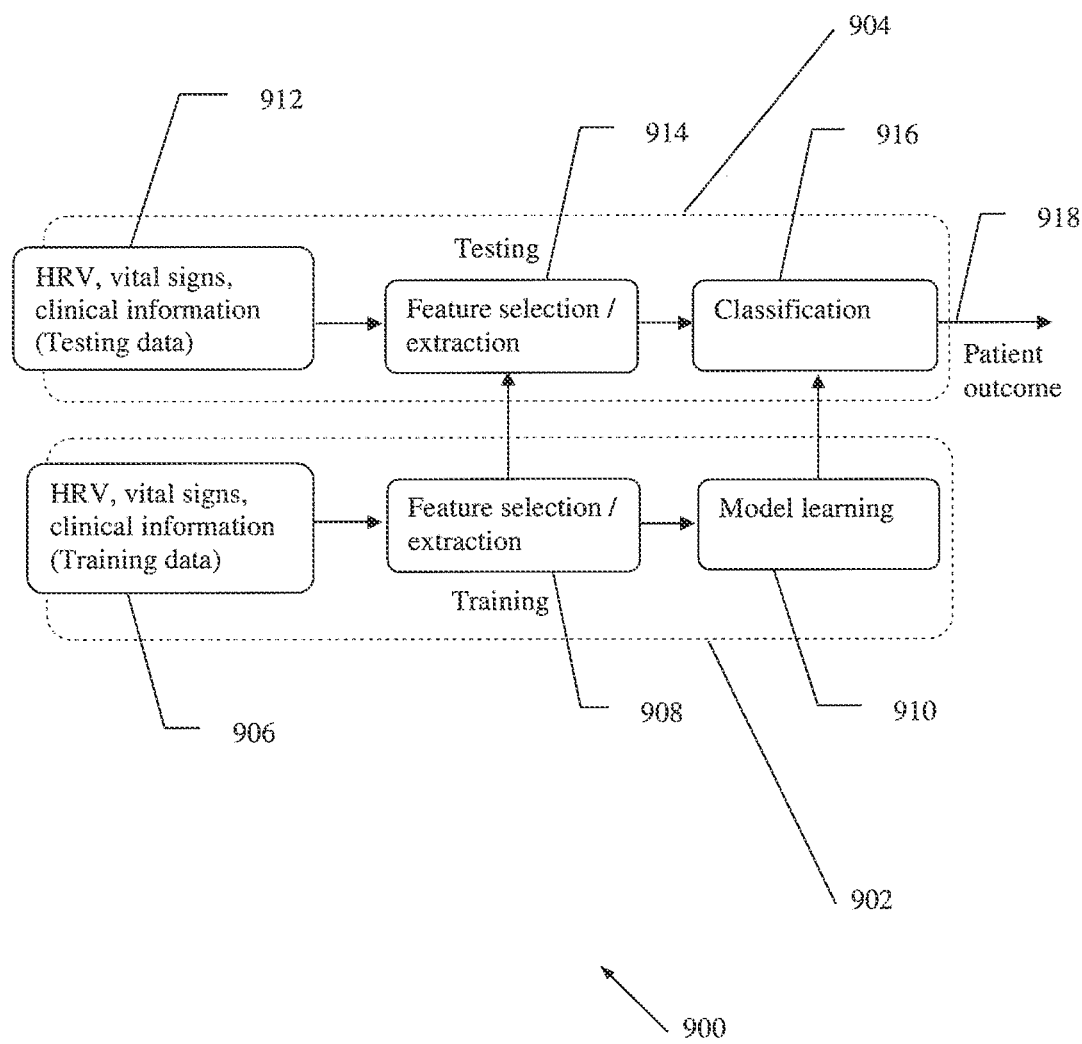
FIG. 9 shows a block diagram representation of how data flows in an analysis block.

FIG. 9 shows a block diagram representation of how data flows in the analysis block 406 of FIG. 4.

The analysis block 406 is first configured to be trained (represented by reference numeral 902) using training data and subsequently the trained analysis block 406 is tested using testing data (represented by reference numeral 904).

In step 906, a training data set is constructed in which each patient is represented as a feature vector of HRV parameters, clinical information (like age, gender, ethnicity) and vital signs.

In step 908, the training data set represented as feature vectors is further processed with feature selection and/or extraction algorithms for reducing feature dimensionality so as to remove redundant information.

Besides discriminatory features, the selection of a classifier plays a key role in building an efficient prediction system. Judging a classifier usually depends on evaluating its generalization ability that refers to the classifier's performance in categorizing unseen patterns. Since the same classifier may have various performances on different applications, the needs of the application should be analyzed before choosing a proper classifier. In order to predict the outcomes for unseen patients, the classifier should be trained with training samples prior to doing categorization on testing samples. Therefore, in step 910 a classification model, suitable for the application at hand, is learnt after choosing proper pattern representations in step 908.

In step 912, testing data from a patient is represented as a combined feature vector of HRV measures, clinical information and vital signs.

In step 914, feature selection and/or extraction algorithms are applied to the testing data from a patient represented as the combined feature vector for extracting discriminatory information.

In step 916, the extracted discriminatory information is processed using the classification model selected in step 910. The output 918 from step 916 is a label of the testing data, giving a prediction on the patient outcome.

Figure 10:
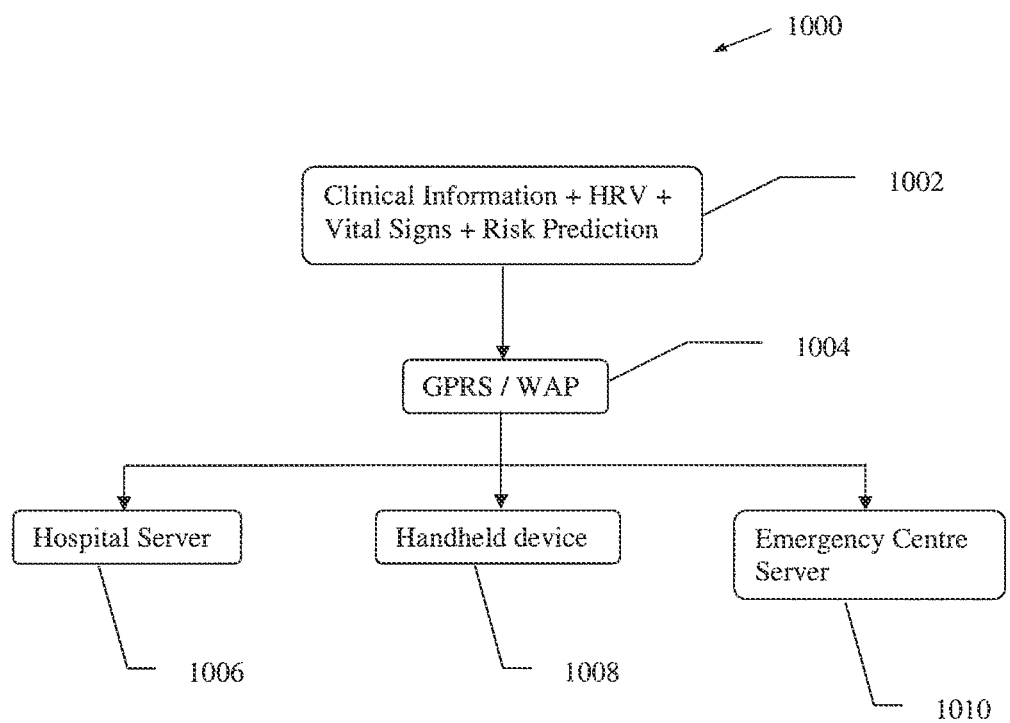
FIG. 10 shows a flow chart illustrating use of a system, in accordance with embodiments of the invention, utilizing wireless technology.

FIG. 10 shows a flow chart 1000 illustrating a system, in accordance with embodiments of the invention, utilizing wireless technology.

The flow chart 1000 begins with step 1002, where a patient survivability prediction system, has data on clinical information, HRV parameters, vital signs and a patient survivability risk prediction.

In step 1004, wireless technologies such as GPRS or WAP are used to establish a network infrastructure between the patient survivability prediction system described in step 1002 and peripheral systems such as a hospital server, other handheld devices or a emergency centre server. In steps 1006, 1008 and 1010, the data of the patient survivability prediction system is transmitted to the hospital server, the handheld device and the emergency centre server. The steps 1006, 1008 and 1010 allows clinicians to receive and analyze patients' condition in real-time and remotely.

FIG. 11 summarizes raw ECG data characteristics of 100 patients chosen for analysis, including 40 cases of death and 60 cases of survival. The data set comprised 63 male and 37 female patients between the ages of 25 and 92 years. Vital signs and patient outcomes were obtained from hospital records, including information such as patient demographics (age, race, gender) and priority code.

These 100 patients were acquired from critically ill patients attended at the Department of Emergency Medicine (DEM), Singapore General Hospital (SGH). "Critically ill" refers to patients triaged in the most severe categories P1 or P2 at the DEM. These include trauma and non-trauma patients who underwent ECG monitoring. ECG signals were acquired using LIFEPAK 12 defibrillator/monitor, downloaded using the CODE-STAT Suite and matched with the patients' hospital records. Cases were included for review if they contained more than 70% sinus rhythm and excluded if there were large segments of non-sinus rhythm (atrial and ventricular arrhythmias).

Figure 12:
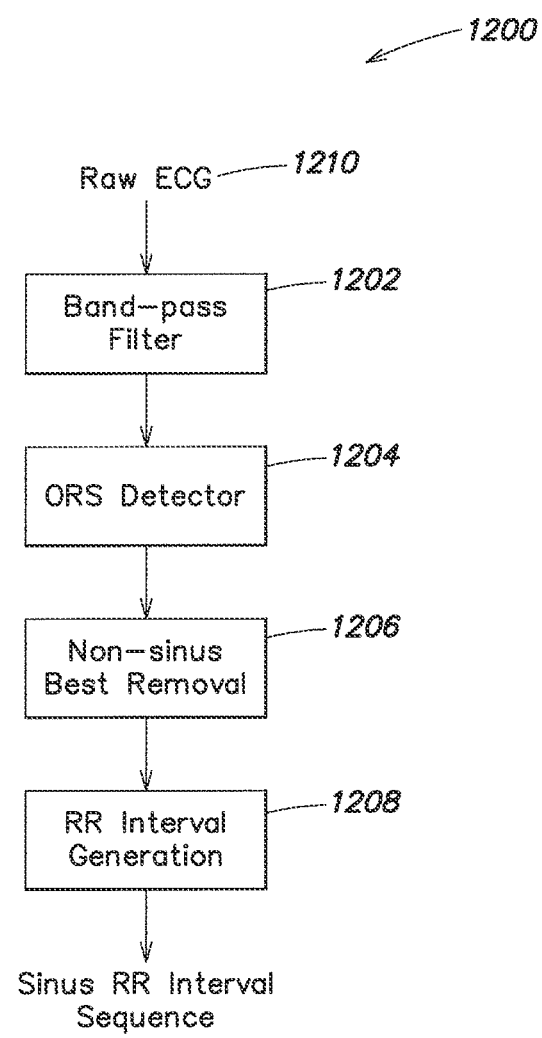
FIG. 12 shows a flow chart, in accordance with embodiments of the invention, illustrating how an ECG signal is pre-processed to calculate HRV parameters.

The raw ECG data shown in FIG. 11 has to be pre-processed to obtain reliable HRV measures. FIG. 12 shows a flow chart 1200, in accordance with embodiments of the invention, illustrating how an ECG signal is pre-processed to calculate HRV parameters.

In step 1202, raw ECG data 1210 is processed to reduce the effects of noise and artifacts using a 5-28 Hz band-pass filter. This frequency range is found to enhance the QRS complex against the background noise for easy peak detection.

In step 1204, a modified threshold-plus-derivative method is implemented to detect the QRS complexes.

In step 1206, all ectopics and other non-sinus beats are excluded.

In step 1208, the RR intervals are calculated based on the sinus rhythm. Cases are included for review if they contain more than 70% sinus rhythm (measured as number of sinus beats detected/total number of detected beats) and excluded if they contain sustained arrhythmias or large segments of noise/artifact. The resulting beat-to-beat (RR) interval sequences 1210 are used for calculating various HRV measures.

In embodiments of the invention, steps 1202 to 1208 can use the methodology as described with reference to FIGS. 6 and 7. Thus, no further elaboration is provided on steps 1202 to 1208.

Classification of the Artificial Neural Network

In training the artificial neural network used in embodiments of the invention, the first parameter, the second parameter or a combination of the first parameter and the second parameter may be classified as feature vectors of the patient health data. The artificial neural network is then trained with the feature vectors. As one objective of the artificial neural network is to predict mortality, the artificial neural network will be implemented to solve a two-class classification problem (the patient outcome is either death or survival).

In embodiments of the invention, various training algorithms may be used to train the artificial neural network (200, 300) and determine the optimal hidden layer weights (see description in respect of FIGS. 2 and 3).

Levenberg-Marquardt Algorithm

For instance, training of the artificial neural network (200, 300) may be based on back-propagation learning. The Levenberg-Marquardt algorithm may be used to perform the back-propagation learning.

Extreme Learning Machine (ELM)

An extreme learning machine architecture may be used to train embodiments of the invention where a SLFN is used (such as the one shown in FIG. 2). Compared with conventional gradient-based learning approaches, ELM has a fast learning process and meanwhile retains good generalization ability. The extreme learning machine has the advantage of improving training speed by eliminating the need to tune all the parameters of the artificial neural network. The extreme learning machine may be implemented for SLFN with either additive neurons or radial basis function (RBF) kernels.

In an extreme learning machine architecture, the associated weight and biases of the at least one input of each artificial neuron of the artificial neural network is initialized through random selection. The output weights of each artificial neuron may be determined by finding the least square solution.

Given a training set consisting of N samples $$L=\{(x_j,t_j)|x_j\in R^n, t_j\in R^m, j=1,2,\ldots,N\} \quad (1)$$

where $x_j$ is a p×1 input vector and $t_j$ is an q×1 target vector, an SLFN with $\underline{N}$ hidden nodes is formulated as $$f_{\tilde{N}}(x_j) = \sum_{i=1}^{\tilde{N}} \beta_i g(w_i \cdot x_j + b_i) = t_j \quad j=1,\ldots,N \quad (2)$$

wherein $x_j$ is an input vector to an input of one of the plurality of artificial neurons for j=1, 2, . . . , N input vectors; $w_i$ is the associated weight of the input of the artificial neuron receiving the $x_j$ input vector; $g(w_i \cdot x_j + b_i)$ is an output of the artificial neuron receiving the $x_j$ input vector . . . for i=1, 2, . . . , $\underline{N}$ artificial neurons; $\beta_i$ is the output weight vector that associates an $i^{th}$ hidden neuron with a respective output neuron; and $b_i$ is the bias for the $i^{th}$ hidden neuron. The prediction on the survivability of the patient is derived from the equation (2) above.

A compact format of equation (2) can be written as $$H\hat{\beta}=T \quad (3)$$

where $H(w_1, \ldots, w_{\tilde{N}}, b_1, \ldots, b_{\tilde{N}}, x_1, \ldots, x_N)$ is hidden layer output matrix of the network, $h_{ji}=g(w_i \cdot x_j+b_i)$ is the output of ith hidden neuron with respect to $x_{j,i}=1, 2, \ldots, \tilde{N}$ and j=1, 2, . . . , N; $\hat{\beta}=[\beta_1, \ldots, \beta_{\tilde{N}}]^T$ and $T=[t_1, \ldots, t_N]^T$ are output weight matrix and target matrix, respectively. To obtain small non-zero training error, random values can be assigned for parameters $w_i$ and $b_i$, and thus the system becomes linear so that the output weights can be estimated as $\beta=H^\dagger T$, where $H^\dagger$ is the Moore-Penrose generalized inverse of the hidden layer output matrix H.

$$H(w_1, \ldots, w_{\tilde{N}}, b_1, \ldots, b_{\tilde{N}}, x_1, \ldots, x_N) = \begin{bmatrix} g(w_1 \cdot x_1 + b_1) & \ldots & g(w_{\tilde{N}} \cdot x_1 + b_{\tilde{N}}) \\ \vdots & \ldots & \vdots \\ g(w_1 \cdot x_N + b_1) & \ldots & g(w_{\tilde{N}} \cdot x_N + b_{\tilde{N}}) \end{bmatrix}_{N \times \tilde{N}} \quad (4)$$

In general, the ELM algorithm can be summarized as follows:
1) Generate parameters $w_i$ and $b_i$ for i=1, . . . , $\tilde{N}$,
2) Calculate the hidden layer output matrix H,
3) Calculate the output weight using $\beta=H^\dagger T$.

Support Vector Machine (SVM)

Another training algorithm is basing the artificial neural network on support vector machine architecture. A support vector machine is a learning machine designed for binary classification. In the support vector machine, input vectors are non-linearly mapped to a very high-dimensional feature space in which a linear decision surface (hyperplane) is constructed. The surface is chosen such that it separates input vectors with maximum margin.

The associated weight of the at least one input of each artificial neuron is initialized from a library used by the support vector machine. An example of a suitable library would be the LIBSVM software package by Chang et al.

Consider a set of linearly separable features $(x_1, y_1), \ldots (x_N, y_N)$ are given as training data, where $x_i \in X, y_i \in \{\pm 1\}$ with a hyperplane $<w, x>+b=0$. The set of vectors is said to be optimally separated by the hyperplane if it is separated without errors and the margin is maximal. A canonical hyperplane has the constraint for parameters w and b: $\min_{x_i} y_i((w, x_i)+b)=1$. A separating hyperplane in canonical form must satisfy the constraints:

$$y_i(<w, x_i>+b)\geq 1, i=1, \ldots, N \quad (5)$$

Quadratic programming is used for solving the constraint optimization problem in order to find the optimal hyperplane. The optimization criterion is the width of the margin between the class. Then for a new pattern x, the hyperplane decision function can be written as $$f(x) = \text{sgn}\left(\sum_{i=1}^{N} \alpha_i y_i \langle x, x_i \rangle + b\right) \quad (6)$$

Since most real-world data is nonlinearly distributed, a kernel trick has been used to extend the classifier to be nonlinear, in which kernel functions are used to replace the simple dot product. The weight vector then becomes an expansion in the feature space, and we obtain the decision function of the support vector machine may be given by $$f(x) = \text{sgn}\left(\sum_{i=1}^{N} \alpha_i y_i k(x, x_i) + b\right) \quad (7)$$

wherein sgn( ) is a sign function; $(x;x_i)$ is set of feature vector; $k(x;x_i)$ is a kernel matrix constructed by x and $x_i$; $y_i$ is 1 or −1; which is the label of feature vector $x_i$; $\alpha_i$ and b are parameters used to define an optimal decision hyperplane so that the margin between two classes of patterns can be maximized in the feature space.

Three kernels may be used to provide diversified solutions, they are linear kernel $k(x_i, x_j)=x_i \cdot x_j$, sigmoid kernel $k(x_i, x_j)=\tanh(\alpha x_i \cdot x_j + \gamma)$, and radial basis function (RBF) kernel $k(x_i, x_j)=\exp(-\|x_1-x_j\|^2/2\sigma^2)$ where $\sigma$ is the width of RBF function.

Segment Based Method

When measuring ECG signals from patients, the length of ECG signal varies from one patient to another, which will affect the calculation of HRV measures.

Figure 13:
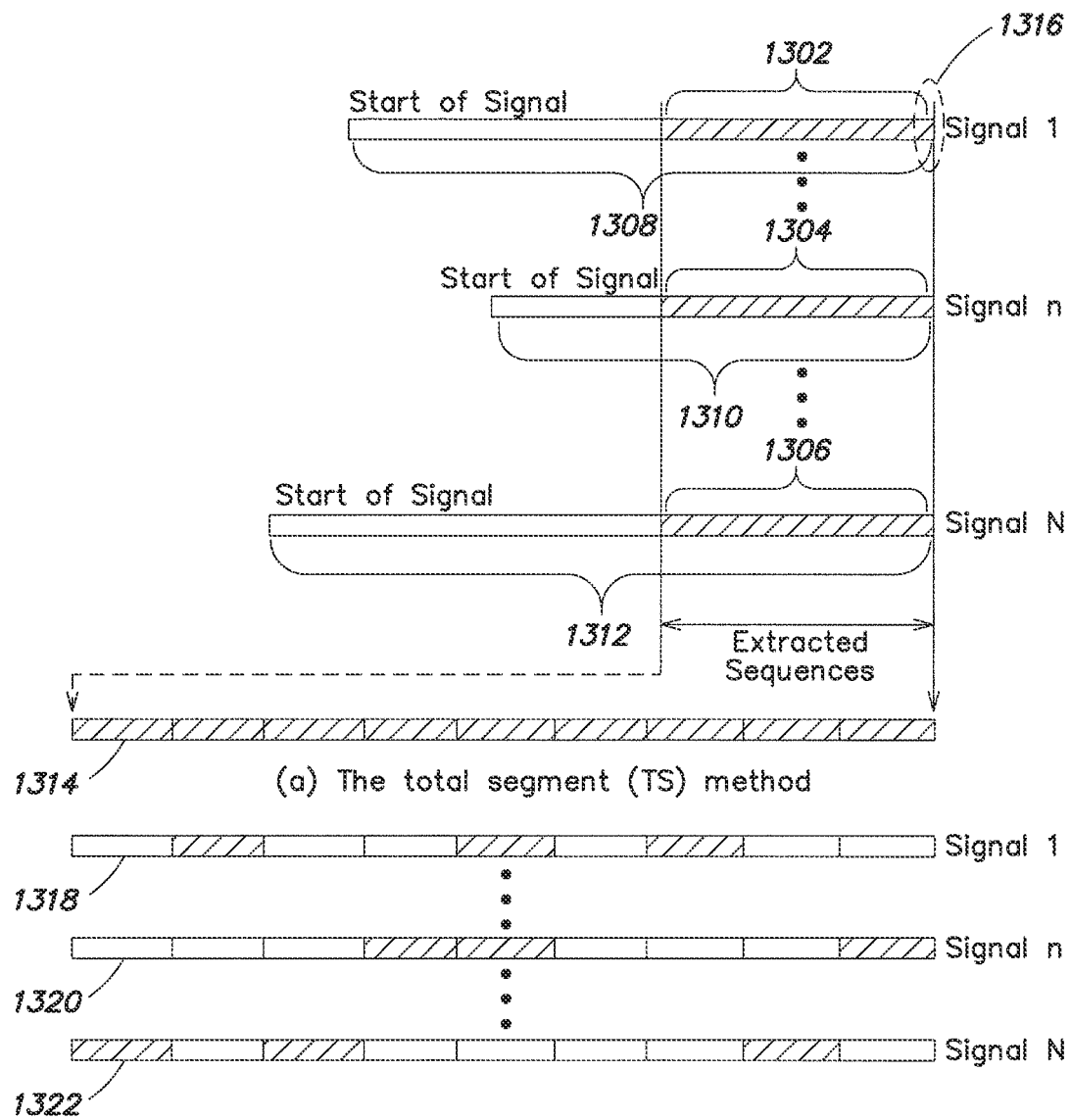
FIG. 13 shows how data extraction is performed.

To avoid possible effects of length variation, segments of identical length of ECG signals are extracted for all patients. Since raw ECG data contains non-sinus beats and noise, extraction is done on the RR interval sequences. FIG. 13 shows how the extraction is performed. In FIG. 13, a sequence of information (1302, 1304 and 1306) within an RR interval (1308, 1310 and 1312) is partitioned into segments 1314, in accordance with embodiments of the invention.

In embodiments of the invention, the sequence of information (1302, 1304 and 1306) within the RR interval (1308, 1310 and 1312) may be partitioned into non-overlapping segments 1314. The non-overlapping segments 1314 may be used to train an artificial neural network.

In other embodiments of the invention, a length of signal within the RR interval (1308, 1310 and 1312) of each of the filtered ECG signal may be extracted. The length of signal may be partitioned into non-overlapping segments 1314; and at least one of the non-overlapping segments 1314 may be selected to train the artificial neural network.

In embodiments of the invention, each of the non-overlapping segments 1314 may be of substantially equal length. In embodiments of the invention, the non-overlapping segments 1314 may have a fixed length. In embodiments of the invention, each of the non-overlapping segments 1314 may be of unequal length. In embodiments of the invention, the non-overlapping segments 1314 may be of an adjustable length.

Extraction starts from the signal end 1306 as this portion of recording correlates better with the patient outcome than any other segments in the original sequence. The entire sequence (1308, 1310 and 1312) and the extracted portion (1302, 1304 and 1306) as "global" signal and "local" signal, respectively.

High prediction accuracy may not be achieved with only N (number of patients) feature vectors. The local sequence (1302, 1304 and 1306) may be further partitioned into several non-overlapped segments 1318, 1320 and 1322 of fixed length and the prediction of the patient outcome is given by majority voting using the patient's corresponding segments.

Firstly, an ensemble of classifiers with M segments of the same patient are combined to improve the overall predictive performance. Since the outputs of a predictor can be either class labels or class-specific continuous values (the degrees of support given to those classes), there are two types of combination rules. The patient outcome is coded as either 0 or 1, thus the label-based strategy such as majority voting can be used as the combining method. This rule seeks the class that receives the highest number of votes and assigns it to the predicted label for the testing pattern. The details of the segment based prediction method is elaborated as follows, noting that while ECG data is shown in FIG. 13, the segment based prediction method is applicable to other 1-D biomedical signals such as electroencephalography (EEG).

Suppose a data set L, $\{(x_m, y_n), n=1, \ldots, N, m=1, \ldots, M\}$, consists of N patients and each local sequence is divided into M segments. Assume that if $\hat{x}$ is the test data, $\hat{y}$ is predicted by $\varphi(\hat{x}, L)$. Because M segments are used, we have a set of M predictive labels for $\hat{x}$. The objective is to better predict $\hat{y}$ using M predictors instead of a single one. As a two-class problem is being considered, $\varphi(\hat{x}, L)$ predicts a series of class labels $\omega_j \in \{0, 1\}$ where j=1, 2, and the prediction of the $m^{th}$ classifier (constructed on $m^{th}$ segment) is $D_{m,j}$ whose value is assigned to 1 if the $m^{th}$ classifier chooses class $\omega_j$, and 0 otherwise. Then the decision on $\hat{x}$ is defined as $$\hat{y} = \max_{j=1}^{2} \sum_{m=1}^{M} D_{m,j} \quad (8)$$

where the output $\hat{y}$ is the value with highest number of votes. In applications where there are J classes, i.e., j=1, . . . , J, the predictive label is given by $$\max_{j=1}^{J} \sum_{m=1}^{M} D_{m,j}$$

Thus far, a total segment (TS) method approach is discussed as all M segments are used for decision making. The complete TS algorithm is provided below.

TS Algorithm
Inputs
   ECG signals of N patients, $S_1, \ldots, S_N$.
   Hospital records including vital signs and patient outcomes $y_1, \ldots, y_N$.
   Number of iterations K and number of total segments M.

Calculation of HRV Measures
1. Do pre-processing on the original ECG signals such as filtering, QRS detection, non-sinus beat removal, etc.
2. Extract "local" RR interval signals to obtain sequences $S'_1, \ldots, S'_N$.
3. Partition $S'_N$ into M non-overlapped segments and calculate HRV measures $z_n^m$ where n=1, . . . , N and m=1, . . . , M.
4. Construct feature vectors $x_n^m$ with $z_n^m$ and vital signs, where m=1, . . . , M.

Prediction of ACP Event or Mortality
For k=1, . . . , K
a) Partition the data set by randomly selecting $N_{trn}$ patients into training set and the rest of $N_{tst}$ patients into testing set. Since each patient is represented by M feature vectors, there are $N_{trn}M$ samples in the training set and $N_{tst}M$ samples in the testing set.
b) Train classifier with $N_{trn}M$ feature vectors and predict labels for $N_{tst}M$ samples in the testing set. Therefore, each testing patient receives M predicted outcomes. Applying majority voting rule, final predictive results for all testing patients are obtained using equation (8).
c) Calculate accuracy, sensitivity, and specificity from the predicted labels and their corresponding real labels.
End for
Outputs
   Calculate averaged results of K iterations.
   Store, display, and analyze the final results.

Instead of selecting all segments, a selective segment (SS) method can be used. The SS method selects only some of the segments.

The rationale behind the SS method is to select some "optimal" segments to minimize the intra-class difference where Euclidean distance [6] is employed as the selection criteria. Specifically, within the feature set, the class center is determined and the distances between each of M segments of any patient and the center are calculated. Let $M'$ be the number of selected segments, then $M'$ segments will be retained, which are closer to the corresponding class center than the discarded segments. As a result, the size of data set has been reduced from N×M to N×M'. Since the selecting operation is supervised (the class information is used), the selection of segments can be considered as a pre-processing for the original data set. The complete SS algorithm is provided below.

SS Algorithm
Inputs
   ECG signals $S_1, \ldots, S_N$.
   Vital signs and patient outcomes $y_1, \ldots, y_N$.
   Number of iterations K, number of total segments M, and number of selected segments M'.

Calculation of HRV Measures
1. Do steps 1-3 in TS algorithm to obtain M segments for each patient.
2. Calculate class centers as $$C_0 = \frac{1}{N^0} \sum_{x_i \in \omega_0} x_i \text{ and } C_1 = \frac{1}{N^1} \sum_{x_i \in \omega_1} x_i$$

where $N^i$ is the number of samples in class $\omega_i$, for i=0, 1.
3. Calculate Euclidean distances $d_n^m$ between N and M segments and the class centers $C_0$, $C_1$.
4. Sort the distances and select M' segments that are closer to the corresponding center than other segments for each patient individually.

5. Construct feature vectors $x_n^{m'}$ with $z_n^{m'}$ and vital signs, where m'=1; M'.

Prediction of ACP Event or Mortality

For k=1, ..., K

Do steps a)-c) in TS algorithm with a data set created by using M' selected segments instead of the total M segments.

End for

Outputs

Calculate averaged results of K iterations.

Store, display, and analyze the final results.

In summary, any of the above methods to classify an artificial neural network may be used to facilitate a method of predicting the survivability of a patient.

Figure 14:
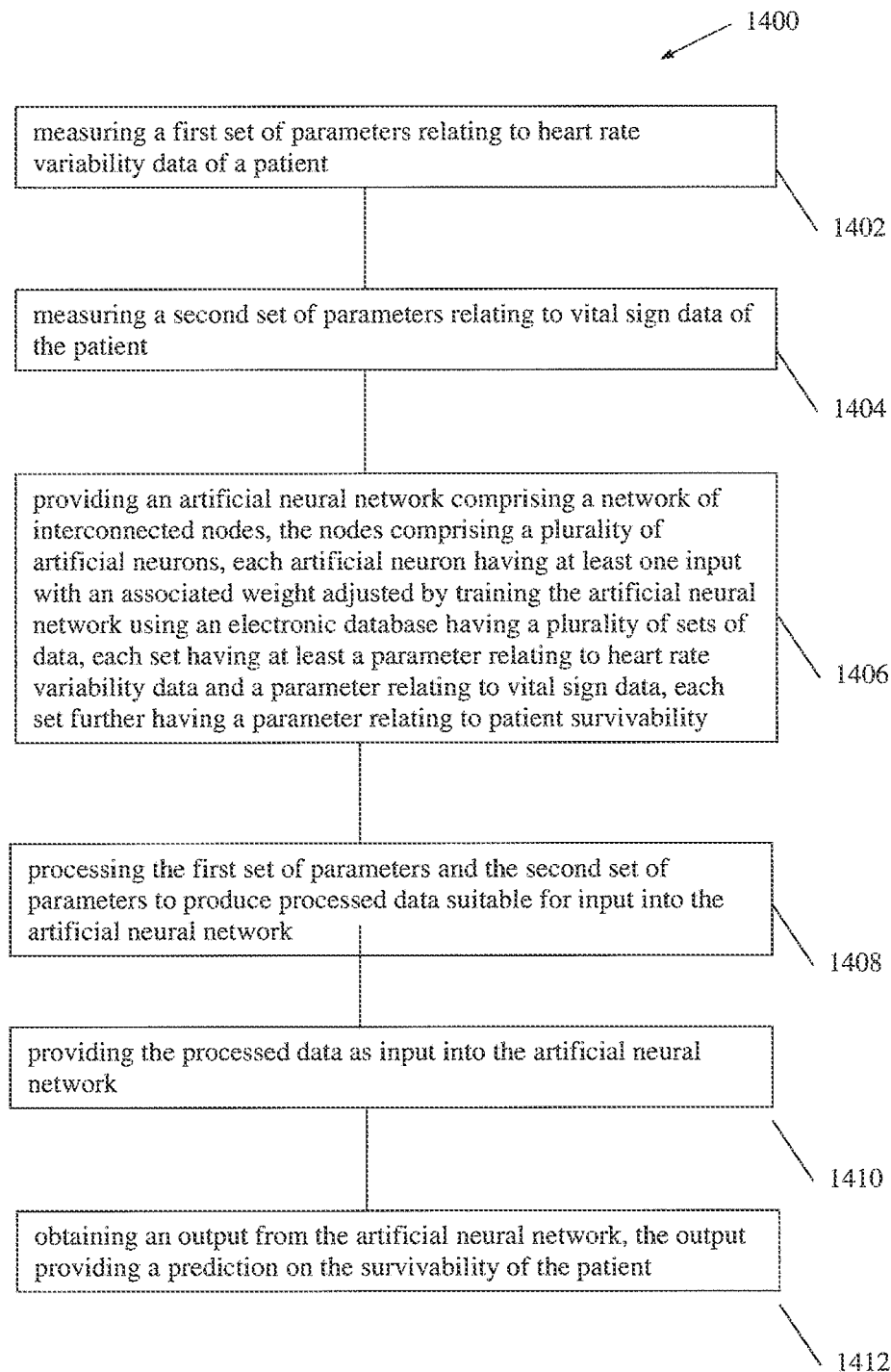
FIG. 14 shows a flow chart illustrating a method, according to one embodiment of the present invention, of predicting the ACP events and survivability of a patient.

FIG. 14 is a flow chart 1400 illustrating a method, according to one embodiment of the present invention, of predicting the survivability of a patient.

In step 1402, a first set of parameters relating to heart rate variability data of a patient is measured.

In step 1404, a second set of parameters relating to vital sign data of the patient is measured.

In step 1406, an artificial neural network including a network of interconnected nodes is provided, the nodes including a plurality of artificial neurons. Each artificial neuron has at least one input with an associated weight adjusted by training the artificial neural network using an electronic database having a plurality of sets of data. Each set of data has at least a parameter relating to heart rate variability data and a parameter relating to vital sign data, each set of data further having a parameter relating to patient survivability.

In step 1408, the first set of parameters and the second set of parameters are processed to produce processed data suitable for input into the artificial neural network.

In step 1410, the processed data is provided as input into the artificial neural network.

In step 1412, an output is obtained from the artificial neural network, the output providing a prediction on the survivability of the patient.

In embodiments of the invention, the processed data of the first set of parameters and the processed data of the second set of parameters may be represented as a feature vector.

In embodiments of the invention, the processed data may be the first set of parameters and the second set of parameters being represented as normalized data.

In embodiments of the invention, the processed data may be partitioned into non-overlapping segments, so that the input into the artificial neural network may include sets of one or more of the non-overlapping segments of processed data. A result may be obtained for each of the sets of one or more of the non-overlapping segments of processed data, so that each of the results may be considered to predict the survivability of the patient.

In embodiments of the invention, majority voting may be used to determine the prediction on the survivability of the patient, the majority voting represented by the function $$\hat{y} = \max_{j=1}^{2} \sum_{m=1}^{M} D_{m,j}$$

wherein $D_{m,j}$ is an intermediate variable for final decision making, $D_{m,j}$ assigned a value of 1 if a $m^{th}$ classifier chooses class j in the decision ensemble, and 0 otherwise.

In embodiments of the invention, the result of the artificial neural network may be coded as a two class label. The method of predicting the survivability of a patient may then further include applying a label-based algorithm to each of the two class label results to decide the output from the artificial neural network, thereby providing a prediction on the survivability of the patient.

In embodiments of the invention, the heart rate variability data may include time domain data, frequency domain data and geometric domain data.

Figure 15:
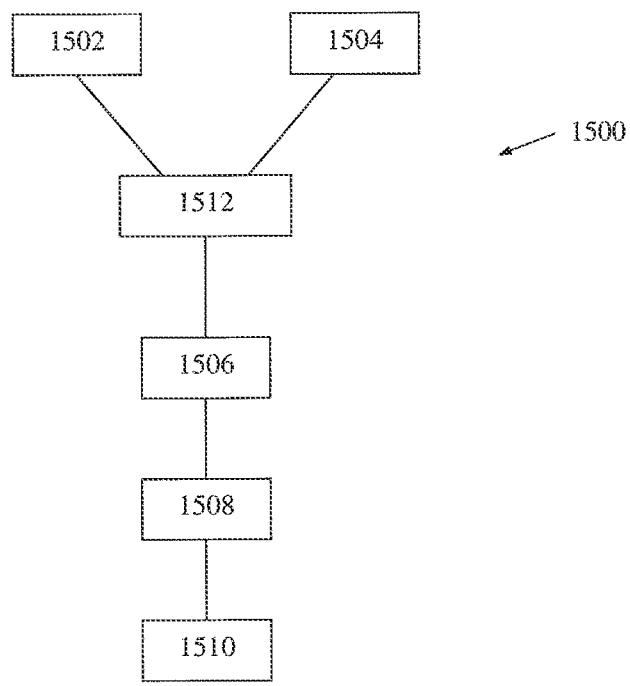
FIG. 15 shows a schematic of a patient ACP events and survivability prediction system in accordance with embodiments of the invention.

FIG. 15 shows a schematic of a patient survivability prediction system 1500 in accordance with embodiments of the invention.

The patient survivability prediction system 1500 includes a first input 1502 to receive a first set of parameters relating to heart rate variability data of a patient and a second input 1504 to receive a second set of parameters relating to vital sign data of the patient.

The patient survivability prediction system 1500 includes a memory module 1506 storing instructions to implement an artificial neural network. The artificial neural network includes a network of interconnected nodes, the nodes including a plurality of artificial neurons. Each artificial neuron has at least one input with an associated weight adjusted by training the artificial neural network using an electronic database having a plurality of sets of data. Each set of data has at least one a parameter relating to heart rate variability data and a parameter relating to vital sign data. Each set of data further has a parameter relating to patient survivability.

The patient survivability prediction system 1500 further includes a processor 1508 to execute the instructions stored in the memory module 1506 to perform the functions of the artificial neural network and output a prediction on the survivability of the patient based on the first set of parameters and the second set of parameters. A display 1510 displays the prediction on the survivability of the patient.

In embodiments of the invention, the patient survivability prediction system 1500 includes a port 1512 to receive the first set of parameters from the first input 1502 and the second set of parameters from the second input 1504.

Figure 16:
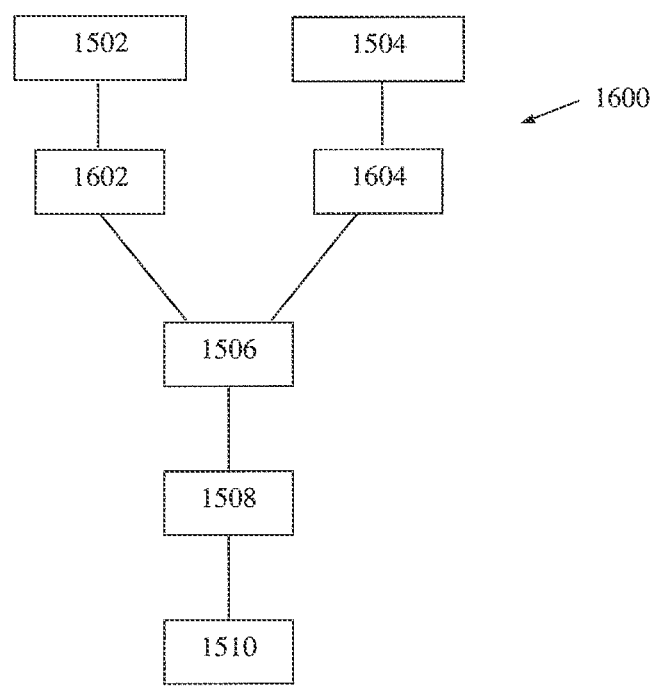
FIG. 16 shows a schematic of a patient ACP events and survivability prediction system in accordance with embodiments of the invention.

FIG. 16 shows a schematic of a patient survivability prediction system 1600 in accordance with embodiments of the invention.

The patient survivability prediction system 1600 shares similar components with the patient survivability prediction system 1500 of FIG. 15. The main contrast between the patient survivability prediction system 1600 and the patient survivability prediction system 1500 of FIG. 15 is that the patient survivability prediction system 1600 does not use a single port to receive the first set of parameters from the first input 1502 and the second set of parameters from the second input 1504. Rather, the patient survivability prediction system 1600 has a first port 1602 to receive the first set of parameters from the first input 1502 and a second port 1604 to receive the second set of parameters from the second input 1504.

Figure 17:
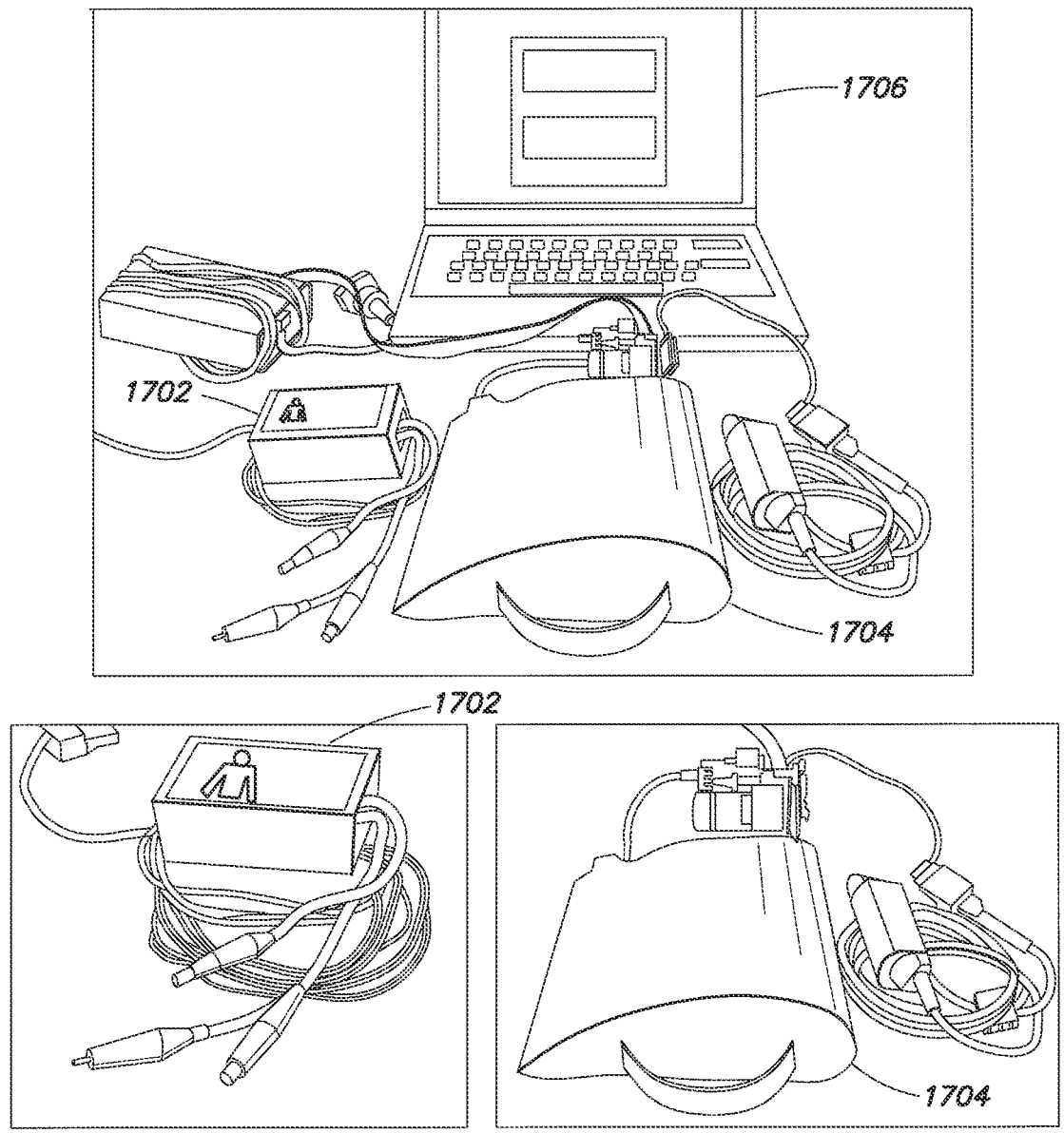
FIG. 17 shows pictures of a patient ACP events and survivability prediction system in accordance with embodiments of the invention.

FIG. 17 shows pictures of a patient survivability prediction system 1700 in accordance with embodiments of the invention.

In FIG. 17, the patient survivability prediction system has ECG sensors 1702 and a blood pressure sensor 1704. The artificial neural network used to predict patient survivability is implemented in a laptop 1706.

FIGS. 18 to 21 show snap shots of the output of the patient survivability prediction system as shown in the laptop 1706 screen.

Figure 18:
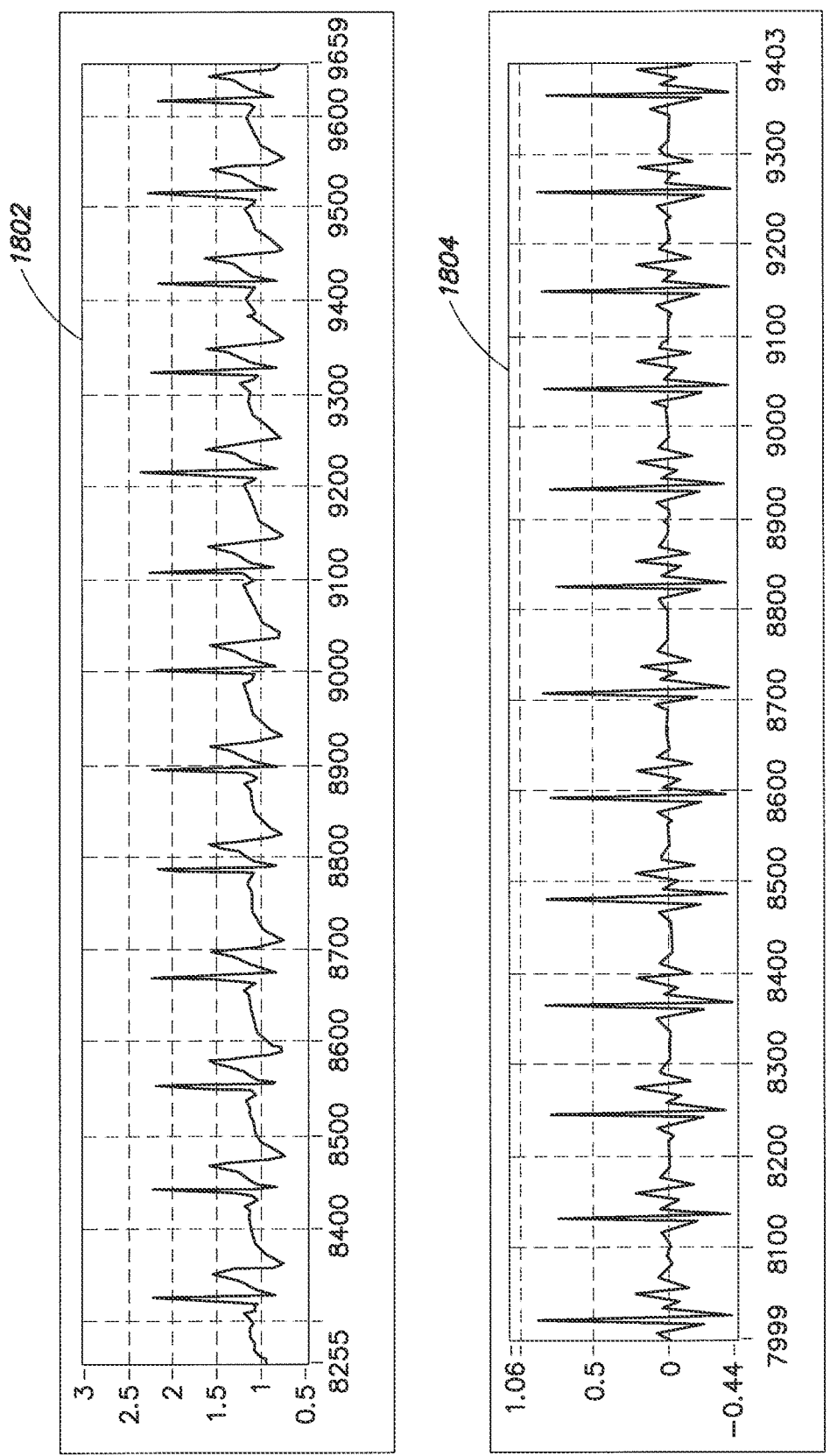

FIG. 18 shows the result of processing raw ECG data 1802 to produce filtered ECG data 1804.

Figure 19:
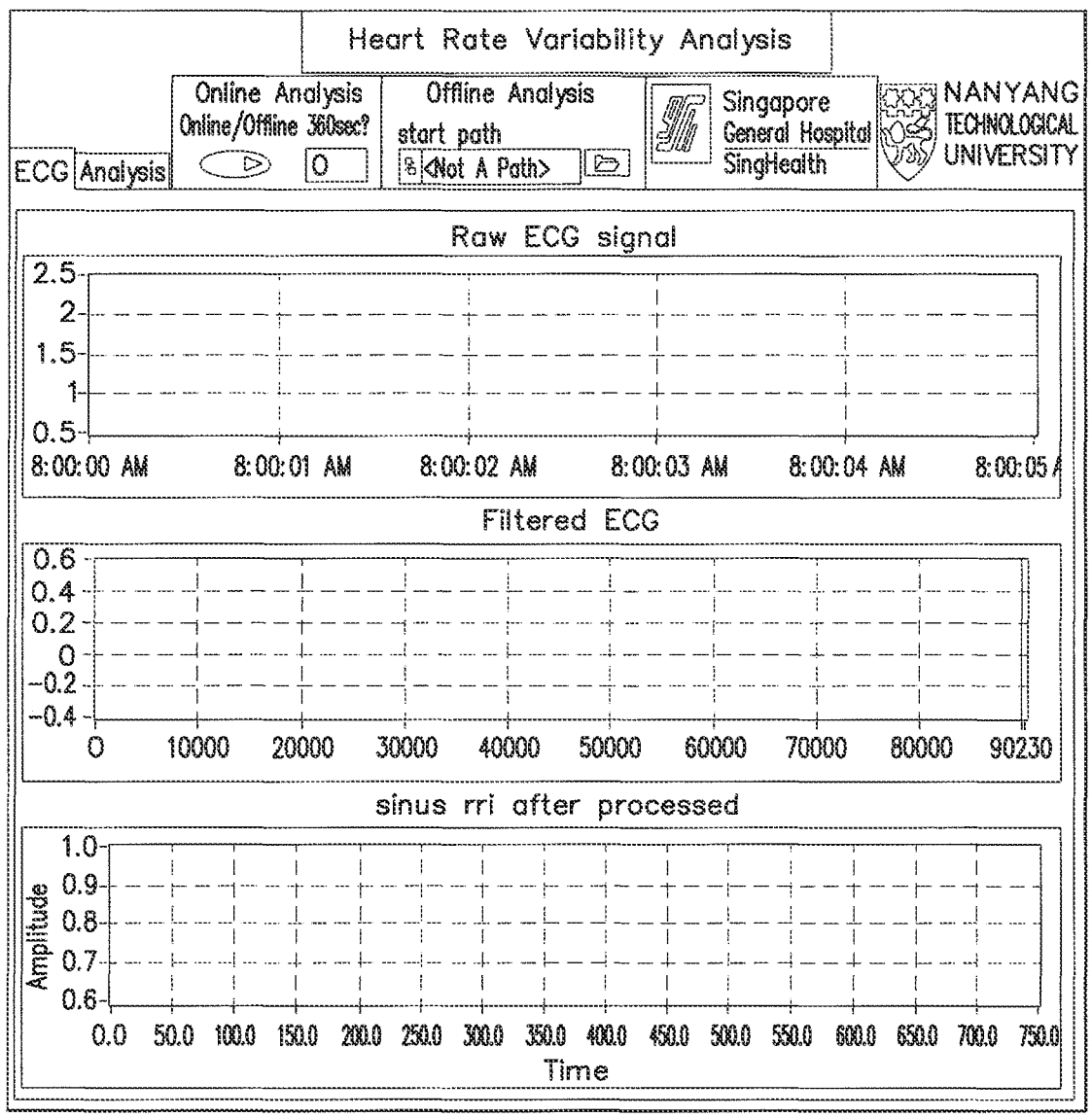

FIG. 19 shows various signal graphs that the patient survivability prediction system 1700 is able to display.

FIG. 20 shows the prediction results of two different patients, where in one case (2102), cardiac arrest is predicted to not occur within 72 hours. In the other case (2104), cardiac arrest is predicted to occur within 72 hours.

Figure 21:
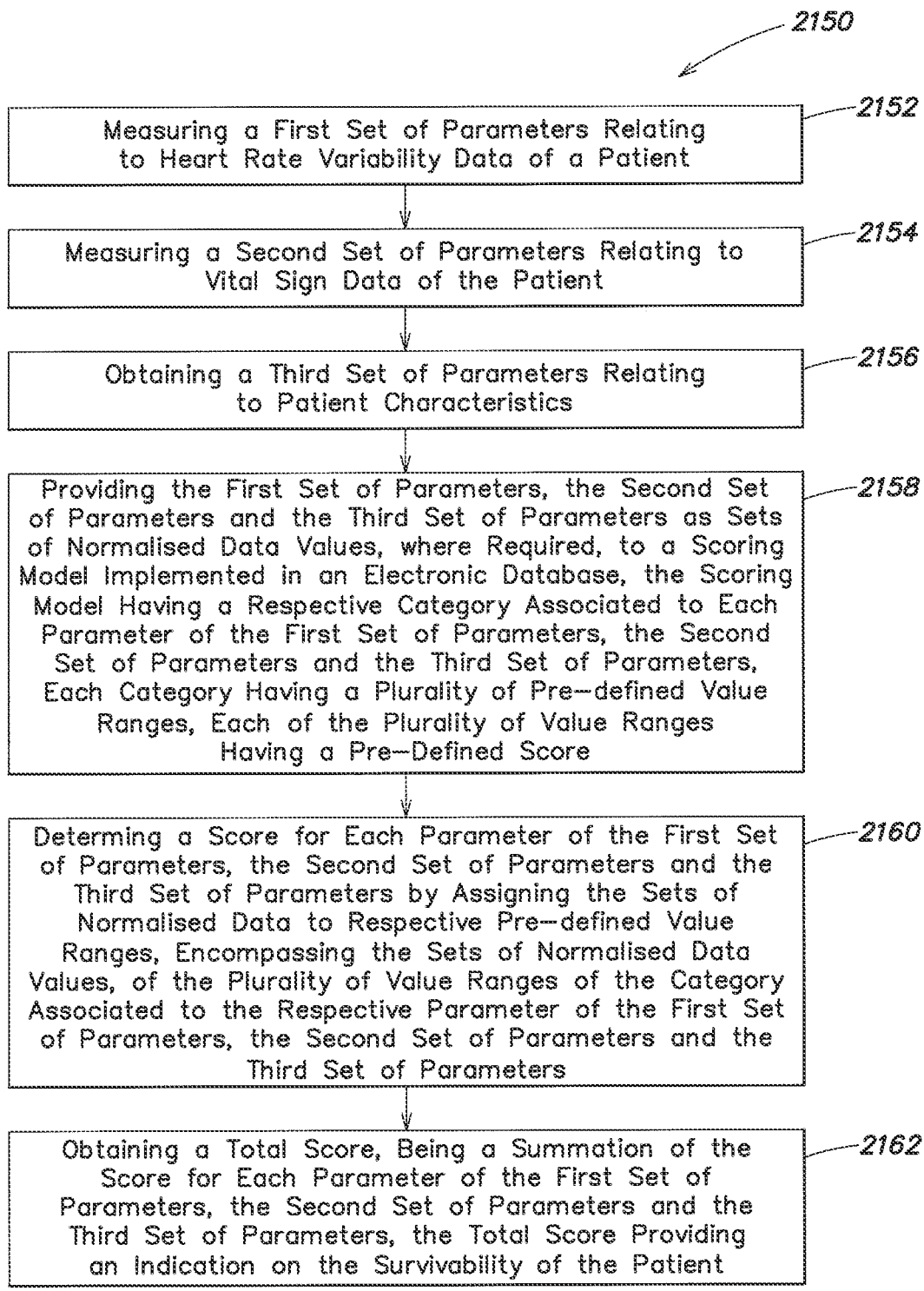
FIG. 21 shows a flow chart illustrating a method, according to one embodiment of the present invention, used to predict the ACP events and survivability of a patient.

FIG. 21 shows a flow chart 2150 illustrating a method, according to one embodiment of the present invention, used to predict the survivability of a patient.

The method includes six steps, 2152, 2154, 2156, 2158, 2160 and 2162.

In step 2152, a first set of parameters relating to heart rate variability data of a patient is measured.

In step 2154, a second set of parameters relating to vital sign data of the patient is measured.

In step 2156, a third set of parameters relating to patient characteristics is obtained.

In step 2158, the first set of parameters, the second set of parameters and the third set of parameters are provided as sets of normalized data values, where required, to a scoring model implemented in an electronic database. The scoring model has a respective category associated to each parameter of the first set of parameters, the second set of parameters and the third set of parameters, each category having a plurality of pre-defined value ranges, each of the plurality of value ranges having a pre-defined score.

In step 2160, a score for each parameter of the first set of parameters, the second set of parameters and the third set of parameters is determined. The score is determined by assigning the sets of normalized data (from step 2158) to respective pre-defined value ranges, encompassing the sets of normalized data values, of the plurality of value ranges of the category associated to the respective parameter of the first set of parameters, the second set of parameters and the third set of parameters.

In step 2162, a total score, being a summation of the score (see step 2160) for each parameter of the first set of parameters, the second set of parameters and the third set of parameters, is obtained. The total score provides an indication on the survivability of the patient.

The method illustrated in FIG. 21 may be implemented in accordance to the example that follows, the example relating to predicting cardiac arrest in a patient within 72 hrs of assessment.

When a patient is delivered to a triage area for assessment, the patient's characteristics (such as age), vital signs (such as GCS, temperature, pulse rate, respiratory rate, SBP, DBP, SpO2 and pain score) and HRV parameters (time, frequency and geometric domain) will be recorded and analyzed by a patient survivability prediction system in accordance to an embodiment of the invention. In this embodiment, the measured HRV parameters become a first set of parameters, while the measured vital sign data form a second set of parameters. The patient characteristics form a third set of parameters, which may also be obtained from the patient's hospital records. It will be appreciated that further patient health data may also be recorded by the patient survivability prediction system.

The patient survivability prediction system may have an electronic database in which a scoring model is implemented. The scoring model may be based on a mathematical model which may be based on logistic regression, such as univariate analysis. In one embodiment, the logistic regression mathematical model may be used, for example, on data from samples of cardiovascular (CVS) and non-cardiovascular (non-CVS) patients. The logistic regression mathematical model may be fitted separately with a combination of demographic parameters (age), vital signs and HRV parameters for the CVS and non-CVS patients. The prediction performance may be investigated through Receiver Operating Characteristic (ROC) analysis as well as Sensitivity, Specificity, Positive Predictive Value (PPV) and Negative Predictive Value (NPV). Table 1 below summarizes the organization of first set of parameters, the second set of parameters and the third set of parameters inside a scoring model, according to one embodiment of the invention.

TABLE 1

Model based scoring scheme for demographic, vital sign and HRV parameters.

| Parameter & respective range of values | | Score |
|---|---|---|
| Age | <40 | 1 |
| | 40-49 | 2 |
| | 50-59 | 2 |
| | 60-69 | 3 |
| | 70-79 | 4 |
| | >=80 | 4 |
| GCS | <=5 | 6 |
| | 6-10 | 4 |
| | 11-14 | 3 |
| | 15 | 0 |
| Temperature | <36.5 | 5 |
| | 36.5-37.4 | 0 |
| | >37.4 | 4 |
| Pulse rate | <60 | 4 |
| | 60-99 | 1 |
| | 100-129 | 4 |
| | >=130 | 5 |
| Respiratory rate | <10 | 6 |
| | 10-16 | 3 |
| | >16 | 4 |
| SBP | <90 | 6 |
| | 90-120 | 2 |
| | >120 | 5 |
| DBP | <60 | 4 |
| | 60-95 | 2 |
| | >95 | 3 |
| SPO2 | <95 | 5 |
| | >=95 | 0 |
| Pain score | 0 | 0 |
| | 1-5 | 3 |
| | 6-10 | 4 |
| aRR(s) | <0.73 | 0 |
| | 0.73-0.95 | 0 |
| | >0.95 | 3 |
| STD(s) | <0.04 | 0 |
| | 0.04-0.08 | 0 |
| | >0.08 | 3 |
| avHR(bpm) | <63.46 | 0 |
| | 63.46-83.24 | 0 |
| | >83.24 | 3 |
| sdHR(bpm) | <3.84 | 0 |
| | 3.84-6.36 | 0 |
| | >6.36 | 3 |
| RMSSD | <0.02 | 0 |
| | 0.02-0.07 | 0 |
| | >0.07 | 3 |
| nn50 (count) | <3.34 | 0 |
| | 3.34-39.64 | 0 |
| | >39.64 | 3 |
| pnn50 (%) | <17.43 | 3 |
| | >=17.43 | 1 |
| RR triangular index | <3.20 | 5 |
| | >=3.20 | 3 |
| TINN (ms) | <0.18 | 3 |
| | 0.18-0.33 | 0 |
| | >0.33 | 0 |
| LS-VLF power (ms2) | <0.15 | 3 |
| | >=0.15 | 0 |
| LS-LF power (ms2) | <0.12 | 3 |
| | >=0.12 | 0 |

TABLE 1-continued

Model based scoring scheme for demographic, vital sign and HRV parameters.

| Parameter & respective range of values | | Score |
|---|---|---|
| LS-HF power (ms2) | <0.08 | 2 |
| | 0.08-0.20 | 3 |
| | >0.20 | 4 |
| LS-total power (ms2) | <0.46 | 3 |
| | >=0.46 | 0 |
| LS-LF power (nu) | <41.91 | 3 |
| | 41.91-70.76 | 0 |
| | >70.76 | 0 |
| LS-HF power (nu) | <29.24 | 0 |
| | 29.24-58.09 | 0 |
| | >58.09 | 3 |
| LS-LF/HF ratio | <0.62 | 3 |
| | 0.62-2.54 | 0 |
| | >2.54 | 0 |

As shown in table 1, the scoring model has a plurality of categories (Age, GCS, Temperature, Pulse rate, ..., LS-LF/HF ratio), with each category having a plurality of pre-defined value ranges (for instance: the category "age" has a range of values <40, 40-49, ..., >=80). Each of the plurality of pre-defined value ranges has a pre-defined score (for instance: for the category "age", the range of values <40, 40-49, ..., >=80 have scores 1, 2, ... and 4 respectively).

Each of the categories is associated to a respective parameter of the first set of parameters, the second set of parameters and the third set of parameters. For instance, the categories "aRR(s)", "STD(s)", ... and "LS-LF/HF ratio" are HRV parameters and are therefore, in this embodiment, associated with the first set of parameters. The "aRR, STD, ... and LS-LF/HF ratio" parameters of the first set of parameters will be associated with the corresponding "aRR(s), STD(s), ... and LS-LF/HF ratio" categories of the scoring model shown in table 1.

In table 1, both the predefined value ranges and their respective score values for the category "age" are derived, for example, from samples of CVS and non-CVS patients to group variables. Both the predefined value ranges and their respective score values for vital signs (i.e. the categories "GCS", "temperature", "pulse rate", "respiratory rate", "SBP", "DBP", "SpO2" and "pain score") are derived according to data derived from samples of CVS and non-CVS patients. Both the predefined value ranges and their respective score values for the HRV parameters (i.e. the categories "aRR(s)", "STD(s)", ... and "LS-LF/HF ratio") are based on ECG studies of a healthy population in Singapore.

As shown in table 1, only required parameters from the first set of parameters, the second set of parameters and the third set of parameters are normalized. For instance, the parameter "age" from the first set of parameters and the parameter "temperature" from the second set of parameters do not need to be normalized as their corresponding categories in the scoring model are designed to process the actual recorded values from the patient.

Normalized data, where required, for each parameter of the first set of parameters, the second set of parameters and the third set of parameters is assigned to its associated category. Further, the normalized data is assigned to the respective value range within the associated category, the normalized data falling within or being encompassed by the respective value range. The purpose of assigning the normalized data to its respective value range within its associated category is to determine a score, based on the scoring method summarized in table 1, of the normalized data. From table 1, it can be observed that a maximum possible score is 100 and a minimum possible score is 15.

Table 2 below shows a summary of individual scores, obtained from using the scoring method summarized in table 1, for each parameter of a patient's demographic, vital sign and HRV parameters.

TABLE 2

Patient demographic, vital sign and HRV parameters

| Parameter & categories | | Score |
|---|---|---|
| Age | >=80 | 4 |
| GCS | 11-14 | 3 |
| Temperature | >37.4 | 4 |
| Pulse rate | >=130 | 5 |
| Respiratory rate | >16 | 4 |
| SBP | >120 | 5 |
| DBP | >95 | 3 |
| SPO2 | <95 | 5 |
| Pain score | 6-10 | 4 |
| aRR(s) | >0.95 | 3 |
| STD(s) | >0.08 | 3 |
| avHR(bpm) | >83.24 | 3 |
| sdHR(bpm) | >6.36 | 3 |
| RMSSD | >0.07 | 3 |
| nn50 (count) | >39.64 | 3 |
| pnn50 (%) | <17.43 | 3 |
| RR triangular index | <3.20 | 5 |
| TINN (ms) | <0.18 | 3 |
| LS-VLF power (ms2) | <0.15 | 3 |
| LS-LF power (ms2) | <0.12 | 3 |
| LS-HF power (ms2) | >0.20 | 4 |
| LS-total power (ms2) | <0.46 | 3 |
| LS-LF power (nu) | <41.91 | 3 |
| LS-HF power (nu) | >58.09 | 3 |
| LS-LF/HF ratio | <0.62 | 3 |
| Total score | | 88 |

As shown in table 2, a total score, being a summation of each score for each parameter of the first set of parameters, the second set of parameters and the third set of parameters, is obtained. The total score provides an indication on the survivability of the patient.

Table 3 below summarizes organization of a plurality of risk categories inside a scoring model in accordance to an embodiment of the invention.

TABLE 3

Organization of risk categories inside a scoring model

| Level of risk to have cardiac arrest within 72 hrs | Score |
|---|---|
| Low | 15-40 |
| Moderate | 41-60 |
| High | 61-80 |
| Very high | 81-100 |

Each category (such as low, moderate, high and very high) of the plurality of risk categories has a pre-defined range of values. The total score obtained in table 2 is assigning to the category having the pre-defined range of values encompassing the total score. Thus, for the total score "88" from table 2, the patient is assessed to have a "very high" level of risk to have cardiac arrest within 72 hours. In the embodiment shown in table 3, the numerical range of each of plurality of risk categories may be determined in an arbitrary manner.

Table 4 shows a summary of results obtained from using the scoring model, as shown in FIG. 21B, against actual results of whether cardiac arrest occurred within 72 hours for a sample of 1021 patients.

From table 4, the results obtained by using the scoring model of FIG. 21B indicates that for the 1021 patients, 26 (or 2.5% of the sample size) belonged to the "low" risk category, 661 (or 64.7% of the sample size) belonged to the "moderate" risk category, 333 (or 32.6% of the sample size) belonged to the "high" risk category, while 1 (or 0.1% of the sample size) belonged to the "very high" risk category. Single decimal place accuracy applies for the percentage values of the sample sizes.

Among the 26 patients of the "low" risk category, cardiac arrest did not occur. Amongst the 661 patients of the "moderate" risk category, 3.2% suffered cardiac arrest within 72 hours. Amongst the 333 patients of the "high" risk category, 9.0% suffered cardiac arrest within 72 hours. For the 1 patient of the "very high" risk category, cardiac arrest occurred within 72 hours.

TABLE 4

Assessment of scoring model against actual results

| Level of risk to have cardiac arrest within 72 hrs | Patient-at-risk n (%) | cardiac arrest within 72 hrs (%) | |
|---|---|---|---|
| | | No | Yes |
| Low | 26 (2.5) | 100.0 | 0.0 |
| Moderate | 661 (64.7) | 96.8 | 3.2 |
| High | 333 (32.6) | 91.0 | 9.0 |
| Very high | 1 (0.1) | 0.0 | 100.0 |

From table 4, the area under curve (AUC) at a 95% CI (confidence interval) of the scores to predict cardiac arrest within 72 hrs ranges from 0.633 to 0.769, to have an average accuracy of 0.701.

Experimental Data Set 1

Experiments were conducted where eight vital signs are used to form part of the feature vector for patient outcome prediction. These vital signs are temperature, respiration rate, pulse, systolic blood pressure (SBP), diastolic blood pressure (DBP), oxygen saturation (SpO2), Glasgow Coma Score (GCS), and pain score.

In the data set, each patient was represented as a 24-dimensional feature vector and the corresponding outcome coded as either 0 (survived and discharged) or 1 (died). Among 100 patients, 40 cases died and 60 cases survived. Prior to classification, the feature set is transformed into the interval [−1,1] by performing min-max normalization on the original data. Suppose that $min_A$ and $max_A$ are the minimum and maximum values of an attribute vector $A=[x_1(i), \ldots, x_N(i)]$ where $i \in [1, 24]$ and N is the total number of samples. Min-max normalization maps a value v, of A to v' in the range $[min'_A$ and $max'_A]$ by computing $$v' = \frac{v - min_A}{max_A - min_A}(max'_A - min'_A) + min'_A \quad (9)$$

This type of normalization preserves the relationships among the original data values, and therefore facilitates the prediction. To validate embodiments of the patient survivability prediction system, 75 patients were randomly selected for training and the rest 25 patients are used for testing. This partition and classification procedure is repeated 50 times, and the averaged output values are recorded.

Figure 22:
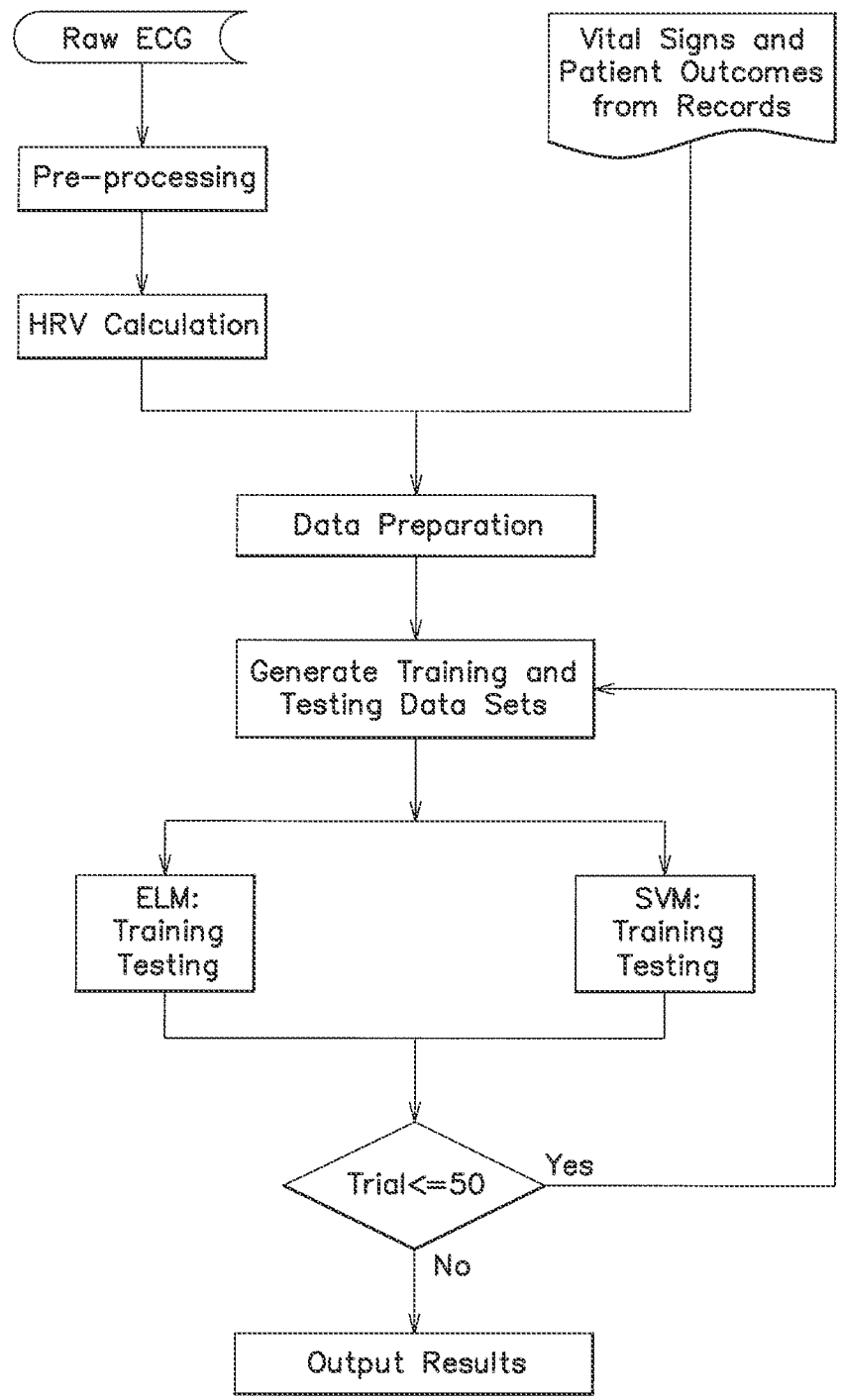
FIG. 22 shows a flow chart used by a validation system.

It is known from FIG. 11 that 60 patients belong to class 0 and 40 patients are categorized into class 1. As a consequence, random selection may result in biased training and testing sets, i.e., the sample number of two classes are unbalanced. Alternatively, random partitioning is done for both classes separately so that 75% samples in class 0 and 75% samples in class 1 will go into the training set in each iteration. The validation system is illustrated in FIG. 22. It is seen that the architecture depicted in FIG. 22 is straightforward like most pattern recognition systems, in which data acquisition, feature extraction, and classification are individually implemented.

In practice, the ECG recordings vary widely in length and signal quality. Therefore, several pre-processing steps are required to ensure qualified RR interval sequences. Before computing the HRV measures, the QRS detection and non-sinus beat detection algorithms were validated against the MIT-BIH database. These algorithms were found to perform well with high sensitivity (99.8%) and specificity (99.4%) in detecting QRS complexes and detecting non-sinus beats for ECG signals in the MIT-BIH database.

In the experiments, ELM and SVM are implemented for classification. Therefore, several parameters used in these algorithms should be clarified. In ELM, the number of hidden neurons is assigned as 30. For SVM, the default settings of the parameters in the LIBSVM package are used. To evaluate the predictive performances, sensitivity and specificity are calculated in addition to classification accuracy. Serving as widely used statistical measures for binary classification, sensitivity measures the ratio of the number of correctly predicted positive samples to the actual number of positives, and specificity is the proportion of negatives which are correctly identified. The decision was defined as positive if the patient outcome is death, while negative case refers to survival. Therefore, the following measures are obtained True positive (TP): Death case correctly predicted as death.

False positive (FP): Survival case wrongly predicted as death.

True negative (TN): Survival case correctly predicted as survival.

False negative (FN): Death case wrongly predicted as survival

Subsequently, sensitivity, specificity, and accuracy was determined and used to evaluate the proposed methods in the experiments.

Sensitivity=TP/(TP+FN)

Specificity=TN/(TN+FP)

Accuracy=(TP+TN)/(TP+FP+TN+FN)

In general, high sensitivity, specificity, and accuracy are desired so that more cases in both classes can be correctly recognized.

Segment Based Prediction

In the implementation, each segment is set as 250 beats and 9 segments per patient are extracted from the original RR interval sequences. By applying the voting-based predictive strategy on three selected segments (M'=3), the classification results using vital signs, HRV measures, and combined features are presented in FIGS. 23, 24 and 25 respectively.

FIGS. 23 and 24 show the prediction results with traditional vital signs and HRV measures, respectively. It can be observed that SVM generally outperforms ELM with respect to accuracy and specificity. Both ELM and SVM algorithms achieve comparable performance in terms of sensitivity. Compared with the results based on vital signs, the results based on HRV measures give higher accuracy and sensitivity using ELM. Using SVM, results based on vital signs and HRV measures produce similar performance in terms of accuracy. In addition, sensitivity is increased and specificity is reduced by replacing vital signs with HRV measures. In general, prediction of mortality with either HRV measures or vital signs individually is not satisfactory. By combining the HRV measures and the vital signs, the best results (Accuracy: 78.32%, Sensitivity: 65%, Specificity: 87.2%) are obtained using SVM with linear kernel, as can be seen from FIG. 25. From these results, it is observed that combining the HRV measures and the vital signs can improve the performance of prediction in general.

Several parameters may affect the final results, particularly the number of selected segments M'. Hence, prediction results with different values of the parameter M' are investigated in the following. When M'=M, the entire collection of segments are selected, i.e., the TS method. If M'<M, M' segments for generating a more compact data set (i.e., a smaller intra-class variation) are employed for prediction. In applying the majority voting for a two-class problem, an odd number of predictors should be used for decision combination. Consequently, different M' segments are selected for voting and the results are shown in FIG. 26. It is observed that when M' is 3, SVM performs the best and ELM can achieve good results as well. Furthermore, with the increment of M', the number of samples in the data set increases. Therefore, M' is set as 3 in order to maintain a simple but effective prediction system for clinical usage.

Comparison of Different Predictive Strategies

The predictive strategies are summarized as follows and illustrated in FIG. 27.

Global: The HRV measures are calculated from the entire RR interval sequence where the length of signal varies from 2273 beats to 21697 beats.

Local: The HRV measures are calculated from a local sequence which is the last portion (2250 beats long) of the original signal.

Total segment: All non-overlapped segments in the local sequence are used for prediction by the majority voting rule. In this study, each segment is 250 beats long, and therefore 9 segments per patient are obtained from local sequence.

Selective segment: M' selected non-overlapped segments in the local sequence are used for prediction by the majority voting rule. Since M' segments are selected, signal of M'×250 beats long per patient is used for analysis.

As seen in FIG. 28, in some cases the Global strategy outperforms the Local strategy, and vice versa in other cases, but the best results are achieved by using the selective segment method.

Experimental Data Set 2

In another study, eight vital signs and raw ECG data were acquired from critically ill patients at the Department of Emergency Medicine (DEM), Singapore General Hospital (SGH). These vital signs include temperature, respiration rate, pulse, systolic blood pressure (SBP), diastolic blood pressure (DBP), oxygen saturation (SpO2), Glasgow coma score (GCS), and pain score. The ECG signals are acquired using LIFEPAK 12 defibrillator/monitor and downloaded using the CODESTAT Suite. To ensure that qualified RR intervals are used for calculating HRV measures, only cases containing more than 70% sinus rhythm are included in the data set. In summary, 100 patients are chosen for analysis, among which 40 cases are died and 60 cases are survived to discharge.

In the data set, each patient is represented as a 24-dimensional feature vector (16 HRV measures and 8 vital signs) and the corresponding outcome is coded as either 0 (survived to discharge) or 1 (died). In the experiments, 75 patients are randomly selected for training and the remaining 25 patients are used for testing. This procedure of partition and classification is repeated 50 times, and the final results are the averaged output values. However, random selection of samples may result in unbalanced training and testing sets, we therefore do the random partition for each class individually so that 75% samples in class 0 and 75% samples in class 1 will go into the training set in each iteration.

Prior to implementing ELM for classification, min-max normalization is performed to transform the feature set into the interval [−1,1], and the number of hidden neurons is heuristically determined as 30. Furthermore, sensitivity, specificity, and classification accuracy are calculated to evaluate the predictive performances. In the following, experimental results are reported and analyzed.

Segment Based Analysis of Patient Outcome

Within the data set of 100 patients, the length of RR interval varies from 2273 beats to 21697 beats, hence the maximal length of local sequence is 2273 beats. The local sequence was divided into 9 segments (M=9), each of which was 250 beats long. By applying the segment based predictive strategy, the classification results using vital signs, HRV measures, and combined features are presented in FIG. 29. It can be observed that the best results (Accuracy: 70.88%, Sensitivity: 47.93%, Specificity: 78.92%) are obtained using combined features with sigmoid activation function, and prediction of mortality with either HRV measures or vital signs is not satisfactory. When vital signs and HRV measures are used individually, higher sensitivity is achieved by HRV measures, whereas vital signs outperform in prediction specificity. From the FIG. 29, it is observed that combining the HRV measures and vital signs can generally improve the performance of prediction.

In practice, the number of hidden nodes in ELM usually controls the network complexity and learning performance, and thus may affect the final results.

Figures 30, 31, 32:
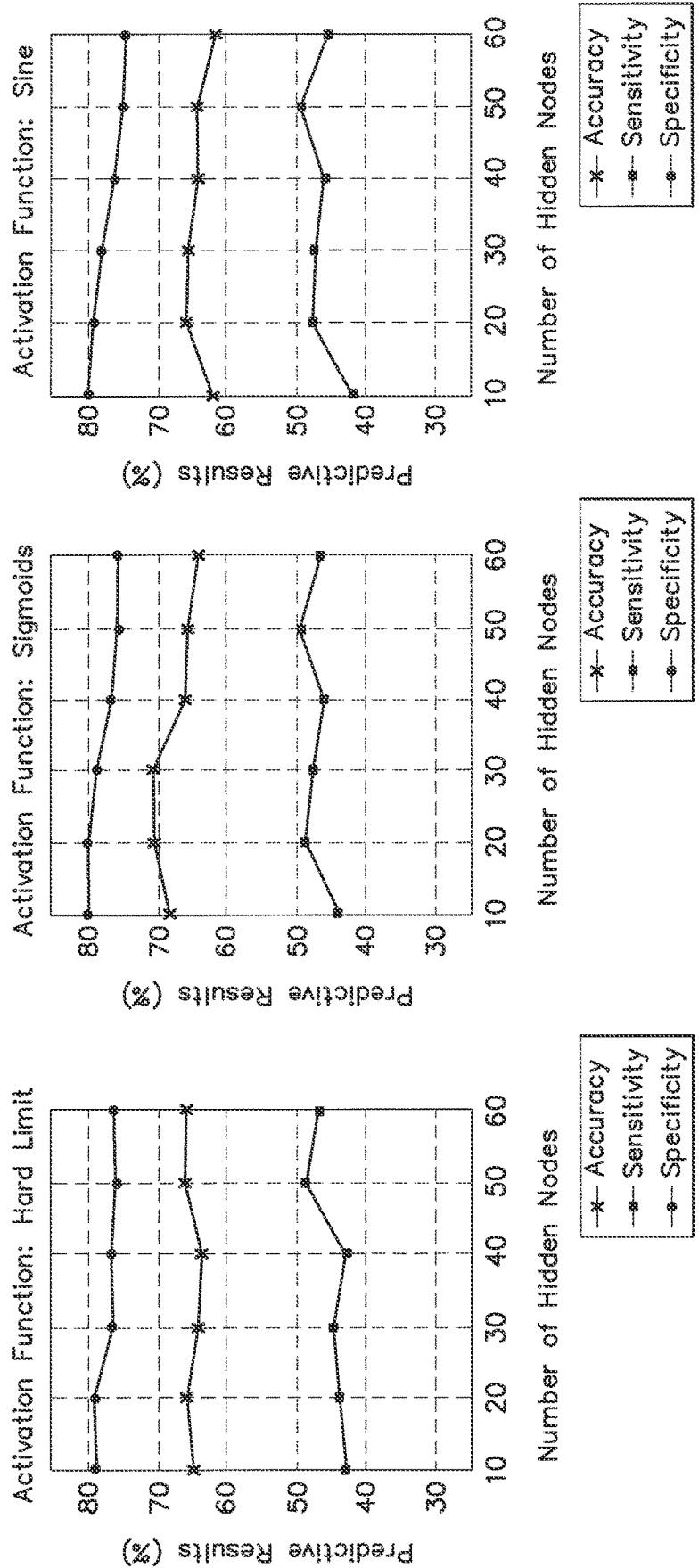
FIGS. 30, 31 and 32 depict the performances of extreme learning machine (ELM) in terms of different number of hidden nodes.

FIGS. 30, 31 and 32 depict the performances of ELM in terms of different number of hidden nodes. In FIGS. 30 to 32, the following activation functions were respectively used: hard limit, sigmoid and sine.

It is seen that good prediction results are obtained when the number of hidden nodes varies from 20 to 30 regardless of activation functions. We also observe that the best results are obtained using 30 hidden neurons with sigmoid function. Moreover, as seen in FIG. 29, both training and testing with ELM can be accomplished within several milliseconds.

Comparison of Different Predictive Strategies

The three predictive strategies used according to the way that the HRV measures are calculated from the ECG signal are the global, local, and segment based methods. Detailed descriptions of these strategies are as follows.

Global based method: The HRV measures are calculated from the entire RR interval sequence.

Local based method: The HRV measures are calculated from a local sequence to represent the patient.

Segment based method: All non-overlapped segments in the local sequence are used for prediction with majority voting rule.

It is obvious that one set of features are used to represent the patient when the global and local strategies are implemented, while M sets of features are calculated for one patient if the segment based method is adopted. As seen in FIG. 33, the local strategy outperforms the global strategy, and the best results are achieved by the segment based method.

What is claimed is:

1. A method of predicting a survivability of a patient, comprising acts of:
    receiving a first set of parameters relating to heart rate variability data of the patient based on ECG data of the patient;
    receiving a second set of parameters relating to non-ECG vital sign data of the patient, the non-ECG vital sign data including one or more of: a blood oxygen saturation level of the patient, a temperature of the patient, blood pressure of the patient, or a respiration rate of the patient;
    storing the first set of parameters and the second set of parameters; and
    analyzing the first set of parameters and the second set of parameters to provide a prediction on the survivability of the patient over the next 72 hours based on the first set of parameters and the second set of parameters; and
    displaying the prediction on the survivability of the patient over the next 72 hours.

2. The method of claim 1, further comprising an act of:
    receiving a third set of parameters including one or more of demographic information of the patient or medical history information of the patient, wherein the act of analyzing includes analyzing the first set of parameters, the second set of parameters, and the third set of parameters to provide the prediction on the survivability of the patient over the next 72 hours based on the first set of parameters, the second set of parameters, and the third set of parameters.

3. The method of claim 1, further comprising an act of:
    receiving a third set of parameters including demographic information of the patient and medical history information of the patient, wherein the act of analyzing includes analyzing the first set of parameters, the second set of parameters, and the third set of parameters to provide the prediction on the survivability of the patient over the next 72 hours based on the first set of parameters, the second set of parameters, and the third set of parameters.

4. The method of claim 3, wherein the acts of storing, analyzing, and displaying are performed on a portable device.

5. The method of claim 3, wherein the portable device is a handheld portable device.

6. The method of claim 4, further comprising an act of wirelessly communicating the heart rate variability data of the patient, the non-ECG vital sign data of the patient, the demographic information of the patient, the medical history information of the patient, and the prediction on the survivability of the patient over the next 72 hours to one or more of a hospital server, another portable device, or an emergency center server for analysis by clinicians.

7. The method of claim 3, wherein the demographic information of the patient includes one or more of: an age, a gender, or an ethnicity of the patient.

8. The method of claim 7, wherein the medical history information of the patient includes one or more of: a Glasgow Coma Scale score, any specific medications the patient is using, or a history of any medical conditions including diabetes, high blood pressure, or myocardial infarction.

9. The method of claim 3, wherein the medical history information of the patient includes one or more of: a Glasgow Coma Scale score, any specific medications the patient is using, or a history of any medical conditions including diabetes, high blood pressure, or myocardial infarction.

10. The method of claim 1, wherein the non-ECG vital sign data of the patient includes the blood oxygen saturation level of the patient, the temperature of the patient, the blood pressure of the patient, and the respiration rate of the patient.

11. The method of claim 10, wherein the blood pressure of the patient includes a systolic blood pressure of the patient and a diastolic blood pressure of the patient.

12. The method of claim 11, wherein the non-ECG vital sign data of the patient further includes one or more of: a pulse rate of the patient, a Glasgow Coma Scale score of the patient, or a pain score of the patient.

13. The method of claim 1, wherein the heart rate variability data of the patient includes one or more of: time domain data, frequency domain data, or geometric domain data.

14. The method of claim 1, wherein the heart rate variability data of the patient includes time domain data, frequency domain data, and geometric domain data.

15. The method of claim 1, wherein the prediction on the survivability of the patient over the next 72 hours is either death or survival of the patient.

16. The method of claim 1, wherein the acts of storing, analyzing, and displaying are performed on a portable device.

17. The method of claim 16, further comprising an act of communicating the prediction on the survivability of the patient over the next 72 hours to a hospital server.

18. The method of claim 16, further comprising an act of wirelessly communicating the heart rate variability data of the patient, the non-ECG vital sign data of the patient, and the prediction on the survivability of the patient over the next 72 hours to one or more of a hospital server, another portable device, or an emergency center server for analysis by clinicians.

19. The method of claim 16, wherein the portable device is a handheld portable device.

20. The method of claim 16, wherein the portable device is wearable by the patient.

21. The method of claim 1, wherein the acts of storing and analyzing are performed on a portable device, and wherein the act of displaying is performed on one or more of one or more of a hospital server, another portable device, or an emergency center server.

* * * * *